US012612441B2

(12) United States Patent
Jie

(10) Patent No.: US 12,612,441 B2
(45) Date of Patent: Apr. 28, 2026

(54) POLYPEPTIDE AND THERAPEUTIC USES THEREOF

(71) Applicant: Vitalixir (Beijing) Co., Ltd, Beijing (CN)

(72) Inventor: Han Jie, Beijing (CN)

(73) Assignee: VITALIXIR (BEIJING) CO., LTD, Beijing (CN)

( * ) Notice: Subject to any disclaimer, the term of this patent is extended or adjusted under 35 U.S.C. 154(b) by 1134 days.

(21) Appl. No.: 17/421,297

(22) PCT Filed: Jan. 7, 2020

(86) PCT No.: PCT/CN2020/070697

§ 371 (c)(1),
(2) Date: Jul. 7, 2021

(87) PCT Pub. No.: WO2020/143625

PCT Pub. Date: Jul. 16, 2020

(65) Prior Publication Data

US 2022/0127323 A1 Apr. 28, 2022

(30) Foreign Application Priority Data

Jan. 7, 2019 (CN) ......................... 201910014669.9

(51) Int. Cl.

| | |
|---|---|
| ***A61K 38/00*** | (2006.01) |
| ***A61K 38/26*** | (2006.01) |
| ***A61P 3/04*** | (2006.01) |
| ***A61P 3/06*** | (2006.01) |
| ***A61P 3/10*** | (2006.01) |
| ***C07K 14/00*** | (2006.01) |
| ***C07K 14/605*** | (2006.01) |

(52) U.S. Cl.

CPC .............. *C07K 14/605* (2013.01); *A61P 3/04* (2018.01); *A61P 3/06* (2018.01); *A61P 3/10* (2018.01); *A61K 38/00* (2013.01)

(58) Field of Classification Search

CPC . A61K 38/00; A61K 38/26; A61P 3/04; A61P 3/06; A61P 3/10; C07K 14/001; C07K 14/605

See application file for complete search history.

(56) References Cited

U.S. PATENT DOCUMENTS

| | | | | |
|---|---|---|---|---|
| 3,773,919 | A | 11/1973 | Boswell et al. | |
| 4,522,811 | A | 6/1985 | Eppstein et al. | |
| 2014/0018291 | A1 | 1/2014 | Vignati et al. | |
| 2022/0168396 | A1 * | 6/2022 | Wu ........................ | A61K 38/26 |

FOREIGN PATENT DOCUMENTS

| | | | |
|---|---|---|---|
| CN | 104470948 | A | 3/2015 |
| CN | 104902919 | | 9/2015 |
| CN | 104945499 | | 9/2015 |
| CN | 105934257 | A | 9/2016 |
| JP | 2016-503772 | A | 2/2016 |
| JP | 2016-506401 | A | 3/2016 |
| WO | WO 2017/204219 | A1 | 11/2017 |

OTHER PUBLICATIONS

Berge et al., "Pharmaceutical Salts," Journal of Pharmaceutical Sciences, Jan. 1977, 66(1):1-19.
Coskun et al., "LY3298176, a novel dual GIP and GLP-1 receptor agonist for the treatment of type 2 diabetes mellitus: From discovery to clinical proof of concept," Molecular Metabolism, Oct. 3, 2018, 18:3-14.
International Preliminary Report on Patentability in International Appln. No. PCT/CN2020/070697, dated Jun. 16, 2021, 14 pages.
International Search Report in International Appln. No. PCT/CN2020/070697, dated Mar. 27, 2020, 20 pages.
Meier, "GLP-1 receptor agonists for individualized treatment of type 2 diabetes mellitus," Nat. Rev. Endocrinol., 2012, 8:728-742, 15 pages.
Holst, "The Physiology of Glucagon-like Peptide 1," Physiol. Rev., Oct. 1, 2007, 87:1409-1439.
Extended European Search Report in European Appln. No. 20737905.8, mailed on Oct. 11, 2022, 7 pages.
Office Action in Chinese Appln. No. 202080008177.X, mailed on Oct. 12, 2023, 11 pages (with English translation).
Office Action in Japanese Appln. No. 2021-539604, mailed on Jul. 11, 2022, 11 pages (with English translation).

* cited by examiner

*Primary Examiner* — Julie Ha
(74) *Attorney, Agent, or Firm* — Fish & Richardson P.C.

(57) ABSTRACT

The present application provides a peptide compound of formula (VII) and its use in medical treatment.

9 Claims, 7 Drawing Sheets

Specification includes a Sequence Listing.

POLYPEPTIDE AND THERAPEUTIC USES THEREOF

CROSS-REFERENCE TO RELATED APPLICATION

This application is a National Stage Application under 35 U.S.C. § 371 and claims the benefit of International Application No. PCT/CN2020/070697, filed Jan. 7, 2020, which claims priority to Chinese Patent Application No. 201910014669.9, filed Jan. 7, 2019. The disclosures of the foregoing applications are hereby incorporated by reference in their entireties.

SEQUENCE LISTING

This application contains a Sequence Listing that has been submitted electronically as an ASCII text file named "52556-0002US1_SL". The ASCII text file, created on Jul. 5, 2021, is 125 kilobytes in size. The material in the ASCII text file is hereby incorporated by reference in its entirety.

TECHNICAL FIELD

The invention relates to a peptide compound and its use in medical treatment.

BACKGROUND OF THE INVENTION

Metabolic syndrome is a combination of multiple medical disorders that increase the risk of developing type 2 diabetes, atherosclerotic vascular disease, heart disease, and stroke. The medical parameters that define metabolic syndrome include diabetes mellitus, impaired glucose tolerance, increased fasting blood glucose, insulin resistance, central obesity, hypertension, elevated total cholesterol and triglycerides, elevated low-density cholesterol, and reduced high-density cholesterol. Diabetes includes type 1 diabetes, type 2 diabetes, and gestational diabetes. According to data from the World Health Organization (WHO), the prevalence of diabetes in developed countries is 5% to 10%. The number of people with diabetes in the world is expected to approximately double between 2000 and 2030. More than 50% of all individuals with diabetes in the world are undiagnosed, and there are more people with prediabetes than people with diabetes. For example, people with diabetes in China has reached 114 million, and another 500 million have impaired glucose tolerance and glucose metabolism, and on their way to become diabetic. More than half of the patients do not know they are sick. The great harm of diabetes mainly lies in serious complications and high mortality. The data show that diabetes is the leading cause of lower limb amputation and adult blindness.

Obesity is a medical condition and accumulation of excess body fat may have an adverse effect on health and life expectancy. Due to its prevalence in adults and children it has become one of the leading preventable causes of death in modern world. It increases the likelihood of various other diseases, including heart disease, type 2 diabetes, obstructive sleep apnea, certain types of cancer, and osteoarthritis. It is most commonly caused by a combination of excess food intake, reduced energy expenditure, and genetic susceptibility. With the same body mass index (BMI) Asians have higher visceral fat content than Caucasians and tend to have more severe insulin resistance than Caucasians. The insulin sensitivity of Asian type 2 diabetic patients with normal body weight decreases significantly in comparison to those non-diabetic people. Excess fat causes insulin resistance and β-cell damage, destroying blood glucose regulation. Various metabolic abnormalities associated with obesity significantly increase the risk of cardiovascular disease. According to clinical statistics, more than 70% of patients with type 2 diabetes are overweight. Therefore, reducing the weight and body fat of diabetic patients is an important approach to effectively control or even reverse diabetes progression. Existing small molecule weight-loss drugs have very serious side effects. Glucagon-like peptide-1 (GLP-1) receptor agonists can control blood glucose by promoting insulin secretion, increasing insulin sensitivity, and reducing the release of glucagon. Therefore, GLP-1 drugs are suitable for the treatment of metabolic diseases, especially diabetes. GLP-1 receptor agonists (e.g. exenatide, liraglutide) have shown weight-reducing effects in animal experiments and clinical trials with relatively mild side effects. Liraglutide has been approved for the treatment of diabetes and obesity in the United States, becoming the only drug for these two indications.

However, existing GLP-1 drugs have gastrointestinal side effects. These side effects affect the patient's medication compliance and reduce drug usage as well as user base. According to physiological mechanisms of GLP-1 receptors GLP-1 drugs have a slow effect on weight loss. Clinical treatment of obesity requires the use of higher doses than diabetes treatment, which leads to more severe gastrointestinal side effects. Most patients lose an average of less than 5% body weight, and their body weight rebounds significantly after stopping the medication.

Therefore, there is a clinical need for drugs that can lower blood glucose, decrease blood lipids and body fat content, and reduce body weight simultaneously.

People with diabetes are at higher risk of developing cardiovascular disease. Therefore, people with diabetes need to strictly control blood lipid. Clinical studies have shown that long-term use of statins may increase the risk of users getting diabetes. Statin and fibrate drugs have obvious side effects, and they are intolerant to many patients. There is no therapeutic drug with ideal curative effect for non-alcoholic fatty liver disease. The peptide compounds of the present invention can not only lower blood glucose but also significantly reduce triglyceride and total cholesterol, especially low-density lipoproteins (LDL). They are expected to remedy hyperglycemia and hyperlipidemia at the same time and are expected to have obvious benefits to the user's cardiovascular health. The peptide compounds of the present invention are more suitable for diabetic patients or prediabetic people than statins. The peptide compounds of the present invention provide new options for the treatment of these diseases. The peptides of the present invention are suitable for various diseases caused by abnormal lipid metabolism, including hyperlipidemia and non-alcoholic fatty liver disease. The peptides of the present invention can also be used for diseases such as hypertension, arteriosclerosis, coronary heart disease, peripheral artery disease, stroke, or any combination of these diseases.

The majority of patients with diabetes are middle-aged and elderly people who need to take multiple drugs. This inevitably involves compatibility and matching between drugs. In addition to drug interactions and more toxic side effects resulting from multiple drugs, different drugs have different pharmacokinetics and different dose frequency, which also increases the distress for patients. Therefore, the peptides of the present invention are not only beneficial to enhance the curative effects, mitigate toxicity and side effects, but are also convenient for the patients, thereby improving the therapeutic effects.

The peptides of the present invention can also be used for diabetes treatment like GLP-1 drugs. As these peptides reduce body weight and body fat mass and improve insulin resistance, they should not only have an excellent effect on hyperglycemia but also be particularly effective for a large percentage of diabetic patients who develop diabetes as a result of their excess weight. Although many overweight or obese people are not medically classified as diabetic they have pre-diabetic symptoms such as glucose intolerance and postprandial hyperglycemia. The peptides of the present invention are also suitable for people with pre-diabetes.

SUMMARY OF THE INVENTION

In one aspect, the invention relates to a peptide compound of formula (VII) or a pharmaceutically acceptable salt or solvate thereof, Y-aib-E-G-T-F-X11-S-D-X1-S-X12-X2-L-X3-X4-E-A-X5-X6-X13-F-X7-X8-W-L-X9-A-G-X10 (VII, SEQ ID NO. 220)

wherein X1 is an amino acid selected from L or Y, X2 is an amino acid selected from Q, A, aib or Y, X3 is an amino acid selected from D or E, X4 is an amino acid selected from E or K, and X5 is an amino acid selected from V or A, X6 is an amino acid selected from K, R or Q, X7 is an amino acid selected from I or V, X8 is an amino acid selected from E, Q, N or A, X9 s an amino acid selected from I or L, X10 is absent or is GPSSGAPPP (SEQ ID NO:227), GPPSGAPPP (SEQ ID NO:237), GPSSGKPPP (SEQ ID NO:228), GPSSGEPPP (SEQ ID NO:229), GPSSaibAPPP (SEQ ID NO. 234), GPSSGAPP (SEQ ID NO:230), GPSSGAP (SEQ ID NO:231), GPSSGA (SEQ ID NO:232), GPSSG (SEQ ID NO:233), GPSS (SEQ ID NO:235), GPS (SEQ ID NO:236), GP (SEQ ID NO:238), G; X11 is T or I; X12 is I, S or K; X13 is L, E or D;

Optionally, one or two amino acids selected from S or an amino acid whose side chain contains an amino group or a mercapto group are added to the C-terminus of X10, and the carboxyl group of the C-terminal amino acid is optionally amidated to become the C-terminal amide, said amino acid has the formula (II)

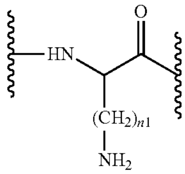

or (III)

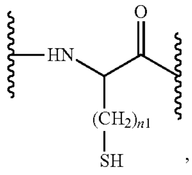

, wherein the wavy line indicates the attachment point to the adjacent group, n1 is an integer of 1-7, when II or III is a C-terminal amino acid, the carboxyl part is COOH or CONH2, preferably, the amino acid containing a side chain amino group is lysine, the amino acid containing a side chain thiol group is cysteine, Optionally, the amino acid at the C-terminus of X10 contains a side chain amino group and this side chain amino group is modified with a long-acting group, preferably, the long-acting group has the structure of formula (IV):

O1-O2-O3-O4-O5-O6-O7-O8- (IV)

wherein O1 has the structure of formula (V) or (VI):

(V)

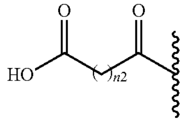

or (VI)

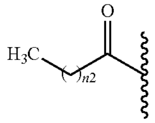

wherein n2 is an integer of 6-24, preferably 10-24, further preferably 16-22; the wavy line indicates the attachment point to the amino group of the adjacent group, and O2-O3-O4-O5-O6-O7-O8- represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, preferably, O2 to O8 contain at least one negatively charged moiety.

In one aspect, the invention relates to a peptide compound of formula (I), or a pharmaceutically acceptable salt or solvate thereof, Y-aib-E-G-T-F-T-S-D-X1-S-I-X2-L-X3-X4-E-A-X5-X6-L-F-X7-X8-W-L-X9-A-G-X10 (I, SEQ ID NO:221)

wherein X1 is an amino acid selected from L or Y, X2 is an amino acid selected from Q, A, aib or Y, X3 is an amino acid selected from D or E, X4 represents an amino acid selected from E or K, and X5 is an amino acid selected from V or A, X6 is an amino acid selected from K or R, X7 is an amino acid selected from I or V, X8 is an amino acid selected from E, A, Q or N, X9 is an amino acid selected from I or L, X10 is absent or is GPSSGAPPP (SEQ ID NO:227), GPPSGAPPP (SEQ ID NO:237), GPSSGKPPP (SEQ ID NO:228), GPSSGEPPP (SEQ ID NO:229), GPSSaibAPPP (SEQ ID NO. 234), GPSSGAPP (SEQ ID NO:230), GPSSGAP (SEQ ID NO:231), GPSSGA (SEQ ID NO:232), GPSSG (SEQ ID NO:233), GPSS (SEQ ID NO:235), GPS (SEQ ID NO:236), GP (SEQ ID NO:238), G;

Optionally, one or two amino acids selected from S or an amino acid whose side chain contains an amino group or a mercapto group are added to the C-terminus of X10, and the carboxyl group of the C-terminal amino acid is optionally amidated to become the C-terminal amide, said amino acid has the formula (II)

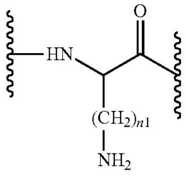

or (III)

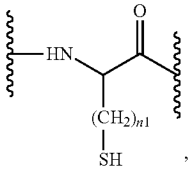

, wherein the wavy line indicates the attachment point to the adjacent group, n1 is an integer of 1-7, when II or III is a C-terminal amino acid, the carboxyl part is COOH or $CONH_2$;

Optionally, the amino acid at the C-terminus of X10 contains a side chain amino group and this side chain amino group is modified with a long-acting group, preferably, the long-acting group has the structure of formula (IV):

O1-O2-O3-O4-O5-O6-O7-O8- (IV)

wherein O1 has the structure of formula (V) or (VI):

(V)

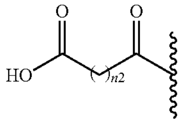

or (VI)

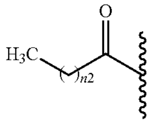

wherein n2 is an integer of 6-24, preferably 10-24, further preferably 16-22; the wavy line indicates the attachment point to the amino group of the adjacent group, and O2-O3-O4-O5-O6-O7-O8- represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, preferably, O2 to O8 contain at least one negatively charged moiety.

The peptide compounds according to any of the preceding aspects, wherein O2-O3-O4-O5-O6-O7-O8- represents a linker selected from the group consisting of γGlu-PEG2-γGlu-, γGlu-PEG2-2xγGlu-, γGlu-PEG2-, γGlu-2xPEG2-, γGlu-3xPEG2-, γGlu-PEG2-γGlu-PEG2-, γGlu-2xPEG2-γGlu-, γGlu-2xPEG2-2xγGlu-, 2xγGlu-, 2xγGlu-PEG2-, 2xγGlu-PEG2-γGlu-, 2xγGlu-PEG2-γGlu-PEG2-, 2xγGlu-2xPEG2-, 2xγGlu-2xPEG2-, 2xγGlu-2xPEG2-γGlu-, and 2xγGlu-2xPEG2-2xγGlu-.

The peptide compounds according to any of the preceding aspects, in some embodiments, wherein O2-O3-O4-O5-O6-O7-O8- represents a linker selected from the group consisting of γGlu-PEG2-, γGlu-2xPEG2-, and γGlu-3xPEG2-, O1 represents the structure of formula (V) or (VI).

The peptide compounds according to any of the preceding aspects, in some embodiments, wherein O2-O3-O4-O5-O6-O7-O8- represents a linker selected from the group consisting of γGlu-PEG2-, γGlu-2xPEG2-, and γGlu-3xPEG2-, O1 represents the structure of formula (V).

The peptide compounds according to any of the preceding aspects, in some embodiments, wherein O2-O3-O4-O5-O6-O7-O8- represents a linker selected from the group consisting of γGlu-2xPEG2-, and γGlu-3xPEG2-, O1 represents the structure of formula (V).

The peptide compounds according to any of the preceding aspects, in some embodiments, wherein O2-O3-O4-O5-O6-O7-O8- represents the linker γGlu-2xPEG2-, and O1 represents the structure of formula (V).

The peptide compounds according to any of the preceding aspects, in some embodiments, wherein O2-O3-O4-O5-O6-O7-O8- represents the linker γGlu-2xPEG2-, and O1 represents the structure of formula (V), wherein n2 is an integer of 16-22.

Optionally, the amino acid at the C-terminus of X10 contains a side chain thiol group which is modified with a long-acting group of formula (IV), optionally, a reactive group capable of reacting with the sulfhydryl group to form a covalent bond can be inserted between the side chain sulfhydryl group of the C-terminal amino acid and the long-acting group as needed.

In some embodiments, the connection relationship between the side chain thiol group of side chain thiol-containing amino acid and the long-acting group is: the side chain thiol group of the amino acid containing a side chain thiol group—thiol reactive group—optional linking group L—long-acting group.

In some embodiments, the side chain thiol group of the amino acid containing a side chain thiol group reacts with a Michael acceptor (e.g. maleimide or vinyl sulfone) or a thiol reactive group (e.g. iodoacetic acid or bromoacetic acid)) and is connected to one end of the linking group L after the reaction, preferably, the other end of the linking group L is further connected to the long-acting group of formula IV via a covalent bond.

In some embodiments, the linking group L is a long chain formed by $-(CH_2)_{n3}-$ and $-(CH_2CH_2O)_{n4}-$ which are arranged and combined according to structural requirements, and are linked together by covalent bonds; or one end or both ends of $-(CH_2)_{n3}-$, $-(CH_2CH_2O)_{n4}$-optionally contain an amino group or a carboxyl group, and are connected by amide bonds to form a long chain, for example, the linking group L is selected from $-NH-(CH_2)_{n5}-(CH_2CH_2O)_{n6}-(CH_2)_{n7}-$, $-NH-(CH_2)_{n5}-(CH_2CH_2O)_{n6}-(CH_2)_{n7}-NH-$, $-NH-(CH_2)_{n5}-(CH_2CH_2O)_{n6}-(CH_2)_{n7}-CO-$, $-NH-(CH_2)_{n5}-(CH_2CH_2O)_{n6}-(CH_2)_{n7}-NHCO-(CH_2)_{n8}-$, $-NH-(CH_2)_{n5}-(CH_2CH_2O)_{n6}-(CH_2)_{n7}-NHCO-(CH_2)_{n8}-NH-$ or any combination thereof, wherein n3, n4, n5, n6, n7, n8 are each an integer of 0 to 10, for example, 0, 1, 2, 3, 4, 5, 6, 7, 8, 9, 10.

In some embodiments, L is $-NH-CH_2-(CH_2CH_2O)_3-(CH_2)_3-NH-$.

In some embodiments, non-limiting illustrative examples of the connection of a Michael reaction acceptor or thiol reactive group to the linking group L include

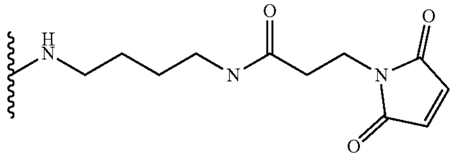

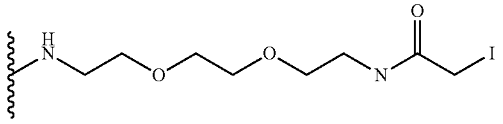

The structures after the reaction of the above exemplary Michael reaction acceptor or thiol reactive group with the side chain thiol group of the amino acid containing a side chain thiol group are as follows:

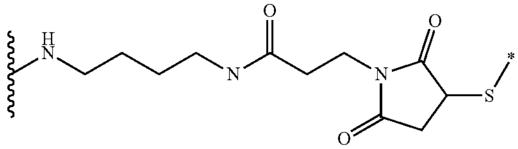

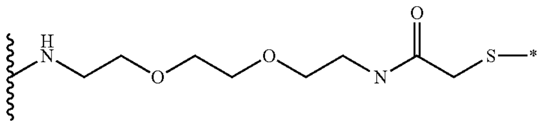

wherein the wavy line is the point of attachment to the long-acting group of formula (IV), for example, to O8. * is the connection point between the side chain thiol group of the amino acid containing a side chain thiol group and the other parts of the amino acid.

Optionally, any one of the amino acids in the peptide fragment represented by X10 may be substituted with an amino acid containing an amino group or a thiol group in its side chain, and the amino acid has the structure of formula (II) or formula (III). Optionally, the amino acid containing a side chain amino group is modified at its side chain amino group with a long-acting group, preferably, the long-acting group has the structure of formula (IV); optionally, the amino acid containing a side chain thiol group is modified at its side chain thiol group with a long-acting group, preferably, the long-acting group has the structure of formula (IV). Optionally, a reactive group capable of reacting with the thiol group to form a covalent bond can be added between the side chain thiol group and the long-acting group as needed.

Optionally, the peptide fragments GPPSGAPPP (SEQ ID NO:237), GPSSGKPPP (SEQ ID NO:228), GPSSGEPPP (SEQ ID NO:229), GPSSaibAPPP (SEQ ID NO. 234) represented by X10 can be reduced by 1, 2, 3, 4, 5, 6, 7, 8 amino acids from the C-terminus of the fragments to the N-terminus of the fragments.

According to a peptide compound of any of the preceding aspects, in some embodiments, X1 is L.

According to a peptide compound of any of the preceding aspects, in some embodiments, X1 is Y.

According to a peptide compound of any of the preceding aspects, in some embodiments, X1 is 1.

According to a peptide compound of any of the preceding aspects, in some embodiments, X1 is V.

According to a peptide compound of any of the preceding aspects, in some embodiments, X2 is Q.

According to a peptide compound of any of the preceding aspects, in some embodiments, X2 is Y.

According to a peptide compound of any of the preceding aspects, in some embodiments, X2 is A.

According to a peptide compound of any of the preceding aspects, in some embodiments, X2 is Aib.

According to a peptide compound of any of the preceding aspects, in some embodiments, X3 is D.

According to a peptide compound of any of the preceding aspects, in some embodiments, X3 is E.

According to a peptide compound of any of the preceding aspects, in some embodiments, X4 is E.

According to a peptide compound of any of the preceding aspects, in some embodiments, X4 is K.

According to a peptide compound of any of the preceding aspects, in some embodiments, X5 is V.

According to a peptide compound of any of the preceding aspects, in some embodiments, X5 is A.

According to a peptide compound of any of the preceding aspects, in some embodiments, X6 is K.

According to a peptide compound of any of the preceding aspects, in some embodiments, X6 is R.

According to a peptide compound of any of the preceding aspects, in some embodiments, X7 is I.

According to a peptide compound of any of the preceding aspects, in some embodiments, X7 is V.

According to a peptide compound of any of the preceding aspects, in some embodiments, X8 is E.

According to a peptide compound of any of the preceding aspects, in some embodiments, X8 is N.

According to a peptide compound of any of the preceding aspects, in some embodiments, X8 is Q.

According to a peptide compound of any of the preceding aspects, in some embodiments, X8 is A.

According to a peptide compound of any of the preceding aspects, in some embodiments, X9 is I.

According to a peptide compound of any of the preceding aspects, in some embodiments, X9 is L.

According to a peptide compound of any of the preceding aspects, in some embodiments, X9 is Aib.

According to a peptide compound of any of the preceding aspects, in some embodiments, X9 is V.

According to a peptide compound of any of the preceding aspects, in some embodiments, X10 is absent. According to a peptide compound of any of the preceding aspects, in some embodiments, X10 is GPSSGAPPPSK (SEQ ID NO:222). According to a peptide compound of any of the preceding aspects, in some embodiments, X10 is GPSSGAPPPSC (SEQ ID NO:223). According to a peptide compound of any of the preceding aspects, in some embodiments, X10 is GPSSGAPPPS (SEQ ID NO:224). According to a peptide compound of any of the preceding aspects, in some embodiments, X10 is GPSSGAPPPK (SEQ ID NO:225). According to a peptide compound of any of the preceding aspects, in some embodiments, X10 is GPSSGAPPPC (SEQ ID NO:226). According to a peptide compound of any of the preceding aspects, in some embodiments, X10 is GPSSGAPPP (SEQ ID NO:227). According to a peptide compound of any of the preceding aspects, in some embodiments, X10 is GPSSGAPP (SEQ ID NO:230). According to a peptide compound of any of the preceding aspects, in some embodiments, X10 is GPSSGAP (SEQ ID NO:231). According to a peptide compound of any of the preceding aspects, in some embodiments, X10 is GPSSGA (SEQ ID NO:232). According to a peptide compound of any of the preceding aspects, in some embodiments, X10 is GPSSG (SEQ ID NO:233). According to a peptide compound of any of the preceding aspects, in some embodiments, X10 is GPSS (SEQ ID NO:235). According to a peptide compound of any of the preceding aspects, in some embodiments, X10 is GPS (SEQ ID NO:236). According to a peptide compound of any of the preceding aspects, in some embodiments, X10 is GP (SEQ ID NO:238). According to a peptide compound of any of the preceding aspects, in some embodiments, X10 is G.

According to a peptide compound of any of the preceding aspects, in some embodiments, X1 is L, and X10 is GPSSGAPPPS (SEQ ID NO:224). According to a peptide compound of any of the preceding aspects, in some embodiments, X1 is L, and X10 is GPSSGAPPPK (SEQ ID NO:225). According to a peptide compound of any of the preceding aspects, in some embodiments, X1 is L, and X10 is GPSSGAPPPC (SEQ ID NO:226). According to a peptide compound of any of the preceding aspects, in some embodiments, X1 is L, and X10 is GPSSGAPPP (SEQ ID NO:227). According to a peptide compound of any of the preceding aspects, in some embodiments, X1 is L, and X10 is GPSSGAPP (SEQ ID NO:230). According to a peptide compound of any of the preceding aspects, in some embodiments, X1 is L, and X10 is GPSSGAP (SEQ ID NO:231). According to a peptide compound of any of the preceding aspects, in some embodiments, X1 is L, and X10 is GPSSGA (SEQ ID NO:232). According to a peptide compound of any of the preceding aspects, in some embodiments, X1 is L, and X10 is GPSSG (SEQ ID NO:233). According to a peptide compound of any of the preceding aspects, in some embodiments, X1 is L, and X10 is GPSS (SEQ ID NO:235). According to a peptide compound of any of the preceding aspects, in some embodiments, X1 is L, and X10 is GPS (SEQ ID NO:236). According to a peptide compound of any of the preceding aspects, in some embodiments, X1 is L, and X10 is GP (SEQ ID NO:238). According to a peptide compound of any of the preceding aspects, in some embodiments, X1 is L, and X10 is G.

According to a peptide compound of any of the preceding aspects, in some embodiments, X2 is Q, and X10 is GPSSGAPPPS (SEQ ID NO:224). According to a peptide compound of any of the preceding aspects, in some embodiments, X2 is Q, and X10 is GPSSGAPPPK (SEQ ID NO:225). According to a peptide compound of any of the preceding aspects, in some embodiments, X2 is Q, and X10 is GPSSGAPPPC (SEQ ID NO:226).

According to a peptide compound of any of the preceding aspects, in some embodiments, X2 is A, and X10 is GPSSGAPPPS (SEQ ID NO:224). According to a peptide compound of any of the preceding aspects, in some embodiments, X2 is A, and X10 is GPSSGAPPPK (SEQ ID NO:225). According to a peptide compound of any of the preceding aspects, in some embodiments, X2 is A, and X10 is GPSSGAPPPC.

According to a peptide compound of any of the preceding aspects, in some embodiments, X2 is aib, and X10 is GPSSGAPPPS (SEQ ID NO:224). According to a peptide compound of any of the preceding aspects, in some embodiments, X2 is aib, and X10 is GPSSGAPPPK (SEQ ID NO:225). According to a peptide compound of any of the preceding aspects, in some embodiments, X2 is aib, and X10 is GPSSGAPPPC (SEQ ID NO:226).

According to a peptide compound of any of the preceding aspects, in some embodiments, X2 is Q, and X10 is GPSSGAPPP (SEQ ID NO:227). According to a peptide compound of any of the preceding aspects, in some embodiments, X2 is Q, and X10 is GPSSGAPP (SEQ ID NO:230). According to a peptide compound of any of the preceding aspects, in some embodiments, X2 is Q, and X10 is GPSSGAP (SEQ ID NO:231). According to a peptide compound of any of the preceding aspects, in some embodiments, X2 is Q, and X10 is GPSSGA (SEQ ID NO:232). According to a peptide compound of any of the preceding aspects, in some embodiments, X2 is Q, and X10 is GPSSG (SEQ ID NO:233). According to a peptide compound of any of the preceding aspects, in some embodiments, X2 is Q, and X10 is GPSS (SEQ ID NO:235). According to a peptide compound of any of the preceding aspects, in some embodiments, X2 is Q, and X10 is GPS (SEQ ID NO:236). According to a peptide compound of any of the preceding aspects, in some embodiments, X2 is Q, and X10 is GP (SEQ ID NO:238). According to a peptide compound of any of the preceding aspects, in some embodiments, X2 is Q, and X10 is G.

According to a peptide compound of any of the preceding aspects, in some embodiments, X2 is A, and X10 is GPSSGAPPP (SEQ ID NO:227). According to a peptide compound of any of the preceding aspects, in some embodiments, X2 is A, and X10 is GPSSGAPP (SEQ ID NO:230). According to a peptide compound of any of the preceding aspects, in some embodiments, X2 is A, and X10 is GPSSGAP (SEQ ID NO:231). According to a peptide compound of any of the preceding aspects, in some embodiments, X2 is A, and X10 is GPSSGA (SEQ ID NO:232). According to a peptide compound of any of the preceding aspects, in some embodiments, X2 is A, and X10 is GPSSG (SEQ ID NO:233). According to a peptide compound of any of the preceding aspects, in some embodiments, X2 is A, and X10 is GPSS (SEQ ID NO:235). According to a peptide compound of any of the preceding aspects, in some embodiments, X2 is A, and X10 is GPS (SEQ ID NO:236). According to a peptide compound of any of the preceding aspects, in some embodiments, X2 is A, and X10 is GP (SEQ ID NO:238). According to a peptide compound of any of the preceding aspects, in some embodiments, X2 is A, and X10 is G.

According to a peptide compound of any of the preceding aspects, in some embodiments, X2 is aib, and X10 is GPSSGAPPP (SEQ ID NO:227). According to a peptide compound of any of the preceding aspects, in some embodiments, X2 is aib, and X10 is GPSSGAPP (SEQ ID NO:230). According to a peptide compound of any of the preceding aspects, in some embodiments, X2 is aib, and X10 is GPSSGAP (SEQ ID NO:231). According to a peptide compound of any of the preceding aspects, in some embodiments, X2 is aib, and X10 is GPSSGA (SEQ ID NO:232). According to a peptide compound of any of the preceding aspects, in some embodiments, X2 is aib, and X10 is GPSSG (SEQ ID NO:233). According to a peptide compound of any of the preceding aspects, in some embodiments, X2 is aib, and X10 is GPSS (SEQ ID NO:235). According to a peptide compound of any of the preceding aspects, in some embodiments, X2 is aib, and X10 is GPS (SEQ ID NO:236). According to a peptide compound of any of the preceding aspects, in some embodiments, X2 is aib, and X10 is GP (SEQ ID NO:238). According to a peptide compound of any of the preceding aspects, in some embodiments, X2 is aib, and X10 is G.

According to a peptide compound of any of the preceding aspects, in some embodiments, X1 is L, and X2 is Q. According to a peptide compound of any of the preceding aspects, in some embodiments, X1 is L, and X2 is A. According to a peptide compound of any of the preceding aspects, in some embodiments, X1 is L, and X2 is aib.

According to a peptide compound of any of the preceding aspects, in some embodiments, X1 is L, X2 is Q, and X10 is GPSSGAPPPS (SEQ ID NO:224). According to a peptide compound of any of the preceding aspects, in some embodiments, X1 is L, X2 is Q, and X10 is GPSSGAPPPK (SEQ ID NO:225). According to a peptide compound of any of the preceding aspects, in some embodiments, X1 is L, X2 is Q, and X10 is GPSSGAPPPC (SEQ ID NO:226). According to a peptide compound of any of the preceding aspects, in some embodiments, X1 is L, X2 is Q, and X10 is GPSSGAPPP (SEQ ID NO:227). According to a peptide compound of any of the preceding aspects, in some embodiments, X1 is L, X2 is Q, and X10 is GPSSGAPP (SEQ ID NO:230). According to a peptide compound of any of the preceding aspects, in some embodiments, X1 is L, X2 is Q, and X10 is GPSSGAP (SEQ ID NO:231). According to a peptide compound of any of the preceding aspects, in some embodiments, X1 is L, X2 is Q, and X10 is GPSSGA (SEQ ID NO:232). According to a peptide compound of any of the preceding aspects, in some embodiments, X1 is L, X2 is Q, and X10 is GPSSG (SEQ ID NO:233). According to a peptide compound of any of the preceding aspects, in some embodiments, X1 is L, X2 is Q, and X10 is GPSS (SEQ ID NO:235). According to a peptide compound of any of the preceding aspects, in some embodiments, X1 is L, X2 is Q, and X10 is GPS (SEQ ID NO:236). According to a peptide compound of any of the preceding aspects, in some embodiments, X1 is L, X2 is Q, and X10 is GP (SEQ ID NO:238). According to a peptide compound of any of the preceding aspects, in some embodiments, X1 is L, X2 is Q, and X10 is G.

According to a peptide compound of any of the preceding aspects, in some embodiments, X1 is L, X2 is A, and X10 is GPSSGAPPPS (SEQ ID NO:224). According to a peptide compound of any of the preceding aspects, in some embodiments, X1 is L, X2 is A, and X10 is GPSSGAPPPK (SEQ ID NO:225). According to a peptide compound of any of the preceding aspects, in some embodiments, X1 is L, X2 is A, and X10 is GPSSGAPPPC (SEQ ID NO:226). According to a peptide compound of any of the preceding aspects, in some embodiments, X1 is L, X2 is A, and X10 is GPSSGAPPP (SEQ ID NO:227). According to a peptide compound of any of the preceding aspects, in some embodiments, X1 is L, X2 is A, and X10 is GPSSGAPP (SEQ ID NO:230). According to a peptide compound of any of the preceding aspects, in some embodiments, X1 is L, X2 is A, and X10 is GPSSGAP (SEQ ID NO:231). According to a peptide compound of any of the preceding aspects, in some embodiments, X1 is L, X2 is A, and X10 is GPSSGA (SEQ ID NO:232). According to a peptide compound of any of the preceding aspects, in some embodiments, X1 is L, X2 is A, and X10 is GPSSG (SEQ ID NO:233). According to a peptide compound of any of the preceding aspects, in some embodiments, X1 is L, X2 is A, and X10 is GPSS (SEQ ID NO:235). According to a peptide compound of any of the preceding aspects, in some embodiments, X1 is L, X2 is A, and X10 is GPS (SEQ ID NO:236). According to a peptide compound of any of the preceding aspects, in some embodiments, X1 is L, X2 is A, and X10 is GP (SEQ ID NO:238). According to a peptide compound of any of the preceding aspects, in some embodiments, X1 is L, X2 is A, and X10 is G.

According to a peptide compound of any of the preceding aspects, in some embodiments, X1 is L, X2 is aib, and X10 is GPSSGAPPPS (SEQ ID NO:224). According to a peptide compound of any of the preceding aspects, in some embodiments, X1 is L, X2 is aib, and X10 is GPSSGAPPPK (SEQ ID NO:225). According to a peptide compound of any of the preceding aspects, in some embodiments, X1 is L, X2 is aib, and X10 is GPSSGAPPPC (SEQ ID NO:226). According to a peptide compound of any of the preceding aspects, in some embodiments, X1 is L, X2 is aib, and X10 is GPSSGAPPP (SEQ ID NO:227). According to a peptide compound of any of the preceding aspects, in some embodiments, X1 is L, X2 is aib, and X10 is GPSSGAPP (SEQ ID NO:230). According to a peptide compound of any of the preceding aspects, in some embodiments, X1 is L, X2 is aib, and X10 is GPSSGAP (SEQ ID NO:231). According to a peptide compound of any of the preceding aspects, in some embodiments, X1 is L, X2 is aib, and X10 is GPSSGA (SEQ ID NO:232). According to a peptide compound of any of the preceding aspects, in some embodiments, X1 is L, X2 is aib, and X10 is GPSSG (SEQ ID NO:233). According to a peptide compound of any of the preceding aspects, in some embodiments, X1 is L, X2 is aib, and X10 is GPSS (SEQ ID NO:235). According to a peptide compound of any of the preceding aspects, in some embodiments, X1 is L, X2 is aib, and X10 is GPS (SEQ ID NO:236). According to a peptide compound of any of the preceding aspects, in some embodiments, X1 is L, X2 is aib, and X10 is GP (SEQ ID NO:238). According to a peptide compound of any of the preceding aspects, in some embodiments, X1 is L, X2 is aib, and X10 is G.

According to a peptide compound of any of the preceding aspects, in some embodiments, X1 is L, X2 is Q, X5 is V, and X10 is GPSSGAPPPS (SEQ ID NO:224). According to a peptide compound of any of the preceding aspects, in some embodiments, X1 is L, X2 is Q, X5 is V, and X10 is GPSSGAPPPK (SEQ ID NO:225). According to a peptide compound of any of the preceding aspects, in some embodiments, X1 is L, X2 is Q, X5 is V, and X10 is GPSSGAPPPC (SEQ ID NO:226).

According to a peptide compound of any of the preceding aspects, in some embodiments, X1 is L, X2 is A, X5 is V, and X10 is GPSSGAPPPS (SEQ ID NO:224). According to a peptide compound of any of the preceding aspects, in some embodiments, X1 is L, X2 is A, X5 is V, and X10 is GPSSGAPPPK (SEQ ID NO:225). According to a peptide compound of any of the preceding aspects, in some embodiments, X1 is L, X2 is A, X5 is V, and X10 is GPSSGAPPPC (SEQ ID NO:226).

According to a peptide compound of any of the preceding aspects, in some embodiments, X1 is L, X2 is aib, X5 is V, and X10 is GPSSGAPPPS. According to a peptide compound of any of the preceding aspects, in some embodiments, X1 is L, X2 is aib, X5 is V, and X10 is GPSSGAPPPK (SEQ ID NO:225). According to a peptide compound of any of the preceding aspects, in some embodiments, X1 is L, X2 is aib, X5 is V, and X10 is GPSSGAPPPC (SEQ ID NO:226).

According to a peptide compound of any of the preceding aspects, in some embodiments, X1 is L, X2 is Q, X3 is E, X5 is V, and X10 is GPSSGAPPPS (SEQ ID NO:224). According to a peptide compound of any of the preceding aspects, in some embodiments, X1 is L, X2 is Q, X3 is E, X5 is V, and X10 is GPSSGAPPPK (SEQ ID NO:225). According to a peptide compound of any of the preceding aspects, in some embodiments, X1 is L, X2 is Q, X3 is E, X5 is V, and X10 is GPSSGAPPPC (SEQ ID NO:226).

According to a peptide compound of any of the preceding aspects, in some embodiments, X1 is L, X2 is A, X3 is E, X5 is V, and X10 is GPSSGAPPPS (SEQ ID NO:224). According to a peptide compound of any of the preceding aspects, in some embodiments, X1 is L, X2 is A, X3 is E, X5 is V, and X10 is GPSSGAPPPK (SEQ ID NO:225). According to a peptide compound of any of the preceding aspects, in some embodiments, X1 is L, X2 is A, X3 is E, X5 is V, and X10 is GPSSGAPPPC (SEQ ID NO:226).

According to a peptide compound of any of the preceding aspects, in some embodiments, X1 is L, X2 is aib, X3 is E, X5 is V, and X10 is GPSSGAPPPS (SEQ ID NO:224). According to a peptide compound of any of the preceding aspects, in some embodiments, X1 is L, X2 is aib, X3 is E, X5 is V, and X10 is GPSSGAPPPK (SEQ ID NO:225). According to a peptide compound of any of the preceding aspects, in some embodiments, X1 is L, X2 is aib, X3 is E, X5 is V, and X10 is GPSSGAPPPC (SEQ ID NO:226).

According to a peptide compound of any of the preceding aspects, in some embodiments, X1 is L, X2 is Q, X3 is E, X4 is K, X5 is V, and X10 is GPSSGAPPPS (SEQ ID NO:224). According to a peptide compound of any of the preceding aspects, in some embodiments, X1 is L, X2 is Q, X3 is E, X4 is K, X5 is V, and X10 is GPSSGAPPPK (SEQ ID NO:225). According to a peptide compound of any of the preceding aspects, in some embodiments, X1 is L, X2 is Q, X3 is E, X4 is K, X5 is V, and X10 is GPSSGAPPPC (SEQ ID NO:226).

According to a peptide compound of any of the preceding aspects, in some embodiments, X1 is L, X2 is A, X3 is E, X4 is K, X5 is V, and X10 is GPSSGAPPPS (SEQ ID NO:224). According to a peptide compound of any of the preceding aspects, in some embodiments, X1 is L, X2 is A, X3 is E, X4 is K, X5 is V, and X10 is GPSSGAPPPK (SEQ ID NO:225). According to a peptide compound of any of the preceding aspects, in some embodiments, X1 is L, X2 is A, X3 is E, X4 is K, X5 is V, and X10 is GPSSGAPPPC (SEQ ID NO:226).

According to a peptide compound of any of the preceding aspects, in some embodiments, X1 is L, X2 is aib, X3 is E, X4 is K, X5 is V, and X10 is GPSSGAPPPS (SEQ ID NO:224). According to a peptide compound of any of the preceding aspects, in some embodiments, X1 is L, X2 is aib, X3 is E, X4 is K, X5 is V, and X10 is GPSSGAPPPK (SEQ ID NO:225). According to a peptide compound of any of the preceding aspects, in some embodiments, X1 is L, X2 is aib, X3 is E, X4 is K, X5 is V, and X10 is GPSSGAPPPC (SEQ ID NO:226).

According to a peptide compound of any of the preceding aspects, in some embodiments, X1 is L, X2 is Q, X3 is E, X4 is K, X5 is V, X7 is I, and X10 is GPSSGAPPPS (SEQ ID NO:224). According to a peptide compound of any of the preceding aspects, in some embodiments, X1 is L, X2 is Q, X3 is E, X4 is K, X5 is V, X7 is I, and X10 is GPSSGAPPPK (SEQ ID NO:225). According to a peptide compound of any of the preceding aspects, in some embodiments, X1 is L, X2 is Q, X3 is E, X4 is K, X5 is V, X7 is I, and X10 is GPSSGAPPPC (SEQ ID NO:226).

According to a peptide compound of any of the preceding aspects, in some embodiments, X1 is L, X2 is A, X3 is E, X4 is K, X5 is V, X7 is I, and X10 is GPSSGAPPPS (SEQ ID NO:224). According to a peptide compound of any of the preceding aspects, in some embodiments, X1 is L, X2 is A, X3 is E, X4 is K, X5 is V, X7 is I, and X10 is GPSSGAPPPK (SEQ ID NO:225). According to a peptide compound of any of the preceding aspects, in some embodiments, X1 is L, X2 is A, X3 is E, X4 is K, X5 is V, X7 is I, and X10 is GPSSGAPPPC (SEQ ID NO:226).

According to a peptide compound of any of the preceding aspects, in some embodiments, X1 is L, X2 is aib, X3 is E, X4 is K, X5 is V, X7 is I, and X10 is GPSSGAPPPS (SEQ ID NO:224). According to a peptide compound of any of the preceding aspects, in some embodiments, X1 is L, X2 is aib, X3 is E, X4 is K, X5 is V, X7 is I, and X10 is GPSSGAPPPK (SEQ ID NO:225). According to a peptide compound of any of the preceding aspects, in some embodiments, X1 is L, X2 is aib, X3 is E, X4 is K, X5 is V, X7 is I, and X10 is GPSSGAPPPC (SEQ ID NO:226).

According to a peptide compound of any of the preceding aspects, in some embodiments, X2 is A and X5 is V. According to a peptide compound of any of the preceding aspects, in some embodiments, X2 is aib and X5 is V.

According to a peptide compound of any of the preceding aspects, in some embodiments, X1 is L, X2 is A, and X5 is V. According to a peptide compound of any of the preceding aspects, in some embodiments, X1 is L, X2 is aib, and X5 is V.

According to a peptide compound of any of the preceding aspects, in some embodiments, X1 is L, X2 is A, X3 is E, and X5 is V. According to a peptide compound of any of the preceding aspects, in some embodiments, X1 is L, X2 is aib, X3 is E, and X5 is V.

According to a peptide compound of any of the preceding aspects, in some embodiments, X1 is L, X2 is A, X3 is E, X4 is K, and X5 is V. According to a peptide compound of any of the preceding aspects, in some embodiments, X1 is L, X2 is aib, X3 is E, X4 is K, and X5 is V.

According to a peptide compound of any of the preceding aspects, in some embodiments, X1 is L, X2 is A, X3 is E, X4 is K, X5 is V, and X7 is I. According to a peptide compound of any of the preceding aspects, in some embodiments, X1 is L, X2 is aib, X3 is E, X4 is K, X5 is V, and X7 is I.

According to a peptide compound of any of the preceding aspects, in some embodiments, X2 is Q and X9 is L. According to a peptide compound of any of the preceding aspects, in some embodiments, X2 is Q, X9 is L, and X10 is GPSSGAPPPS (SEQ ID NO:224). According to a peptide compound of any of the preceding aspects, in some embodiments, X2 is Q, X9 is L, and X10 is GPSSGAPPPK (SEQ ID NO:225). According to a peptide compound of any of the preceding aspects, in some embodiments, X2 is Q, X9 is L, and X10 is GPSSGAPPPC (SEQ ID NO:226).

According to a peptide compound of any of the preceding aspects, in some embodiments, X2 is A and X9 is L. According to a peptide compound of any of the preceding aspects, in some embodiments, X2 is A, X9 is L, and X10 is GPSSGAPPPS (SEQ ID NO:224). According to a peptide compound of any of the preceding aspects, in some embodiments, X2 is A, X9 is L, and X10 is GPSSGAPPPK (SEQ ID NO:225). According to a peptide compound of any of the preceding aspects, in some embodiments, X2 is A, X9 is L, and X10 is GPSSGAPPPC (SEQ ID NO:226).

According to a peptide compound of any of the preceding aspects, in some embodiments, X2 is aib and X9 is L. According to a peptide compound of any of the preceding aspects, in some embodiments, X2 is aib, X9 is L, and X10 is GPSSGAPPPS (SEQ ID NO:224). According to a peptide compound of any of the preceding aspects, in some embodiments, X2 is aib, X9 is L, and X10 is GPSSGAPPPK (SEQ ID NO:225). According to a peptide compound of any of the preceding aspects, in some embodiments, X2 is aib, X9 is L, and X10 is GPSSGAPPPC (SEQ ID NO:226).

According to a peptide compound of any of the preceding aspects, in some embodiments, X1 is L, X2 is Q, X9 is L, and X10 is GPSSGAPPPS (SEQ ID NO:224). According to a peptide compound of any of the preceding aspects, in some embodiments, X1 is L, X2 is Q, X9 is L, and X10 is GPSSGAPPPK (SEQ ID NO:225). According to a peptide compound of any of the preceding aspects, in some embodiments, X1 is L, X2 is Q, X9 is L, and X10 is GPSSGAPPPC (SEQ ID NO:226).

According to a peptide compound of any of the preceding aspects, in some embodiments, X1 is L, X2 is A, X9 is L, and X10 is GPSSGAPPPS (SEQ ID NO:224). According to a peptide compound of any of the preceding aspects, in some embodiments, X1 is L, X2 is A, X9 is L, and X10 is GPSSGAPPPK (SEQ ID NO:225). According to a peptide compound of any of the preceding aspects, in some embodiments, X1 is L, X2 is A, X9 is L, and X10 is GPSSGAPPPC (SEQ ID NO:226).

According to a peptide compound of any of the preceding aspects, in some embodiments, X1 is L, X2 is aib, X9 is L, and X10 is GPSSGAPPPS (SEQ ID NO:224). According to a peptide compound of any of the preceding aspects, in some embodiments, X1 is L, X2 is aib, X9 is L, and X10 is GPSSGAPPPK (SEQ ID NO:225). According to a peptide compound of any of the preceding aspects, in some embodiments, X1 is L, X2 is aib, X9 is L, and X10 is GPSSGAPPPC (SEQ ID NO:226).

According to a peptide compound of any of the preceding aspects, in some embodiments, X1 is L, X2 is Q, X5 is V, X9 is L, and X10 is GPSSGAPPPS (SEQ ID NO:224). According to a peptide compound of any of the preceding aspects, in some embodiments, X1 is L, X2 is Q, X5 is V, X9 is L, and X10 is GPSSGAPPPK (SEQ ID NO:225). According to a peptide compound of any of the preceding aspects, in some embodiments, X1 is L, X2 is Q, X5 is V, X9 is L, and X10 is GPSSGAPPPC (SEQ ID NO:226).

According to a peptide compound of any of the preceding aspects, in some embodiments, X1 is L, X2 is A, X5 is V, X9 is L, and X10 is GPSSGAPPPS (SEQ ID NO:224). According to a peptide compound of any of the preceding aspects, in some embodiments, X1 is L, X2 is A, X5 is V, X9 is L, and X10 is GPSSGAPPPK (SEQ ID NO:225). According to a peptide compound of any of the preceding aspects, in some embodiments, X1 is L, X2 is A, X5 is V, X9 is L, and X10 is GPSSGAPPPC.

According to a peptide compound of any of the preceding aspects, in some embodiments, X1 is L, X2 is aib, X5 is V, X9 is L, and X10 is GPSSGAPPPS (SEQ ID NO:224). According to a peptide compound of any of the preceding aspects, in some embodiments, X1 is L, X2 is aib, X5 is V, X9 is L, and X10 is GPSSGAPPPK (SEQ ID NO:225). According to a peptide compound of any of the preceding aspects, in some embodiments, X1 is L, X2 is aib, X5 is V, X9 is L, and X10 is GPSSGAPPPC (SEQ ID NO:226).

According to a peptide compound of any of the preceding aspects, in some embodiments, X1 is L, X2 is Q, X3 is E, X5 is V, X9 is L, and X10 is GPSSGAPPPS (SEQ ID NO:224). According to a peptide compound of any of the preceding aspects, in some embodiments, X1 is L, X2 is Q, X3 is E, X5 is V, X9 is L, and X10 is GPSSGAPPPK (SEQ ID NO:225). According to a peptide compound of any of the preceding aspects, in some embodiments, X1 is L, X2 is Q, X3 is E, X5 is V, X9 is L, and X10 is GPSSGAPPPC (SEQ ID NO:226).

According to a peptide compound of any of the preceding aspects, in some embodiments, X1 is L, X2 is A, X3 is E, X5 is V, X9 is L, and X10 is GPSSGAPPPS (SEQ ID NO:224). According to a peptide compound of any of the preceding aspects, in some embodiments, X1 is L, X2 is A, X3 is E, X5 is V, X9 is L, and X10 is GPSSGAPPPK (SEQ ID NO:225). According to a peptide compound of any of the preceding aspects, in some embodiments, X1 is L, X2 is A, X3 is E, X5 is V, X9 is L, and X10 is GPSSGAPPPC (SEQ ID NO:226).

According to a peptide compound of any of the preceding aspects, in some embodiments, X1 is L, X2 is aib, X3 is E, X5 is V, X9 is L, and X10 is GPSSGAPPPS (SEQ ID NO:224). According to a peptide compound of any of the preceding aspects, in some embodiments, X1 is L, X2 is aib, X3 is E, X5 is V, X9 is L, and X10 is GPSSGAPPPK (SEQ ID NO:225). According to a peptide compound of any of the preceding aspects, in some embodiments, X1 is L, X2 is aib, X3 is E, X5 is V, X9 is L, and X10 is GPSSGAPPPC (SEQ ID NO:226).

According to a peptide compound of any of the preceding aspects, in some embodiments, X1 is L, X2 is Q, X3 is E, X4 is K, X5 is V, X9 is L, and X10 is GPSSGAPPPS (SEQ ID NO:224). According to a peptide compound of any of the preceding aspects, in some embodiments, X1 is L, X2 is Q, X3 is E, X4 is K, X5 is V, X9 is L, and X10 is GPSSGAPPPK (SEQ ID NO:225). According to a peptide compound of any of the preceding aspects, in some embodiments, X1 is L, X2 is Q, X3 is E, X4 is K, X5 is V, X9 is L, and X10 is GPSSGAPPPC (SEQ ID NO:226).

According to a peptide compound of any of the preceding aspects, in some embodiments, X1 is L, X2 is A, X3 is E, X4 is K, X5 is V, X9 is L, and X10 is GPSSGAPPPS (SEQ ID NO:224). According to a peptide compound of any of the preceding aspects, in some embodiments, X1 is L, X2 is A, X3 is E, X4 is K, X5 is V, X9 is L, and X10 is GPSSGAPPPK (SEQ ID NO:225). According to a peptide compound of any of the preceding aspects, in some embodiments, X1 is L, X2 is A, X3 is E, X4 is K, X5 is V, X9 is L, and X10 is GPSSGAPPPC (SEQ ID NO:226).

According to a peptide compound of any of the preceding aspects, in some embodiments, X1 is L, X2 is aib, X3 is E, X4 is K, X5 is V, X9 is L, and X10 is GPSSGAPPPS (SEQ ID NO:224). According to a peptide compound of any of the preceding aspects, in some embodiments, X1 is L, X2 is aib, X3 is E, X4 is K, X5 is V, X9 is L, and X10 is GPSSGAPPPK (SEQ ID NO:225). According to a peptide compound of any of the preceding aspects, in some embodiments, X1 is L, X2 is aib, X3 is E, X4 is K, X5 is V, X9 is L, and X10 is GPSSGAPPPC (SEQ ID NO:226).

According to a peptide compound of any of the preceding aspects, in some embodiments, X1 is L, X2 is Q, X3 is E, X4 is K, X5 is V, X7 is I, X9 is L, and X10 is GPSSGAPPPS (SEQ ID NO:224).

According to a peptide compound of any of the preceding aspects, in some embodiments, X1 is L, X2 is Q, X3 is E, X4 is K, X5 is V, X7 is I, X9 is L, and X10 is GPSSGAPPPK (SEQ ID NO:225).

According to a peptide compound of any of the preceding aspects, in some embodiments, X1 is L, X2 is Q, X3 is E, X4 is K, X5 is V, X7 is I, X9 is L, and X10 is GPSSGAPPPC (SEQ ID NO:226).

According to a peptide compound of any of the preceding aspects, in some embodiments, X1 is L, X2 is A, X3 is E, X4 is K, X5 is V, X7 is I, X9 is L, and X10 is GPSSGAPPPS (SEQ ID NO:224).

According to a peptide compound of any of the preceding aspects, in some embodiments, X1 is L, X2 is A, X3 is E, X4 is K, X5 is V, X7 is I, X9 is L, and X10 is GPSSGAPPPK (SEQ ID NO:225).

According to a peptide compound of any of the preceding aspects, in some embodiments, X1 is L, X2 is A, X3 is E, X4 is K, X5 is V, X7 is I, X9 is L, and X10 is GPSSGAPPPC (SEQ ID NO:226).

According to a peptide compound of any of the preceding aspects, in some embodiments, X1 is L, X2 is aib, X3 is E, X4 is K, X5 is V, X7 is I, X9 is L, and X10 is GPSSGAPPPS (SEQ ID NO:224).

According to a peptide compound of any of the preceding aspects, in some embodiments, X1 is L, X2 is aib, X3 is E, X4 is K, X5 is V, X7 is I, X9 is L, and X10 is GPSSGAPPPK (SEQ ID NO:225).

According to a peptide compound of any of the preceding aspects, in some embodiments, X1 is L, X2 is aib, X3 is E, X4 is K, X5 is V, X7 is I, X9 is L, and X10 is GPSSGAPPPC (SEQ ID NO:226).

According to a peptide compound of any of the preceding aspects, in some embodiments, X1 is L, X2 is Q, X3 is E, X4 is K, X5 is V, X7 is V, X9 is L, and X10 is GPSSGAPPPS (SEQ ID NO:224).

According to a peptide compound of any of the preceding aspects, in some embodiments, X1 is L, X2 is Q, X3 is E, X4 is K, X5 is V, X7 is V, X9 is L, and X10 is GPSSGAPPPK (SEQ ID NO:225).

According to a peptide compound of any of the preceding aspects, in some embodiments, X1 is L, X2 is Q, X3 is E, X4 is K, X5 is V, X7 is V, X9 is L, and X10 is GPSSGAPPPC (SEQ ID NO:226).

According to a peptide compound of any of the preceding aspects, in some embodiments, X1 is L, X2 is A, X3 is E, X4 is K, X5 is V, X7 is V, X9 is L, and X10 is GPSSGAPPPS (SEQ ID NO:224).

According to a peptide compound of any of the preceding aspects, in some embodiments, X1 is L, X2 is A, X3 is E, X4 is K, X5 is V, X7 is V, X9 is L, and X10 is GPSSGAPPPK (SEQ ID NO:225).

According to a peptide compound of any of the preceding aspects, in some embodiments, X1 is L, X2 is A, X3 is E, X4 is K, X5 is V, X7 is V, X9 is L, and X10 is GPSSGAPPPC (SEQ ID NO:226).

According to a peptide compound of any of the preceding aspects, in some embodiments, X1 is L, X2 is aib, X3 is E, X4 is K, X5 is V, X7 is I, X9 is L, and X10 is GPSSGAPPPS (SEQ ID NO:224).

According to a peptide compound of any of the preceding aspects, in some embodiments, X1 is L, X2 is aib, X3 is E, X4 is K, X5 is V, X7 is V, X9 is L, and X10 is GPSSGAPPPK (SEQ ID NO:225).

According to a peptide compound of any of the preceding aspects, in some embodiments, X1 is L, X2 is aib, X3 is E, X4 is K, X5 is V, X7 is V, X9 is L, and X10 is GPSSGAPPPC (SEQ ID NO:226).

According to a peptide compound of any of the preceding aspects, in some embodiments, X1 is Y and X2 is Q. According to a peptide compound of any of the preceding aspects, in some embodiments, X1 is Y and X2 is A. According to a peptide compound of any of the preceding aspects, in some embodiments, X1 is Y and X2 is Aib. According to a peptide compound of any of the preceding aspects, in some embodiments, X1 is Y and X2 is Y.

According to a peptide compound of any of the preceding aspects, in some embodiments, X4 is K and X9 is L. According to a peptide compound of any of the preceding aspects, in some embodiments, X1 is Y, X4 is K, and X9 is L. According to a peptide compound of any of the preceding aspects, in some embodiments, X1 is Y, X2 is Y, X4 is K, and X9 is L. According to a peptide compound of any of the preceding aspects, in some embodiments, X1 is Y, X2 is Y, X4 is K, X5 is V, and X9 is L. According to a peptide compound of any of the preceding aspects, in some embodiments, X1 is Y, X2 is Y, X3 is E, X4 is K, X5 is V, and X9 is L. According to a peptide compound of any of the preceding aspects, in some embodiments, X1 is Y, X2 is Y, X3 is E, X4 is K, X5 is V, X7 is V, and X9 is L. According to a peptide compound of any of the preceding aspects, in some embodiments, X1 is Y, X2 is Y, X3 is E, X4 is K, X5 is V, X7 is V, X8 is N, and X9 is L. According to a peptide compound of any of the preceding aspects, in some embodiments, X1 is Y, X2 is Y, X3 is E, X4 is K, X5 is V, X7 is V, X8 is N, and X9 is I. A peptide compound according to any of the preceding aspects, in some embodiments, X1 is Y, X2 is Y, X3 is E, X4 is K, X5 is V, X7 is I, X8 is E, and X9 is L.

According to a peptide compound of any of the preceding aspects, in some embodiments, X1 is L and X9 is I. According to a peptide compound of any of the preceding aspects, in some embodiments, X1 is L and X9 is L. According to a peptide compound of any of the preceding aspects, in some embodiments, X1 is L, X2 is Q, and X9 is L. According to a peptide compound of any of the preceding aspects, in some embodiments, X1 is L, X2 is Q, X5 is V, and X9 is L. According to a peptide compound of any of the preceding aspects, in some embodiments, X1 is L, X2 is Q, X3 is E, X5 is V, and X9 is L. According to a peptide compound of any of the preceding aspects, in some embodiments, X1 is L, X2 is Q, X3 is E, X4 is K, X5 is V, and X9 is L. According to a peptide compound of any of the preceding aspects, in some embodiments, X1 is L, X2 is Q, X3 is E, X4 is K, X5 is V, X7 is I, X8 is E, and X9 is L. According to a peptide compound of any of the preceding aspects, in some embodiments, X1 is L and X2 is A. According to a peptide compound of any of the preceding aspects, in some embodiments, X1 is L, X2 is A, and X9 is L. According to a peptide compound of any of the preceding aspects, in some embodiments, X1 is L, X2 is A, X5 is V, and X9 is L. According to a peptide compound of any of the preceding aspects, in some embodiments, X1 is L, X2 is A, X3 is E, X5 is V, and X9 is L. According to a peptide compound of any of the preceding aspects, in some embodiments, X1 is L, X2 is A, X3 is E, X4 is K, X5 is V, and X9 is L. According to a peptide compound of any of the preceding aspects, in some embodiments, X1 is L, X2 is A, X3 is E, X4 is K, X5 is V, X7 is I, X8 is E, and X9 is L. According to a peptide compound of any of the preceding aspects, in some embodiments, X1 is L and X2 is aib. According to a peptide compound of any of the preceding aspects, in some embodiments, X1 is L, X2 is aib, and X9 is L. According to a peptide compound of any of the preceding aspects, in some embodiments, X1 is L, X2 is aib, X5 is V, and X9 is L. According to a peptide compound of any of the preceding aspects, in some embodiments, X1 is L, X2 is aib, X3 is E, X5 is V, and X9 is L. According to a peptide compound of any of the preceding aspects, in some embodiments, X1 is L, X2 is aib, X3 is E, X4 is K, X5 is V, and X9 is L. According to a peptide compound of any of the preceding aspects, in some embodiments, X1 is L, X2 is aib, X3 is E, X4 is K, X5 is V, X7 is I, X8 is E, and X9 is L.

According to a peptide compound of any of the preceding aspects, in some embodiments, X1 is L and X2 is Y. According to a peptide compound of any of the preceding aspects, in some embodiments, X1 is L, X2 is Y, and X5 is V. According to a peptide compound of any of the preceding aspects, in some embodiments, X1 is L, X2 is Y, X3 is E, and X5 is V. According to a peptide compound of any of the preceding aspects, in some embodiments, X1 is L, X2 is Y, X3 is E, X4 is K, and X5 is V.

The peptide compounds according to any of the preceding aspects, wherein the peptide compounds are selected from:

Compound 1: Y(aib)EGTFTSDYSIYLDEEAVRLFVNWLIAGGPSSGAPPPS-$NH_2$ (SEQ ID NO:1);

Compound 2: Y(aib)EGTFTSDYSIYLDEE-AVKLFVNWLIAGGPSSGAPPPS-$NH_2$ (SEQ ID NO:2);

Compound 3: Y(aib)EGTFTSDYSIYLDEE-AVKLFVQWLIAGGPSSGAPPPS-$NH_2$ (SEQ ID NO:3);

Compound 4:

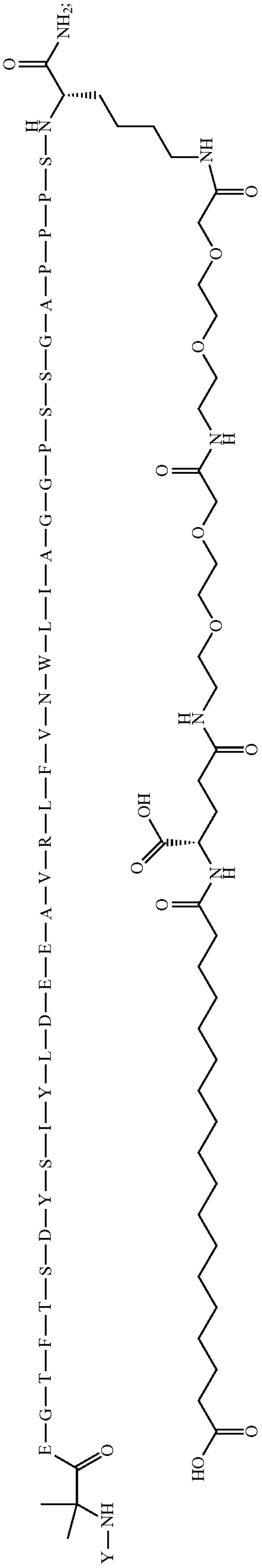
(SEQ ID NO: 4)

Compound 5: Y(aib)EGTFTSDYSIYLDEE-AVRLFVNWLIAGGPSSGAPPPSC-$NH_2$ (SEQ ID NO:5);

Compound 6:

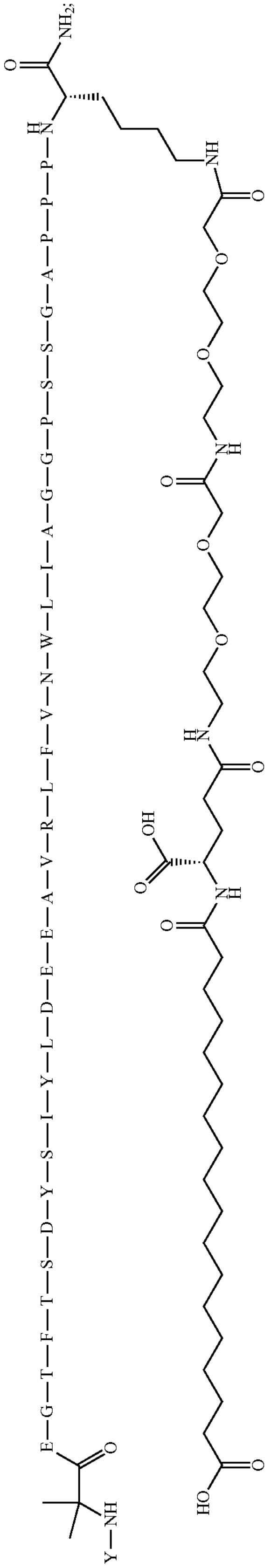
(SEQ ID NO: 6)

Compound 7: Y(aib)EGTFTSDYSIYLDEE-AVKLFVNWLIAG-$NH_2$(SEQ ID NO:7);

Compound 8: Y(aib)EGTFTSDYSIYLEKEAVRLFVNWLIAGGPSSGAPPPS-$NH_2$ (SEQ ID NO:8);

Compound 9: Y(aib)EGTFTSDYSIYLEKEAVKLFVNWLIAGGPSSGAPPPS-$NH_2$ (SEQ ID NO:9);

Compound 10: Y(aib)EGTFTSDYSIYLEKEAAK-LFVNWLIAGGPSSGAPPPS-$NH_2$ (SEQ ID NO: 10);

Compound 11:

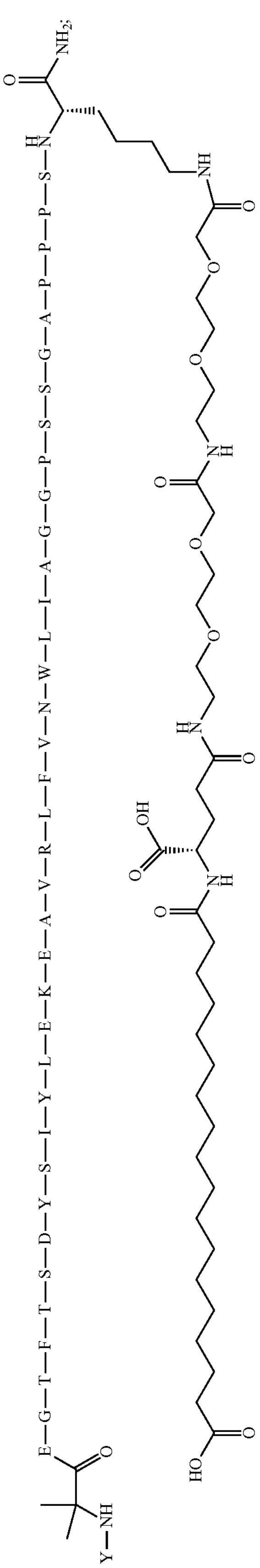
(SEQ ID NO: 11)

Compound 12: Y(aib)EGTFTSDYSIYLEKEAVK LFVNWLIAGGPSSGAPPPK-$NH_2$(SEQ ID NO:12);

Compound 13:

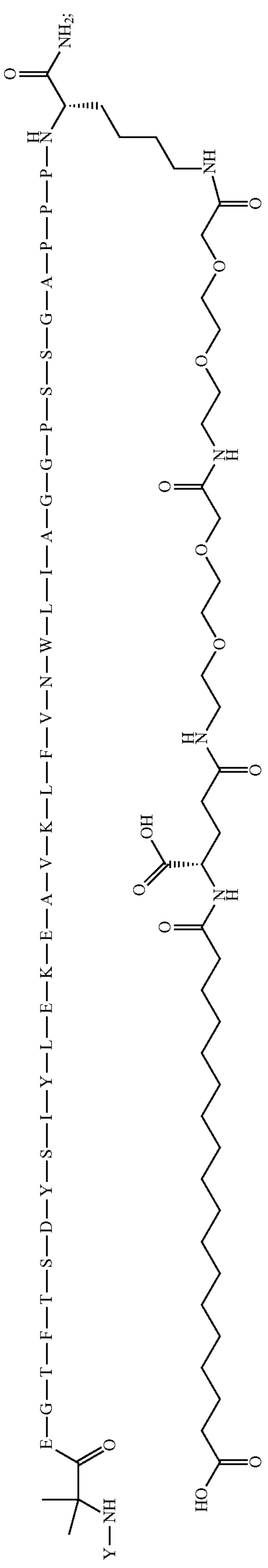
(SEQ ID NO: 13)

Compound 14:

(SEQ ID NO: 14)
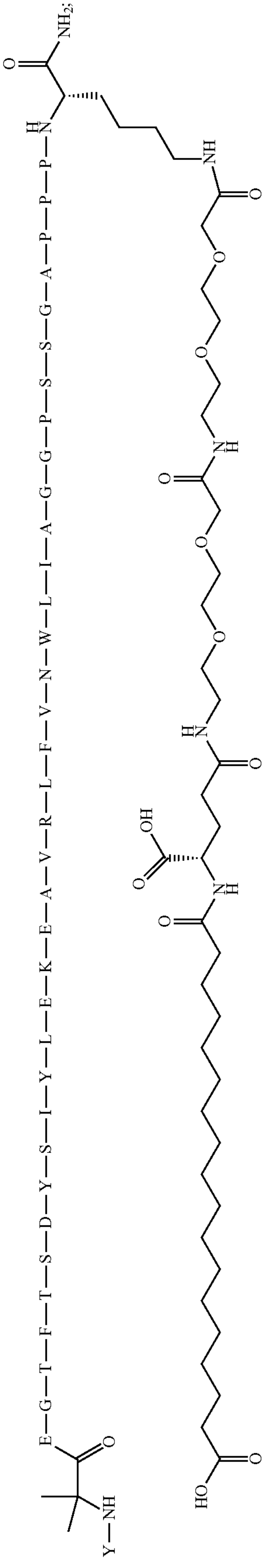

Compound 15: Y(aib) EGTFTSDYSIYLEKEAVRLFVNWLLAG-$NH_2$ (SEQ ID NO:15);

Compound 16: Y(aib) EGTFTSDYSIYLEKEAVRLFIEW-LIAGGPSSGAPPPS-$NH_2$ (SEQ ID NO:16);

Compound 17:

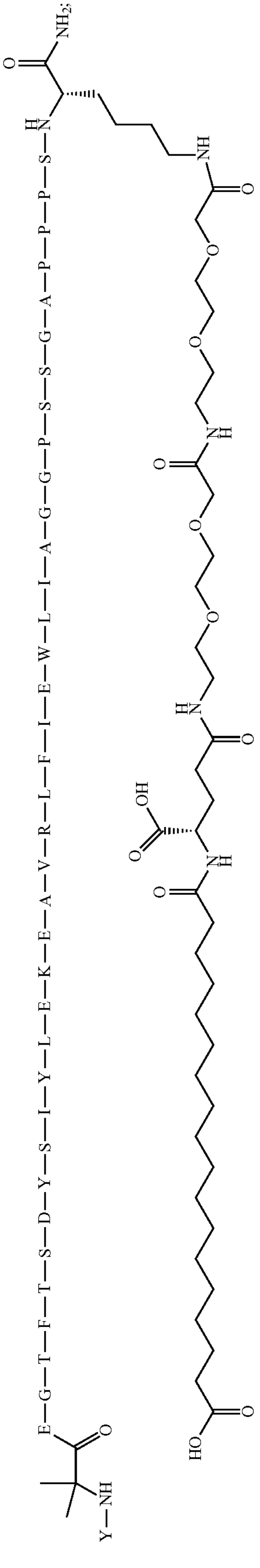
(SEQ ID NO: 17)

Compound 18: Y(aib)EGTFTSDL-SIQLEKEAARLFIEWLLAGGPSSGAPPPS-$NH_2$ (SEQ ID NO:18);

Compound 19: Y(aib)EGTFTSDL-SIQLEKEAVRLFIEWLLAGGPSSGAPPPS-$NH_2$ (SEQ ID NO:19);

Compound 20:

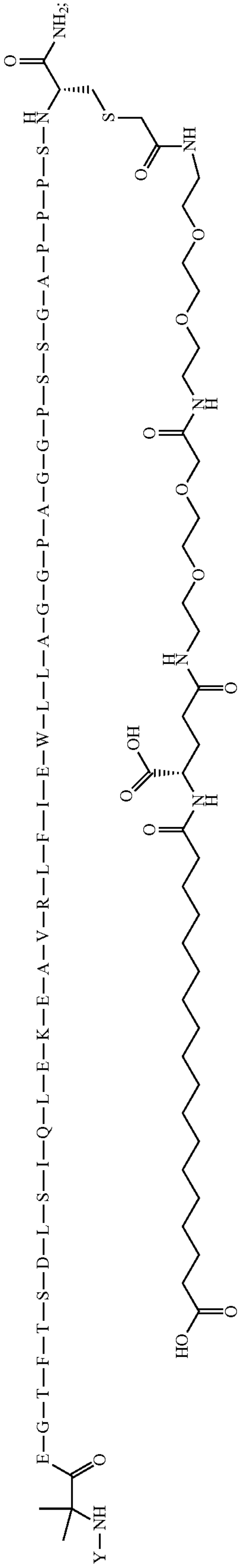
(SEQ ID NO: 20)

Compound 21:

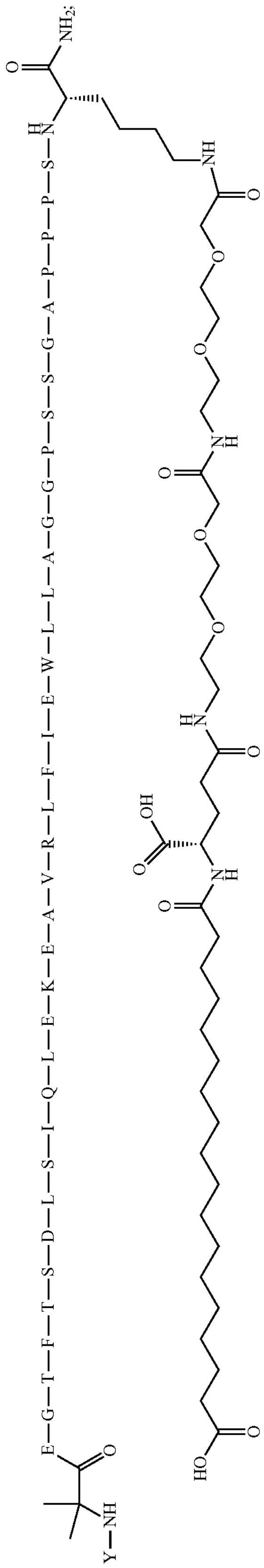
(SEQ ID NO: 21)

Compound 22:

(SEQ ID NO: 22)
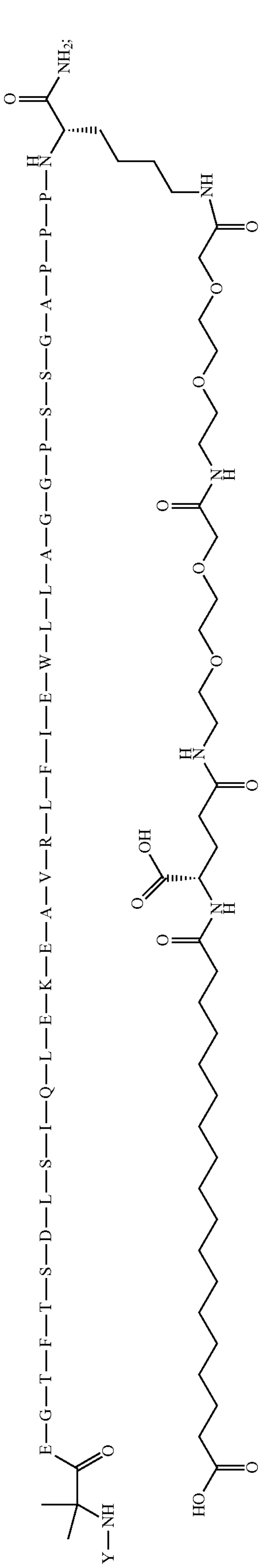

Compound 23:

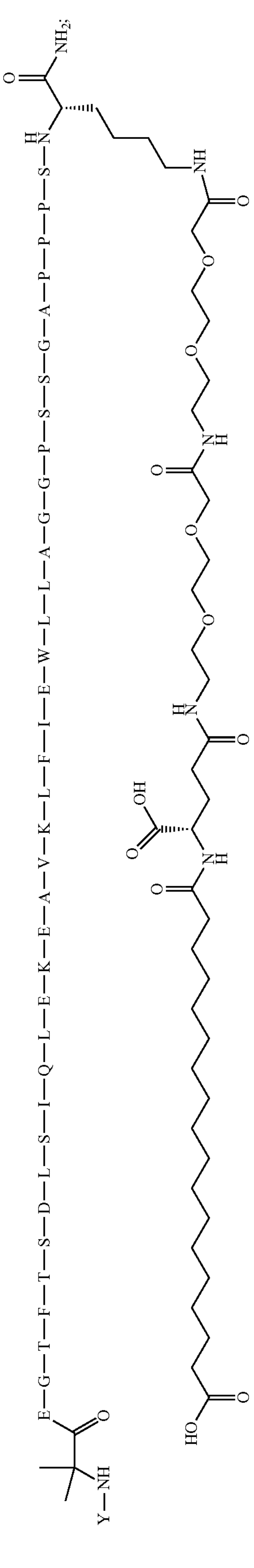
(SEQ ID NO: 23)

Compound 24: Y(aib)EGTFTSDL-SIQLEKEAVKLFIEWLLAGGPSSGAPPPS-$NH_2$ (SEQ ID NO:24);

Compound 25: Y(aib)EGTFTSDL-SIQLEKEAVRLFIEWLLAG-$NH_2$ (SEQ ID NO:25);

Compound 26:

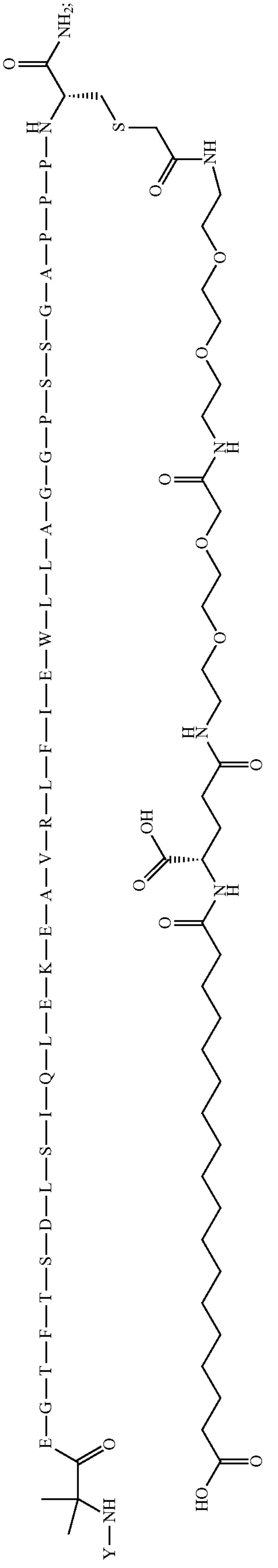
(SEQ ID NO: 26)

Compound 27:

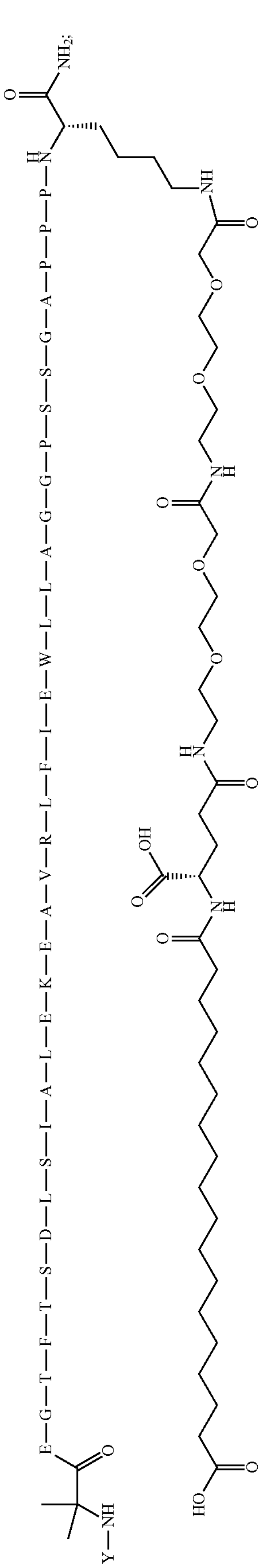
(SEQ ID NO: 27)

Compound 28:

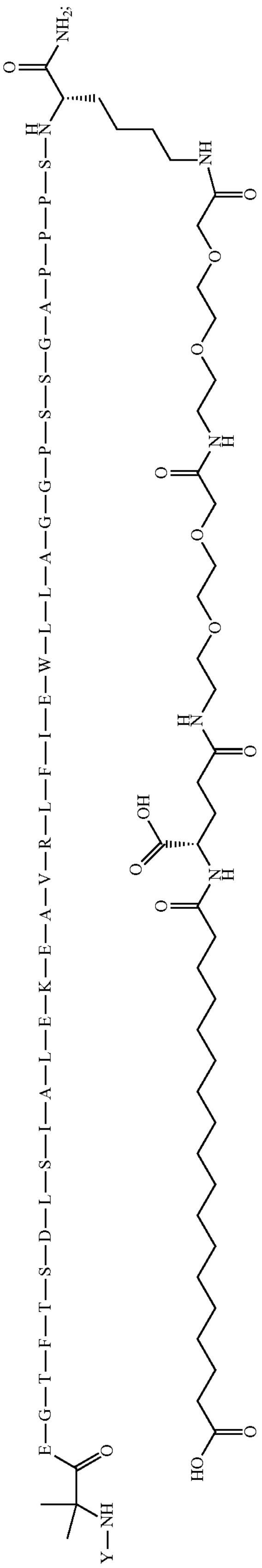
(SEQ ID NO: 28)

Compound 29:

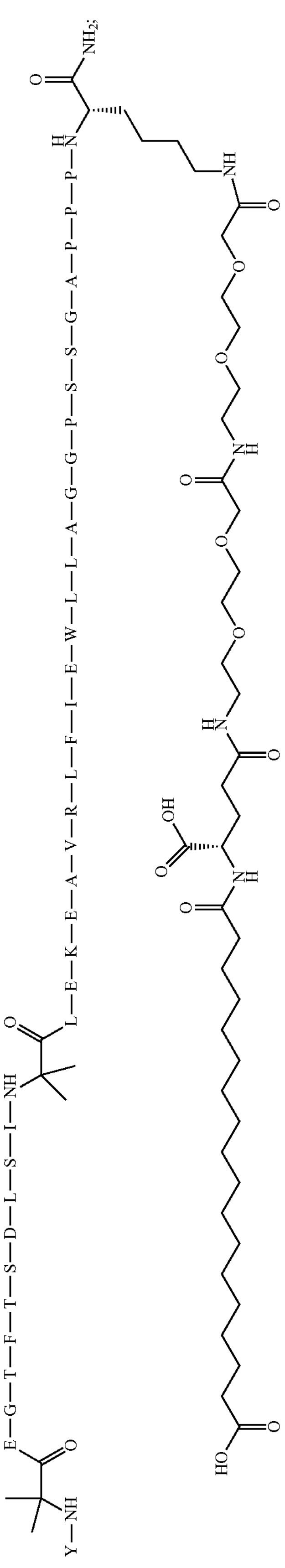
(SEQ ID NO: 29)

Compound 30:

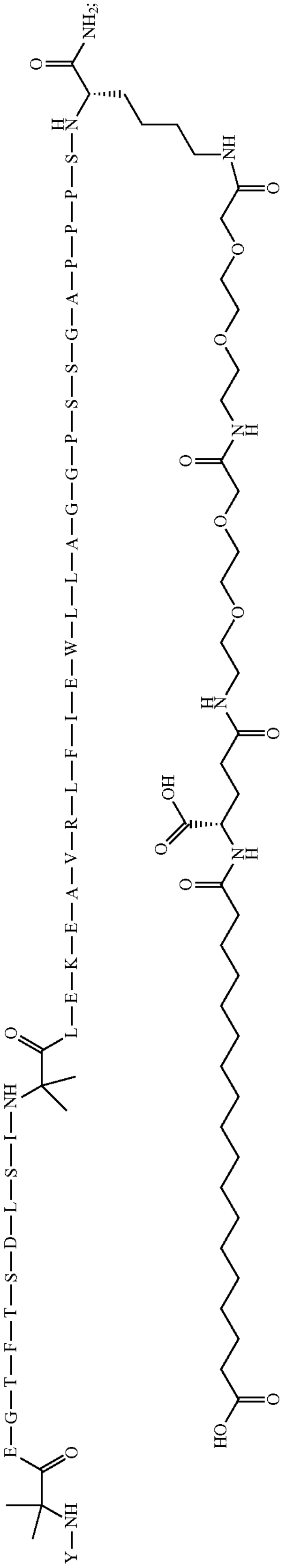
(SEQ ID NO: 30)

Compound 31: Y(aib)EGTFTSDL-SIALEKEAVRLFIEWLLAGGPSSGAPPPS-$NH_2$ (SEQ ID NO:31);

Compound 32: Y(aib)EGTFTSDL-SIALEKEAVRLFIEWLLAGGPSSGAPPPSC-$NH_2$ (SEQ ID NO:32);

Compound 33: Y(aib)EGTFTSDL-SIALEKEAVRLFIEWLLAGGPSSGAPPPC-$NH_2$ (SEQ ID NO:33);

Compound 34: Y(aib)EGTFTSDL-SIALEKEAVRLFIEWLLAGGPSSGAPPPSK-$NH_2$ (SEQ ID NO:34);

Compound 35: Y(aib)EGTFTSDL-SIALEKEAVRLFIEWLLAGGPSSGAPPPK-$NH_2$ (SEQ ID NO:35);

Compound 36: Y(aib)EGTFTSDLSI(aib) LEKEAVRLFIEWLLAGGPSSGAPPPS-$NH_2$ (SEQ ID NO:36);

Compound 37: Y(aib)EGTFTSDLSI(aib) LEKEAVRLFIEWLLAGGPSSGAPPPSC-$NH_2$ (SEQ ID NO:37);

Compound 38: Y(aib)EGTFTSDLSI(aib) LEKEAVRLFIEWLLAGGPSSGAPPPC-$NH_2$ (SEQ ID NO:38);

Compound 39: Y(aib)EGTFTSDLSI(aib) LEKEAVRLFIEWLLAGGPSSGAPPPSK-$NH_2$ (SEQ ID NO:39);

Compound 40: Y(aib)EGTFTSDLSI(aib) LEKEAVRLFIEWLLAGGPSSGAPPPK-$NH_2$ (SEQ ID NO:40);

Compound 41: Y(aib)EGTFTSDL-SIALEKEAVRLFIEWLLAG-$NH_2$(SEQ ID NO:41);

Compound 42: Y(aib)EGTFTSDLSI(aib) LEKEAVRLFIEWLLAG-$NH_2$ (SEQ ID NO:42);

Compound 43; Y(aib)EGTFTSDL-SIALEKEAVKLFIEWLLAGGPSSGAPPPS-$NH_2$ (SEQ ID NO:43);

Compound 44: Y(aib)EGTFTSDL-SIALEKEAVKLFIEWLLAGGPSSGAPPPK-$NH_2$ (SEQ ID NO:44);

Compound 45: Y(aib)EGTFTSDL-SIALEKEAVKLFIEWLLAGGPSSGAPPPSK-$NH_2$ (SEQ ID NO:45);

Compound 46; Y(aib)EGTFTSDL-SIALEKEAVKLFIEWLLAGGPSSGAPPPSC-$NH_2$ (SEQ ID NO:46);

Compound 47: Y(aib)EGTFTSDL-SIALEKEAVKLFIEWLLAGGPSSGAPPPC-$NH_2$ (SEQ ID NO:47);

Compound 48: Y(aib)EGTFTSDLSI(aib) LEKEAVKLFIEWLLAGGPSSGAPPPS-$NH_2$ (SEQ ID NO:48);

Compound 49: Y(aib)EGTFTSDLSI(aib) LEKEAVKLFIEWLLAGGPSSGAPPPK-$NH_2$ (SEQ ID NO:49);

Compound 50: Y(aib)EGTFTSDLSI(aib) LEKEAVKLFIEWLLAGGPSSGAPPPSK-$NH_2$ (SEQ ID NO:50);

Compound 51: Y(aib)EGTFTSDLSI(aib) LEKEAVKLFIEWLLAGGPSSGAPPPC-$NH_2$ (SEQ ID NO:51);

Compound 52: Y(aib)EGTFTSDLSI(aib) LEKEAVKLFIEWLLAGGPSSGAPPPSC-$NH_2$ (SEQ ID NO:52);

Compound 53: Y(aib)EGTFTSDL-SIQLEKEAVRLFVNWLLAGGPSSGAPPPS-$NH_2$ (SEQ ID NO:53);

Compound 54: Y(aib)EGTFTSDL-SIALEKEAVRLFVNWLLAGGPSSGAPPPK-$NH_2$ (SEQ ID NO:54);

Compound 55: Y(aib)EGTFTSDLSI(aib) LEKEAVRLFVNWLLAGGPSSGAPPPC-$NH_2$ (SEQ ID NO:55);

Compound 56: Y(aib)EGTFTSDLSI(aib) LEKEAVRLFVNWLLAGGPSSGAPPPK-$NH_2$ (SEQ ID NO:56);

Compound 57: Y(aib)EGTFTSDYSIYLDEE-AVRLFIEWLIAGGPSSGAPPPK-$NH_2$(SEQ ID NO:57);

Compound 58: Y(aib)EGTFTSDL-SIQLEKEAVRLFVNWLLAGGPSSGAPPPS-$NH_2$ (SEQ ID NO: 58);

Compound 59: Y(aib)EGTFTSDL-SIALEKEAVRLFVNWLLAGGPSSGAPPPS-$NH_2$ (SEQ ID NO:59);

Compound 60: Y(aib)EGTFTSDLSI(aib) LEKEAVRLFVNWLLAGGPSSGAPPPS-$NH_2$ (SEQ ID NO:60);

Compound 61: Y(aib)EGTFTSDYSIYLDEE-AVRLFIEWLIAGGPSSGAPPPS-$NH_2$(SEQ ID NO:61);

Compound 62: Y(aib)EGTFTSDL-SIQLEKEAVRLFIEWLLAGGPSSGAPPPSC-$NH_2$ (SEQ ID NO:62);

Compound 63: Y(aib)EGTFTSDL-SIQLEKEAVRLFIEWLLAGGPSSGAPPPC-$NH_2$ (SEQ ID NO:63);

Compound 64: Y(aib)EGTFTSDL-SIQLEKEAVRLFIEWLLAGGPSSGAPPPSK-$NH_2$ (SEQ ID NO:64);

Compound 65: Y(aib)EGTFTSDL-SIQLEKEAVRLFIEWLLAGGPSSGAPPPK-$NH_2$ (SEQ ID NO:65);

Compound 66: Y(aib)EGTFTSDL-SIQLEKEAVKLFIEWLLAGGPSSGAPPPSC-$NH_2$ (SEQ ID NO:66);

Compound 67: Y(aib)EGTFTSDL-SIQLEKEAVKLFIEWLLAGGPSSGAPPPC-$NH_2$ (SEQ ID NO:67);

Compound 68: Y(aib)EGTFTSDL-SIQLEKEAVKLFIEWLLAGGPSSGAPPPSK-$NH_2$ (SEQ ID NO:68);

Compound 69: Y(aib)EGTFTSDL-SIQLEKEAVKLFIEWLLAGGPSSGAPPPK-$NH_2$ (SEQ ID NO:69);

Compound 70: Y(aib)EGTFTSDYSIYLDEE-AVRLFVNWLIAGGPSSGAPPPSK-$NH_2$ (SEQ ID NO:70);

Compound 71: Y(aib)EGTFTSDYSIYLDEE-AVKLFVNWLIAGGPSSGAPPPSK-$NH_2$ (SEQ ID NO:71);

Compound 72: Y(aib)EGTFTSDYSIYLDEE-AVRLFVNWLIAGGPSSGAPPPK-$NH_2$ (SEQ ID NO:72);

Compound 73: Y(aib)EGTFTSDYSIYLDEE-AVKLFVNWLIAGGPSSGAPPPK-$NH_2$ (SEQ ID NO:73);

Compound 74: Y(aib)EGTFTSDYSIYLDEE-AVKLFVNWLIAGGPSSGAPPPSC-$NH_2$ (SEQ ID NO:74);

Compound 75: Y(aib)EGTFTSDYSIYLDEE-AVRLFVNWLIAGGPSSGAPPPC-$NH_2$(SEQ ID NO:75);

Compound 76: Y(aib)EGTFTSDYSIYLDEE-AVKLFVNWLIAGGPSSGAPPPC-$NH_2$(SEQ ID NO:76);

Compound 77: Y(aib)EGTFTSDYSIYLEKEAVRL FVNWLIAGGPSSGAPPPSK-$NH_2$ (SEQ ID NO:77);

Compound 78: Y(aib)EGTFTSDYSIYLEKEAV KLFVNWLIAGGPSSGAPPPSK-$NH_2$ (SEQ ID NO:78);

Compound 79: Y(aib)EGTFTSDYSIYLEKEAVR LFVNWLIAGGPSSGAPPPK-$NH_2$ (SEQ ID NO:79);

Compound 80: Y(aib)EGTFTSDYSIYLEKEAVRL FVNWLIAGGPSSGAPPPSC-$NH_2$ (SEQ ID NO:80);

Compound 81: Y(aib)EGTFTSDYSIYLEKEAVKL FVNWLIAGGPSSGAPPPSC-$NH_2$ (SEQ ID NO:81);

Compound 82: Y(aib)EGTFTSDYSIYLEKEAVRLF VNWLIAGGPSSGAPPPC-$NH_2$ (SEQ ID NO:82);

Compound 83: Y(aib)EGTFTSDYSIYLEKEAVKLF VNWLIAGGPSSGAPPPC-$NH_2$(SEQ ID NO:83);

Compound 84: Y(aib) EGTFTSDYSIYLEKEAVRLFIEW-LIAGGPSSGAPPPSK-$NH_2$ (SEQ ID NO:84);

Compound 85: Y(aib) EGTFTSDYSIYLEKEAVRLFIEW-LIAGGPSSGAPPPK-$NH_2$ (SEQ ID NO:85);

Compound 86: Y(aib) EGTFTSDYSIYLEKEAVRLFIEW-LIAGGPSSGAPPPSC-$NH_2$ (SEQ ID NO:86);

Compound 87: Y(aib) EGTFTSDYSIYLEKEAVRLFIEW-LIAGGPSSGAPPPC-$NH_2$ (SEQ ID NO:87);

Compound 88: Y(aib) EGTFTSDYSIYLEKEAVRLFIEWLIAG-$NH_2$ (SEQ ID NO:88);

Compound 89: Y(aib)EGTFTSDL-SIQLEKEAVRLFVNWLLAG-$NH_2$ (SEQ ID NO:89);

Compound 90: Y(aib)EGTFTSDL-SIALEKEAVRLFVNWLLAG-$NH_2$ (SEQ ID NO:90);

Compound 91: Y(aib)EGTFTSDLSI(aib) LEKEAVRLFVNWLLAG-$NH_2$(SEQ ID NO:91);

Compound 92: Y(aib)EGTFTSDL-SIQLEKEAVRLFIEWLLAGGPSSGA-$NH_2$ (SEQ ID NO:92);

Compound 93: Y(aib)EGTFTSDYSIYLDEE-AVRLFIEWLIAGGPSSGAPPPS-$NH_2$ (SEQ ID NO:93);

Compound 94: Y(aib)EGTFTSDLSI(aib) LEKEAVRLFIEWLLAGGPSSGAP-$NH_2$ (SEQ ID NO:94);

Compound 95: Y(aib) EGTFTSDYSIYLEKEAVRLFIEWLIAGGPSSGAPP-$NH_2$(SEQ ID NO:95);

Compound 96: Y(aib)EGTFTSDYSIYLDEE-AVRLFVNWLIAGGPSSGAPP-$NH_2$(SEQ ID NO:96);

Compound 97: Y(aib) EGTFTSDYSIYLEKEAVKLFVNWLIAGGPSSGAP-$NH_2$ (SEQ ID NO:97);

Compound 98: Y(aib)EGTFTSDYSIYLEKEAVRLFI-AWLLAGGPSSGAPPPS-$NH_2$(SEQ ID NO:98);

Compound 99: Y(aib)EGTFTSDYSIYLDEE-AVRLFVNWLIAGG-$NH_2$ (SEQ ID NO:99);

Compound 100: Y(aib) EGTFTSDYSIYLEKEAVRLFIEWLIAGGPSSGAP-$NH_2$(SEQ ID NO:100);

Compound 101: Y(aib)EGTFTSDLSKA-LEKEAVRLFIEWLLAGGPSSGAPPPS-$NH_2$ (SEQ ID NO:101);

Compound 102: Y(aib) EGTFTSDYSIYLEKEAVKLFIEW-LIAGGPSSGAPPPS-$NH_2$(SEQ ID NO:102);

Compound 103: Y(aib)EGTFTSDYSIYLDEE-AVRLFVNWLIAGGPSSGA-$NH_2$ (SEQ ID NO:103);

Compound 104: Y(aib)EGTFTSDLSIQLEKEAVKEFI-AWLIAGGPSSGAPPPS-$NH_2$(SEQ ID NO:104);

Compound 105: Y(aib)EGTFTSDYSIYLDEEAVRLFI-AWLIAGGPSSGAPPPS-$NH_2$(SEQ ID NO:105);

Compound 106: Y(aib) EGTFTSDYSIYLEKEAVKLFVNWLIAGG-$NH_2$ (SEQ ID NO:106);

Compound 107: Y(aib)EGTFTSDL-SIALEKEAVRLFVNWLIAGGPSSGAPPPS-$NH_2$ (SEQ ID NO:107);

Compound 108: Y(aib)EGTFTSDYSIYLDEE-AVRLFVNWLIAGGPSSGAP-$NH_2$ (SEQ ID NO:108);

Compound 109: Y(aib) EGTFTSDYSIYLEKEAVKLFVNWLIAGGPSSG-$NH_2$ (SEQ ID NO:109);

Compound 110: Y(aib) EGTFTSDYSIYLEKEAVRLFIEWLIAGGPSSGA-$NH_2$(SEQ ID NO:110);

Compound 111: Y(aib)EGTFTSDL-SIALEKEAVRLFIEWLLAGGPSSGA-$NH_2$ (SEQ ID NO:111);

Compound 112: Y(aib) EGTFTSDYSIYLEKEAVKLFVNWLIAGGP-$NH_2$ (SEQ ID NO:112);

Compound 113: Y(aib)EGTFTSDYSIYLDEE-AVRLFVNWLLAGGPSSGAPPP-$NH_2$(SEQ ID NO:113);

Compound 114: Y(aib)EGTFTSDL-SIQLEKEAVRLFVNWLIAGGPSSGAPPPS-$NH_2$ (SEQ ID NO:114);

Compound 115: Y(aib)EGTFTSDLSI(aib) LEKEAVRLFIEWLLAGGPSSGA-$NH_2$(SEQ ID NO:115);

Compound 116: Y(aib) EGTFTSDYSIYLEKEAVRLFIEWLIAGGPSS-$NH_2$ (SEQ ID NO:116);

Compound 117: Y(aib)EGTFTSDLSIQLEKEAVRLFI-AWLIAGGPSSGAPPPS-$NH_2$(SEQ ID NO:117);

Compound 118: Y(aib) EGTFTSDYSIYLEKEAVKLFVNWL-LAGGPSSGAPPP-$NH_2$ (SEQ ID NO:118);

Compound 119: Y(aib)EGTFTSDL-SIALEKEAVRLFIEWLLAGGPS-$NH_2$ (SEQ ID NO:119);

Compound 120: Y(aib)EGTFTSDYSIYLDEE-AVRLFVNWLIAGGPSS-$NH_2$(SEQ ID NO:120);

Compound 121: Y(aib)EGTFTSDL-SIQLEKEAVRLFIEWLIAGGPSSGAPPP-$NH_2$ (SEQ ID NO:121);

Compound 122: Y(aib)EGTFTSDYSIYLDEE-AVRLFVNWLIAGGP-$NH_2$ (SEQ ID NO:122);

Compound 123: Y(aib) EGTFTSDYSIYLEKEAVRLFIEWL-LAGGPSSGAPPP-$NH_2$ (SEQ ID NO:123);

Compound 124: Y(aib)EGTFTSDL-SIQLEKEAVRLFIEWLLAGG-$NH_2$ (SEQ ID NO:124);

Compound 125: Y(aib)EGTFTSDL-SIQLEKEAVKLFIEWLIAGGPSSGAPPP-$NH_2$(SEQ ID NO:125);

Compound 126: Y(aib)EGTFTSDYSIYLEKEAVKLFI-AWLIAGGPSSGAPPPS-$NH_2$(SEQ ID NO:126);

Compound 127: Y(aib)EGTFTSDLSIALEKEAVRLFI-AWLIAGGPSSGAPPPS-$NH_2$ (SEQ ID NO:127);

Compound 128: Y(aib)EGTFTSDL-SIQLEKEAVKLFIEWLLAGGPSSGAPP-$NH_2$(SEQ ID NO:128);

Compound 129: Y(aib)EGTFTSDYSIYLEKEAVKEFI-AWLLAGGPSSGAPPP-$NH_2$ (SEQ ID NO:129);

Compound 130: Y(aib)EGTFTSDL-SIQLEKEAVRLFIEWLLAGGP-$NH_2$ (SEQ ID NO:130);

Compound 131: Y(aib)EGTFTSDL-SIQLEKEAVKLFIEWLLAGGPSSGAP-$NH_2$(SEQ ID NO:131);

Compound 132: Y(aib) EGTFTSDYSIYLEKEAVKLFVNWLIAGGPSSGA-$NH_2$ (SEQ ID NO:132);

Compound 133: Y(aib)EGTFISDL-SIALEKEAVRLFIEWLLAGGPSSGAPPPS-$NH_2$ (SEQ ID NO:133);

Compound 134: Y(aib) EGTFTSDYSIYLEKEAVRLFIEWLIAGGP-$NH_2$ (SEQ ID NO:134);

Compound 135: Y(aib) EGTFTSDYSIYLEKEAVKLFVNWLIAGGPSS-$NH_2$ (SEQ ID NO:135);

Compound 136: Y(aib)EGTFTSDLSI(aib)LEKEAVKE-FIAWLLAGGPSSGAPPPS-$NH_2$ (SEQ ID NO:136);

Compound 137: Y(aib)EGTFTSDL-SIQLEKEAVKLFIEWLLAGGPSSGA-$NH_2$ (SEQ ID NO:137);

Compound 138: Y(aib)EGTFTSDL-SIALEKEAVRLFIEWLLAGGPSSG-$NH_2$(SEQ ID NO:138);

Compound 139: Y(aib)EGTFTSDYSIYLDEE-AVRLFVNWLIAGGPS-$NH_2$ (SEQ ID NO:139);

Compound 140: Y(aib)EGTFTSDL-SIQLEKEAVRLFIEWLLAGGPSS-$NH_2$(SEQ ID NO:140);

Compound 141: Y(aib) EGTFTSDYSIYLEKEAVKLFVNWLIAGGPSSGAPP-$NH_2$(SEQ ID NO:141);

Compound 142: Y(aib)EGTFTSDL-SIALEKEAVRLFIEWLLAGGPSSGAP-$NH_2$(SEQ ID NO:142);

Compound 143: Y(aib)EGTFTSDL-SIQLEKEAVKLFIEWLLAGGPSSG-$NH_2$ (SEQ ID NO:143);

Compound 144: Y(aib)EGTFTSDY-SIALEKEAVRLFIEWLLAGGPSSGAPPPS-$NH_2$ (SEQ ID NO:144);

Compound 145: Y(aib)EGTFTSDL-SIQLEKEAVKLFIEWLLAGGPSS-$NH_2$ (SEQ ID NO:145);

Compound 146: Y(aib)EGTFTSDL-SIQLEKEAVRLFIEWLLAGGPSSG-$NH_2$(SEQ ID NO:146);

Compound 147: Y(aib)EGTFISDLSI(aib) LEKEAVRLFIEWLLAGGPSSGAPPPS-$NH_2$ (SEQ ID NO:147);

Compound 148: Y(aib) EGTFTSDYSIYLEKEAVRLFIEWLIAGGPSSG-$NH_2$ (SEQ ID NO:148);

Compound 149: Y(aib)EGTFTSDYSIYLEKEAVKEFI-AWLIAGGPSSGAPPPS-$NH_2$ (SEQ ID NO:149);

Compound 150: Y(aib)EGTFTSDLSI(aib) LEKEAVRLFIEWLLAGGPSSGAPP-$NH_2$(SEQ ID NO:150);

Compound 151: Y(aib)EGTFTSDLSIYLDEE-AVRLFVNWLLAGGPSSGAPPPS-$NH_2$ (SEQ ID NO:151);

Compound 152: Y(aib)EGTFTSDL-SIALEKEAVRLFIEWLLAGGP-$NH_2$ (SEQ ID NO:152);

Compound 153: Y(aib)EGTFTSDL-SIQLEKEAVKLFIEWLLAGGPS-$NH_2$ (SEQ ID NO:153);

Compound 154: Y(aib)EGTFTSDL-SIQLEKEAVRLFIEWLLAGGPSSGAPP-$NH_2$ (SEQ ID NO:154);

Compound 155: Y(aib) EGTFTSDYSIYLEKEAVRLFIEWLIAGG-$NH_2$ (SEQ ID NO:155);

Compound 156: Y(aib)EGTFTSDL-SIQLEKEAVKLFIEWLLAGGP-$NH_2$(SEQ ID NO:156);

Compound 157: Y(aib)EGTFTSDL-SIALEKEAVQDFVNWLIAGGPSSGAPPPS-$NH_2$ (SEQ ID NO:157);

Compound 158: Y(aib)EGTFTSDL-SIQLEKEAVRLFIEWLLAGGPS-$NH_2$(SEQ ID NO:158);

Compound 159: Y(aib)EGTFTSDLSIYLDEE-AVRLFVNWLLAGGPSSGAP-$NH_2$ (SEQ ID NO:159);

Compound 160: Y(aib)EGTFTSDL-SIALEKEAVRLFIEWLLAGGPSSGAPPP-$NH_2$ (SEQ ID NO:160);

Compound 161: Y(aib)EGTFTSDLSI(aib)LEKEAVRL-FIAWLLAGGPSSGAPPPS-$NH_2$ (SEQ ID NO:161);

Compound 162: Y(aib)EGTFTSDYSIQLDEE-AVRLFVNWLLAGGPSSGAPPPS-$NH_2$ (SEQ ID NO:162);

Compound 163: Y(aib)EGTFTSDLSIALEKEAVKEFI-AWLIAGGPSSGAPPPS-$NH_2$(SEQ ID NO:163);

Compound 164: Y(aib) EGTFTSDYSIYLEKEAVRLFIEWLIAGGPS-$NH_2$ (SEQ ID NO:164)

Compound 165: Y(aib)EGTFTSDYSIYLDEE-AVRLFVNWLIAGGPSSG-$NH_2$ (SEQ ID NO:165);

Compound 166: Y(aib)EGTFTSDLSI(aib) LEKEAVQDFVNWLLAGGPSSGAPPPS-$NH_2$ (SEQ ID NO:166);

Compound 167: Y(aib)EGTFTSDL-SIYLEKEAVKLFVNWLLAGGPSSGAP-$NH_2$(SEQ ID NO:167);

Compound 168: Y(aib)EGTFTSDLSK(aib) LEKEAVRLFIEWLLAGGPSSGAPPP-$NH_2$ (SEQ ID NO:168);

Compound 169: Y(aib)EGTFTSDYSIYLDEEAVKEFI-AWLIAGGPSSGAPPPS-$NH_2$(SEQ ID NO:169);

Compound 170: Y(aib)EGTFTSDL-SIYLEKEAVRLFIEWLLAGGPSSGAPP-$NH_2$ (SEQ ID NO:170);

Compound 171: Y(aib)EGTFTSDYSIALDEE-AVRLFVNWLLAGGPSSGAPPPS-$NH_2$ (SEQ ID NO:171);

Compound 172: Y(aib)EGTFTSDLSIALEKEAVKLFVNWLLAGGPSSGAPPPS-$NH_2$ (SEQ ID NO:172);

Compound 173: Y(aib)EGTFTSDLSIYLEKEAVRLFIEWLLAGGPSSGAP-$NH_2$ (SEQ ID NO:173);

Compound 174: Y(aib)EGTFTSDLSI(aib)LEKEAVRLFIEWLLAGG-$NH_2$ (SEQ ID NO:174);

Compound 175: Y(aib)EGTFTSDLSIYLEKEAVKLFVNWLLAGGPSSGA-$NH_2$(SEQ ID NO:175);

Compound 176: Y(aib)EGTFTSDLSIYLDEEAVRLFVNWLLAGGPS-$NH_2$ (SEQ ID NO:176);

Compound 177: Y(aib)EGTFTSDLSIYLDEEAVRLFVNWLLAGGPSSGAPPP-$NH_2$ (SEQ ID NO:177);

Compound 178: Y(aib)EGTFTSDLSI(aib)LEKEAVRLFIEWLLAGGPS-$NH_2$(SEQ ID NO:178);

Compound 179: Y(aib)EGTFTSDLSIALEKEAVRLFIEWLLAGGPSSGAPP-$NH_2$ (SEQ ID NO:179);

Compound 180: Y(aib)EGTFTSDLSIYLEKEAVKLFVNWLLAGGPSSG-$NH_2$(SEQ ID NO:180);

Compound 181: Y(aib)EGTFTSDLSI(aib)LEKEAVRLFIEWLLAGGPSSG-$NH_2$(SEQ ID NO:181);

Compound 182: Y(aib)EGTFTSDYSIQLEKEAVRLFIEWLLAGGPSSGAPPPS-$NH_2$ (SEQ ID NO:182);

Compound 183: Y(aib)EGTFTSDLSIYLEKEAVKLFVNWLLAGGPSSGAPPP-$NH_2$ (SEQ ID NO:183);

Compound 184: Y(aib)EGTFTSDLSI(aib)LEKEAVRLFIEWLLAGGPSS-$NH_2$(SEQ ID NO:184);

Compound 185: Y(aib)EGTFTSDLSIYLDEEAVRLFVNWLLAGGPSSGA-$NH_2$ (SEQ ID NO:185);

Compound 186: Y(aib)EGTFTSDYSI(aib)LEKEAVRLFIEWLLAGGPSSGAPPPS-$NH_2$ (SEQ ID NO:186);

Compound 187: Y(aib)EGTFTSDLSIALEKEAVRLFIEWLLAGG-$NH_2$ (SEQ ID NO:187) Compound 188: Y(aib)EGTFTSDLSIQLEKEAVRLFIEWLLAGGPSSGAP-$NH_2$(SEQ ID NO:188);

Compound 189: Y(aib)EGTFTSDYSIYLEKEAVKLFVNWLIAGGPS-$NH_2$ (SEQ ID NO:189);

Compound 190: Y(aib)EGTFTSDLSIYLEKEAVRLFIEWLLAGGPSSGAPPPS-$NH_2$ (SEQ ID NO:190);

Compound 191: Y(aib)EGTFTSDLSI(aib)LEKEAVRLFVNWLLAGGPSSGAPPPS-$NH_2$ (SEQ ID NO:191);

Compound 192: Y(aib)EGTFTSDLSIYLDEEAVRLFVNWLLAGGPSSG-$NH_2$ (SEQ ID NO:192);

Compound 193: Y(aib)EGTFTSDLSIYLEKEAVKLFVNWLLAGGPS-$NH_2$ (SEQ ID NO:193);

Compound 194: Y(aib)EGTFTSDLSIYLDEEAVRLFVNWLLAGGPSS-$NH_2$ (SEQ ID NO:194);

Compound 195: Y(aib)EGTFTSDLSK(aib)LEKEAVRLFIEWLLAGGPSSGAPPPS-$NH_2$ (SEQ ID NO:195);

Compound 196: Y(aib)EGTFTSDLSIYLEKEAVRLFIEWLLAGGPSSG-$NH_2$(SEQ ID NO:196);

Compound 197: Y(aib)EGTFTSDLSIYLEKEAVKLFVNWLLAGGPSSGAPP-$NH_2$(SEQ ID NO:197);

Compound 198: Y(aib)EGTFTSDLSIYLEKEAVRLFIEWLLAGGPS-$NH_2$(SEQ ID NO:198);

Compound 199: Y(aib)EGTFTSDLSI(aib)LEKEAVRLFIEWLLAGGP-$NH_2$(SEQ ID NO:199);

Compound 200: Y(aib)EGTFTSDLSIYLEKEAVRLFIEWLLAGGP-$NH_2$ (SEQ ID NO:200);

Compound 201: Y(aib)EGTFTSDLSIYLDEEAVRLFVNWLLAGG-$NH_2$ (SEQ ID NO:201);

Compound 202: Y(aib)EGTFTSDLSIYLEKEAVKLFVNWLLAGGPSSGAPPPS-$NH_2$ (SEQ ID NO:202);

Compound 203: Y(aib)EGTFTSDLSIYLEKEAVRLFIEWLLAGGPSS-$NH_2$(SEQ ID NO:203);

Compound 204: Y(aib)EGTFTSDLSIYLDEEAVRLFVNWLLAGGP-$NH_2$(SEQ ID NO:204);

Compound 205: Y(aib)EGTFTSDLSIYLEKEAVKLFVNWLLAGGPSS-$NH_2$ (SEQ ID NO:205);

Compound 206: Y(aib)EGTFTSDLSIQLEKEAVKLFIEWLLAGG-$NH_2$(SEQ ID NO:206);

Compound 207: Y(aib)EGTFTSDYSIYLEKEAVRLFIEWLLAGGPSSGAPPP-$NH_2$ (SEQ ID NO:207);

Compound 208: Y(aib)EGTFTSDLSIYLEKEAVKLFVNWLLAGGP-$NH_2$ (SEQ ID NO:208);

Compound 209: Y(aib)EGTFTSDLSIYLEKEAVRLFIEWLLAGGPSSGAPPP-$NH_2$ (SEQ ID NO:209);

Compound 210: Y(aib)EGTFTSDLSI(aib)LEKEAVRLFIEWLLAGGPSSGAPPP-$NH_2$ (SEQ ID NO:210);

Compound 211: Y(aib)EGTFTSDLSIYLEKEAVRLFIEWLLAGGPSSGA-$NH_2$ (SEQ ID NO:211);

Compound 212: Y(aib)EGTFTSDLSIYLEKEAVKLFVNWLLAGG-$NH_2$(SEQ ID NO:212);

Compound 213: Y(aib)EGTFTSDYSI(aib)LDEEAVRLFVNWLLAGGPSSGAPPPS-$NH_2$ (SEQ ID NO:213);

Compound 214: Y(aib)EGTFTSDLSIALEKEAVRLFIEWLLAGGPSS-$NH_2$(SEQ ID NO:214);

Compound 215: Y(aib)EGTFTSDLSIYLDEEAVRLFVNWLLAGGPSSGAPP-$NH_2$(SEQ ID NO:215);

Compound 216: Y(aib)EGTFTSDLSI(aib)LEKEAVKLFVNWLLAGGPSSGAPPPS-$NH_2$ (SEQ ID NO:216);

Compound 217: Y(aib)EGTFTSDLSSALEKEAVRLFIEWLLAGGPSSGAPPPK-$NH_2$ (SEQ ID NO:217);

Compound 218: Y(aib)EGTFTSDLSIYLEKEAVRLFIEWLLAGG-$NH_2$ (SEQ ID NO:218);

and Compound 219: Y(aib)EGTFTSDL-SIQLEKEAVKLFVNWLLAGGPSSGAPPPS-$NH_2$ (SEQ ID NO:219).

The peptide compounds according to any of the preceding aspects, wherein the peptide compounds contain only natural amino acids.

In one aspect, the invention relates to a pharmaceutical composition comprising a peptide compound or a pharmaceutically acceptable salt or solvate of any of the preceding aspects, and a pharmaceutically acceptable carrier or excipient thereof.

In one aspect, the invention relates to methods of treating or preventing the following diseases or conditions: impaired glucose tolerance (IGT), hyperglycemia, type 1 diabetes, type 2 diabetes, obesity, metabolic syndrome and neurodegenerative diseases, especially for delaying or preventing disease progression in type 2 diabetes, delaying the progression from impaired glucose tolerance to type 2 diabetes; delaying the progression from type 2 diabetes to diabetes requiring insulin; treating metabolic syndrome, regulating appetite, inducing satiety, reducing food intake, increasing energy expenditure, treating obesity or preventing overweight; preventing weight rebound after successful weight loss; treating diseases or conditions associated with overweight or obesity; treating bulimia; treating binge eating; treating blood lipid abnormality, atherosclerosis, hypertension, coronary heart disease, β-blocker poisoning; treating non-alcoholic fatty liver disease (NAFLD) (which can be divided into simple fatty liver (SFL), non-alcoholic steatohepatitis (NASH) and its associated cirrhosis); inhibiting gastrointestinal motility, for use in conjunction with gastrointestinal investigation techniques such as X-ray, CT, and NMR scanning; the method comprises administering to the patient an effective amount of the peptide compound or a pharmaceutically acceptable salt or solvate of any of the preceding aspects or a pharmaceutical composition thereof.

In one aspect, the present invention relates to the use of the peptide compound or the pharmaceutically acceptable salt or solvate or the pharmaceutical composition thereof in any one of the preceding aspects in the preparation of a medicament for reducing blood glucose or treating diabetes.

In one aspect, the present invention relates to the use of the peptide compound or the pharmaceutically acceptable salt or solvate or the pharmaceutical composition thereof in any one of the preceding aspects in the preparation of a medicament for weight loss.

In one aspect, the present invention relates to the use of the peptide compound or the pharmaceutically acceptable salt or solvate or the pharmaceutical composition of any one of the preceding aspects in the preparation of a medicament for reducing blood lipids, preferably reducing the blood lipid components selected from the following: cholesterol, triglycerides, free fatty acids, low density lipoprotein; more preferably, reducing low density lipoprotein cholesterol.

In one aspect, the present invention relates to a method for preparing a peptide compound according to any one of the foregoing aspects, wherein the preparation method is a chemical synthesis method.

The inventors made a series of structural modifications to the peptide derivatives of GLP-1 receptor agonists, including selecting specific amino acids, or introducing new amino acids at the C-terminus of peptides, or replacing the C-terminal amino acid residues of peptides, and the unique long-acting groups are linked to peptides through either the side chain thiol group of cysteine residue or the side chain amino group of lysine residue at the C-terminus of peptides to obtain a series of new peptide compounds. Unexpected technical effects have been achieved.

DETAILED DESCRIPTION

Figure 1:
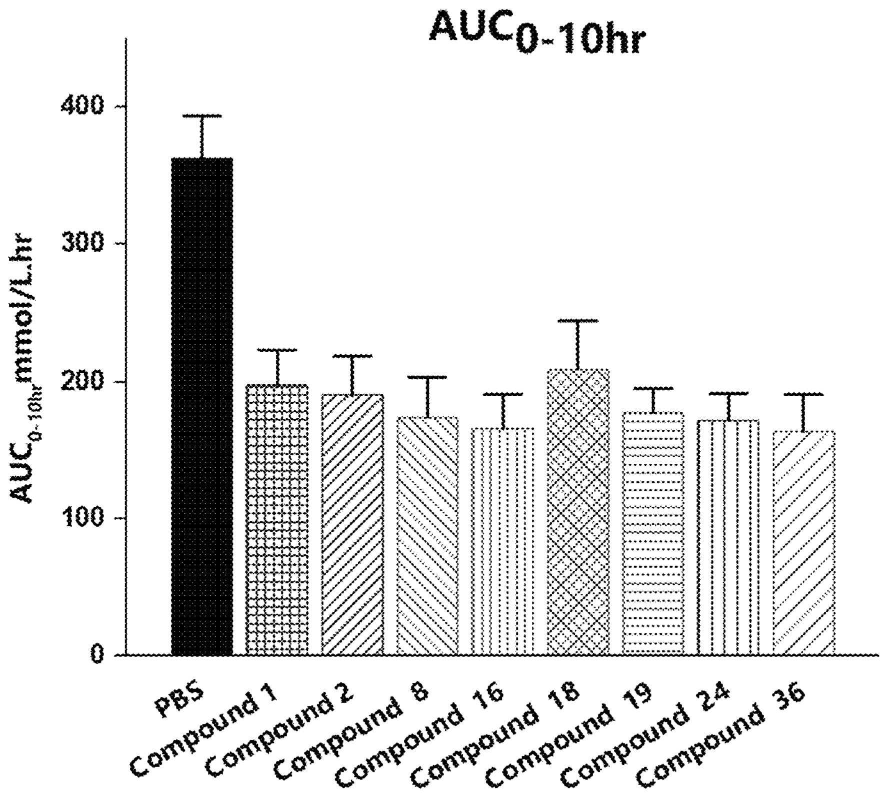
FIG. 1: Tests of compounds 1, 2, 8, 16, 18, 19, 24 and 36 of the present invention to lower blood glucose in db/db mice.

Unless otherwise stated, the following definitions apply throughout the present invention. Undefined terms can be understood in accordance with conventional definitions in the industry.

"Amino acid" refers to a molecule containing both amino and carboxyl functional groups, and the amino and carboxyl groups of an α-amino acid are attached to the same carbon atom (a carbon). The alpha carbon may have 1-2 additional organic substituents. Amino acids include L and D isomers and racemic mixtures. Unless otherwise specified, the amino acid residues in the peptide sequence of the present invention are all L isomers, that is, L-amino acids, and D-amino acids are indicated by a lowercase letter "d" before the amino acid name or abbreviation, such as dK.

The amino acid sequences of the present invention contain the conventional one-letter or three-letter codes for naturally occurring amino acids, as well as the generally recognized three-letter codes for other amino acids, such as Tic (1,2,3,4-tetrahydroisoquinoline-3-carboxylic acid), Aib (α-aminoisobutyric acid) or GABA (γ-aminobutyric acid). The abbreviated codes of commonly used molecular structures include:

hGlu is homoglutamic acid;

α-hGlu is the L isomer of —HNCH(CO—)$CH_2CH_2CH_2COOH$;

δ-hGlu is the L isomer of —HNCH(COOH)$CH_2CH_2CH_2CO$—;

α-Glu is the L isomer of —HNCH(CO—)$CH_2CH_2COOH$;

γ-Glu or gGlu is the L isomer of —HNCH(COOH)$CH_2CH_2CO$—;

α-Asp is the L isomer of —HNCH(CO—)$CH_2$COOH;

β-Asp is the L isomer of —HNCH(COOH)$CH_2$CO—;

β-Ala is —HN—$CH_2$—$CH_2$—COOH;

PEG2 is 2-(2-(2-aminoethoxy)ethoxy)acetic acid (CAS No. 134978-97-5).

The amino acid composition of a peptide in the present invention can be changed without substantially affecting its biological activity. For example, a peptide sequence may contain one or more conservative amino acid substitutions. Conservative amino acid substitution is the substitution of one amino acid residue with another amino acid residue with a similar side chain. In the literature, amino acid residues are classified according to the nature of their side chains. Amino acid residues containing basic side chains include lysine, arginine, and histidine; amino acid residues containing acidic side chains and amide side chains include aspartic acid, glutamic acid, asparagine, and glutamine; amino acid residues containing small aliphatic, non-polar or weakly polar side chains include glycine, alanine, threonine, serine, and proline; amino acid residues containing large aliphatic, non-polar side chains include leucine, isoleucine, and valine; amino acid residues with aromatic side chains include phenylalanine, tryptophan, and tyrosine; amino acid residues with sulfur-containing side chains include cysteine and methionine.

In some embodiments, the derivative comprises a substituent containing a lipophilic moiety and an optional 1-3 negatively charged moiety, wherein one of the negatively charged moieties is distal to the lipophilic moiety. In some embodiments, the substituent is attached to the side chain of the C-terminal amino acid of the sequence. If the C-terminus of the sequence is lysine it is attached to the ε amino group of the lysine residue.

As used herein, "expression vector" includes a vector capable of expressing DNA that is operably linked to, for example, regulatory sequences in a promoter region that can affect the expression of such DNA fragments. Such additional fragments may include promoter and terminator sequences, and may optionally include one or more origins of replication, one or more selection markers, enhancers, polyadenylation signals, etc. Expression vectors are generally derived from plasmid or viral DNA, or may contain elements of both. Thus, expression vector refers to a recombinant DNA or RNA construct, such as a plasmid, a bacteriophage, a recombinant virus, or other vectors, which leads to the expression of cloned DNA when introduced into an appropriate host cell. Suitable expression vectors are well known to those skilled in the art, and include expression vectors that can be replicated in eukaryotic cells and/or prokaryotic cells as well as expression vectors that remain free or are integrated into the genome of the host cell. In one embodiment, when the compound contains genetically encoded amino acid residues, the invention further provides a nucleic acid (which may be DNA or RNA) encoding the compound, a vector containing such nucleic acid, as well as a host cell containing such nucleic acid or expression vector.

As used herein, the term "treatment" includes inhibiting, slowing, stopping, or reversing the progress or severity of existing symptoms of patients. Therefore, treatment includes prevention, treatment, and/or cure. Prevention refers to preventing the underlying disease and/or preventing the deterioration of symptoms or the development of the disease.

As used herein, "efficacy" means an effect caused by an individual's treatment that changes, usually improves or ameliorates the symptoms of the disease or disease condition, or cures the disease or disease condition.

As used herein, "therapeutically effective amount" or "therapeutically effective dose" refers to an amount of a substance, compound, material, or composition containing a compound that is at least sufficient to produce a therapeutic effect after administration to a subject. Therefore, it is the amount necessary to prevent, cure, ameliorate, block or partially block the symptoms of a disease or condition.

As used herein, "prophylactically effective amount" or "prophylactically effective dose" refers to the amount of a substance, compound, material, or composition containing a compound that will have the desired prophylactic effect when administered to a subject, for example, to prevent or delay occurrence or recurrence of disease or symptom, reduce the possibility of the occurrence or recurrence of disease or symptoms. Completely prophylactically effective doses do not have to occur through the administration of one dose, and may only occur after the administration of a series of doses. Therefore, the prophylactically effective amount can be administered in one or more applications.

As used herein, the term "patient" refers to a mammal, such as a human.

Holst (Holst, JJ Physiol. Rev. 2007, 87, 1409) and Meier (Meier, JJ Nat. Rev. Endocrinol. 2012, 8, 728) describe GLP-1 receptor agonists, such as GLP-1, liraglutide and exendin-4.

Certain compounds of the present invention are generally effective over a wide dosage range. For example, the dose administered once a week may be in the range of about 0.05 to about 30 mg per person per week. Certain compounds of the invention can be administered daily. In addition, certain compounds of the present invention can be administered once a week.

It should be understood that the therapeutic agent according to the embodiments will be administered together with pharmaceutically acceptable carriers, excipients, and other agents which are incorporated into the formulation to provide improved transfer, delivery, tolerance, etc. Many suitable formulations can be found in the pharmacopoeia known to all medicinal chemists: Remington's Pharmaceuticals (15th edition, Mack Publishing, Easton, Pa. (1975)), in particular Chapter 87 by Blaug and Seymour. These formulations include, for example, powders, pastes, ointments, gels, waxes, oils, lipids, lipid-containing (cationic or anionic) carriers (such as Lipofectin™), DNA conjugates, anhydrous slurries, oil-in-water and water-in-oil emulsions, polyethylene glycols (polyethylene glycols of various molecular weights) emulsion, semi-solid gels, and semi-solid mixtures containing polyethylene glycol. Any of the foregoing mixtures may be suitable for treatment or therapy according to the present invention, provided that the active ingredients in the formulation are not inactivated by the formulation and the formulation is physiologically compatible and tolerates the route of administration.

As used herein, the term "pharmaceutically acceptable carrier" is intended to include any and all solvents, dispersion media, coatings, antibacterial and antifungal agents, isotonic and absorption delaying agents, etc. that are compatible with drug administration. Suitable carriers are described in the latest edition of Remington's Pharmaceutical Sciences, which is a standard bibliography in the art, which is incorporated herein by reference. Preferred examples of such carriers or diluents include, but are not limited to water, saline, Ringer's solution, glucose solution, and 5% human serum albumin. Liposomes and non-aqueous carriers, such as immobilized oil, can also be used. The use of such media and agents for pharmaceutically active substances is well known in the art.

The preparations to be used for clinical in vivo administration must be sterile. This can be easily achieved by filtration through a sterile filter.

The compounds of the present invention can react with a variety of inorganic or organic acids to form pharmaceutically acceptable acid addition salts. Pharmaceutically acceptable salts and common methods for preparing them are well known in the art. Refer to, for example, Handbook of Pharmaceutical Salts: Properties, Selection, and Use. Second revision (Wiley-VCH, 2011); S. M. Berge et al. "Pharmaceutical Salts", Journal of Pharmaceutical Sciences, Vol. 66, No. 1, January 1977. Commonly used pharmaceutically acceptable salts include trifluoroacetate, acetate, citrate, hydrochloride, etc.

The pharmaceutical compositions of the embodiments are formulated to be compatible with their intended routes of administration. Examples of administration routes include parenteral, such as intravenous, intradermal, subcutaneous, oral (e.g. inhalation), transdermal (e.g. topical), transmucosal, and rectal administration. Solutions or suspensions for parenteral, intradermal or subcutaneous administration may include the following components: sterile diluents for injection, such as water, saline solutions, fixed oils, polyethylene glycols, glycerin, propylene glycol or other synthetic solvents; antibacterial agents, such as benzyl alcohol, methyl 4-hydroxybenzoate, phenol, or m-cresol; antioxidants, such as ascorbic acid or sodium bisulfite; chelating agents, such as ethylenediaminetetraacetic acid (EDTA); buffers, such as acetates, citrates or phosphates, and agents that regulate osmotic pressure, such as sodium chloride or dextrose. pH can be adjusted with acids or bases, such as hydrochloric acid or sodium hydroxide. The parenteral preparation can be packaged in ampoules, penicillin vials, disposable syringes, multi-dose glass or plastic vials or injection pens. There are two major types of injection pens. One is a disposable pre-filled pen, which contains medicine and can be thrown away after use without changing the cartridge; the other is a more commonly used durable injection pen. It includes an injector and a medicine cartridge. This type of injection pens can be used again after replacing the cartridge.

Pharmaceutical compositions suitable for injection include sterile aqueous solutions (herein water-soluble) or dispersions and sterile powders for immediate preparation of sterile injectable solutions or dispersions. For intravenous administration, suitable carriers include saline, bacteriostatic water, Cremophor EL™ (BASF, Parsippany, N.J.) or phosphate buffered saline (PBS). In all cases, the compositions must be sterile, and their fluidity should make injection easy. The compositions must be stable under manufacturing and storage conditions and must be able to prevent contamination by microorganisms such as bacteria and fungi. The carrier can be a solvent or dispersion medium containing, for example, water, ethanol, polyol (e.g. glycerin, propylene glycol, and liquid polyethylene glycol, etc.), and suitable mixtures thereof. A desired particle size can be maintained in the case of dispersion, for example, by using a coating such as lecithin, and, proper fluidity can be maintained by using a surfactant. Prevention of microorganisms can be achieved by various antibacterial and antifungal agents such as parabens, chlorobutanol, phenol, m-cresol, ascorbic acid, thimerosal, etc. In many cases, it is preferable to include isotonic agents in the compositions, such as sugars, polyols (e.g. mannitol, sorbitol), and sodium chloride. Prolonged absorption of the composition for injection can be achieved by including in the composition an agent that delays absorption, such as aluminum monostearate and gelatin.

If desired, a sterile injectable solution can be prepared by incorporating a required amount of the compound of the present invention in a suitable solvent with one or a combination of ingredients listed above (as required), followed by filtration and sterilization. In general, dispersions are prepared by incorporating the compounds of this invention into sterile vehicles that contain a dispersion medium and those required other ingredients listed above. In the case of sterile powders for the preparation of sterile injectable solutions, the methods of preparation are vacuum drying and freeze-drying of the powders, which contains the active ingredients and any additional desired ingredients from the aforementioned sterile filtered solutions of these ingredients.

For administration by inhalation, the compound is delivered in the form of an aerosol spray from a pressurized container or dispenser or nebulizer containing a suitable propellant gas such as carbon dioxide.

It can also be administered systemically by transmucosal or transdermal methods. For transmucosal or transdermal administration, penetrants suitable for penetrating barriers are used in the formulations. Such penetrants are generally known in the art and include, for example, detergents, bile salts and fusidic acid derivatives for transmucosal administration. Transmucosal administration can be achieved through the use of nasal sprays or suppositories. For transdermal administration, one or more of the compounds of the present invention may be formulated as plasters, ointments, gels, or creams as generally known in the art.

The compounds can also be prepared in the form of suppositories (e.g. with conventional suppository bases such as cocoa butter or other glycerides) or retentive enemas for transrectal delivery.

In one embodiment, the compounds of the present invention can be prepared with carriers that prevent their rapid elimination by the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparing such formulations are obvious to those skilled in the art.

For instance, these active ingredients can be encapsulated in microcapsules prepared, for example, by coacervation technique or by interfacial polymerization, for example, hydroxymethyl cellulose or gelatin microcapsules and poly (methyl methacrylate) microcapsules, respectively, in colloidal drug delivery systems (e.g. liposomes, albumin microspheres, microemulsions, nanoparticles, and nanocapsules) or in macroemulsions.

Sustained release formulations can be prepared. Examples of suitable sustained-release preparations include semipermeable matrices of solid hydrophobic polymers containing the compounds of the present invention, and the matrices are in the form of shaped articles such as films or microcapsules. Examples of sustained-release matrices include polyester, hydrogel (e.g. poly(2-hydroxyethyl-methyl propionate), or poly(vinyl alcohol)), polylactide (U.S. Pat. No. 3,773,919), copolymers of L-glutamic acid and γ-ethyl-L-glutamate, non-degradable ethylene-vinyl acetate, degradable lactic acid-glycolic acid copolymers such as LUPRON DEPOT™ (injection microspheres composed of lactic acid-glycolic acid copolymer and leuprorelin acetate), and poly-D-(−)-3-hydroxybutyric acid. Although polymers made from, for example, ethylene-vinyl acetate and lactic acid-glycolic acid can release molecules for more than 100 days some hydrogels release proteins for a shorter time. Polylactic acid (PLA) and polylactic acid-glycolic acid copolymer (PLGA)

have been the focus of research in recent years. In addition, there are albumin microspheres, chitosan microspheres, gelatin microspheres, etc.

Liposomal suspensions can also be used as pharmaceutically acceptable carriers. These can be prepared according to methods known to those skilled in the art, such as description in U.S. Pat. No. 4,522,811.

It is especially advantageous to formulate parenteral compositions in the form of dosage unit for ease of administration and uniformity of dosage. As used herein, a dosage unit refers to a physically separable unit which is suitable as a unit dose for the subject to be treated; Each unit contains a predetermined amount of one or more of the compounds of the present invention calculated in combination with the required pharmaceutical carrier to produce the desired therapeutic effects. The specifications of the dosage unit of the embodiment are indicated by and directly dependent on: the unique characteristics of the compounds of the present invention and the specific therapeutic effects to be achieved, and the limitations inherent in the formulations of such compounds of the present invention for personalized treatment.

The pharmaceutical composition can be placed in a container, package, or dispenser together with instructions for administration.

The present invention provides a method for treating type 2 diabetic patients, comprising administering an effective amount of a compound or a pharmaceutically acceptable salt of the present invention to patients in need of such treatment. The present invention also provides a method for treating type 2 diabetic patients, comprising administering to patients in need of such treatment an effective amount of a compound or a pharmaceutically acceptable salt of the present invention, wherein the administration is subcutaneous. The present invention also provides a method for treating type 2 diabetic patients, comprising administering an effective amount of a compound or a pharmaceutically acceptable salt of the present invention to patient in need of such treatment, and administering the effective amount simultaneously, separately, or sequentially with one or more other active ingredients. In one embodiment, the other one or more active ingredients are currently available oral glucose-lowering drugs that are considered the standard of care prior to administration (as determined by industry guidelines from, for example, the American Diabetes Association).

The present invention also provides methods for treating or preventing the following diseases or conditions: impaired glucose tolerance (IGT), hyperglycemia, type 1 diabetes, type 2 diabetes, obesity, metabolic syndrome, and neurodegenerative diseases, especially for delaying or preventing disease progression in type 2 diabetes, delaying progression from impaired glucose tolerance to type 2 diabetes; delaying progression from type 2 diabetes to insulin-requiring diabetes; treating metabolic syndrome, regulating appetite, inducing satiety, reducing food intake, increasing energy expenditure, treating obesity or preventing overweight; preventing weight rebound after successful weight loss; treating diseases or conditions related to overweight or obesity; treating bulimia; treating binge eating; treating dyslipidemia, atherosclerosis, hypertension, coronary heart disease, β-blocker poisoning; treating non-alcoholic fatty liver disease (NAFLD) (can be divided into simple fatty liver (SFL), non-alcoholic Steatohepatitis (NASH) and its associated cirrhosis); inhibiting gastrointestinal motility, for use in conjunction with gastrointestinal investigation techniques such as X-ray, CT, and NMR scanning. The method includes administering an effective amount of a compound or a pharmaceutically acceptable salt or solvate of the present invention to patients in need of such treatment, and administering the effective amount simultaneously, separately, or sequentially with one or more other active ingredients.

Further preferred medical uses include treatment or prevention of degenerative disorders, particularly neurodegenerative disorders such as Alzheimer's disease, Parkinson's disease, Huntington's disease, ataxia (e.g spinocerebellar ataxia), Kennedy disease, myotonic dystrophy, Lewy body dementia, multi-systemic atrophy, amyotrophic lateral sclerosis, primary lateral sclerosis, spinal muscular atrophy, prion-associated diseases (e.g. Creutzfeldt-Jacob disease), multiple sclerosis, telangiectasia, Batten disease, corticobasal degeneration, subacute combined degeneration of spinal cord, Tabes dorsalis, Tay-Sachs disease, toxic encephalopathy, infantile Refsum disease, Refsum disease, neuroacanthocytosis, Niemann-Pick disease, Lyme disease, Machado-Joseph disease, Sandhoff disease, Shy-Drager syndrome, wobbly hedgehog syndrome, proteopathy, cerebral 0-amyloid angiopathy, retinal ganglion cell degeneration in glaucoma, synucleinopathies, tauopathies, frontotemporal lobar degeneration (FTLD), dementia, cadasil syndrome, hereditary cerebral hemorrhage with amyloidosis, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, aortic medial amyloidosis, ApoAI amyloidosis, ApoAII amyloidosis, ApoAIV amyloidosis, familial amyloidosis of the Finnish type (FAF), lysozyme amyloidosis, fibrinogen amyloidosis, dialysis amyloidosis, inclusion body myositis/myopathy, cataracts, retinitis pigmentosa with rhodopsin mutations, medullary thyroid carcinoma, cardiac atrial amyloidosis, pituitary prolactinoma, hereditary lattice corneal dystrophy, cutaneous lichen amyloidosis, Mallory bodies, corneal lactoferrin amyloidosis, pulmonary alveolar proteinosis, odontogenic (Pindborg) tumor amyloid, cystic fibrosis, sickle cell disease or critical illness myopathy (CIM). Further medical uses include the treatment of bone-related disorders, such as osteoporosis or osteoarthritis, for which increased bone formation and decreased bone resorption may be beneficial.

Acronyms

Protective Groups:

Aloc or AOC, allyloxycarbonyl; Bom, benzyloxymethyl; 2-Br—Z, 2-bromobenzyloxycarbonyl; tBu, tert-butyl; Bz, benzoyl; Bzl, benzyl; Boc, tert-butoxycarbonyl; CHO, formyl; cHx, cyclohexyl; Cbz or Z, benzyloxycarbonyl; 2-Cl—Z, 2-chlorobenzyloxycarbonyl; Fm, 9-fluorenylmethyl; Fmoc, 9-fluorenylmethoxycarbonyl; Mtt, 4-methyltrityl; Pmc, (2,2,5,7,8-pentamethylchroman-6-sulphonyl; Tos, 4-toluenesulphonyl; Trt, triphenylmethyl; Xan, xanthyl.

Reagents and Solvents:

ACN: acetonitrile; BOP: benzotriazol-1-yloxytris (dimethylamino) phosphoronium hexafluorophosphate; DCC: N, N'-Dicyclohexylcarbodiimide; DCM: dichloromethane; DEPBT: 3-(Diethoxyphosphoryloxy)-1,2,3-benzotriazin-4 (3H)-one; DIC: N, N'-Diisopropylcarbodiimide; DIPEA (or DIEA): diisopropylethylamine; DMF: N,N-dimethylformamide; DMSO: dimethylsulfoxide; EDC or EDCI: 1-ethyl-3-(3-dimethylaminopropyl)carbodiimide; EtOAc: ethyl acetate; HATU: 1-[Bis(dimethylamino)methylene]-1H-1,2,3-triazolo[4,5-b]pyridinium 3-oxide hexafluorophosphate; HBTU: O-(1H-benzotriazole-1-yl)-N,N,N',N'-tetramethyluronium hexafluorophosphate; HOAT: 1-Hydroxy-γ-azabenzotriazole; HOBT: 1-hydroxybenzotriazole; Cl-HOBT: 6-chloro-1-hydroxybenzotriazole; NMM:

N-methylmorpholine; NMP: N-methylpyrrolidinone; Su: succinimide; TEA: triethylamine; TFA: trifluoroacetic acid; TIS: triisopropylsilane.

Peptide Chemical Synthesis Methods

Solid phase peptide synthesis is a well-developed methodology, which can be referenced in the literature such as R. C. Sheppard, Solid Phase Peptide Synthesis. A Practical Approach, Oxford-IRL Press, New York, 1989.

Linear peptides are made with Boc solid phase peptide synthesis or Fmoc solid phase peptide synthesis. If Fmoc chemistry is used to synthesize a peptide with a C-terminal carboxyl group, Wang resin is usually used; a peptide with a C-terminal amide is usually made with Rink amide resin (in this invention, Rink amide resin includes Rink amide-AM resin, Rink amide-MBHA resin, etc). If Boc chemistry is used to synthesize a peptide with a C-terminal carboxyl group, Pam resin is usually used; a peptide with a C-terminal amide is usually made with MBHA resin. Commonly used peptide coupling reagent and activator are DIC and HOBT, and other optional peptide bond coupling reagents include BOP, HBTU, DEPBT, etc. 5 equivalents of amino acids are usually used in the synthesis. Coupling reaction is usually 1 hour. Peptides can be synthesized manually, or they can be synthesized using a peptide solid phase synthesizer.

Fmoc protecting group is removed with 20% piperidine/DMF. Boc protecting group is removed with TFA. Peptide bond condensation reaction is monitored with Ninhydrin (2,2-Dihydroxyindane-1,3-dione) reagent.

For solid phase synthesis, either resins preloaded with the C-terminal amino acids or resins not loaded with amino acids can be used.

The method of loading the first amino acid on Rink amide resin can refer to the usual practice in the industry. A common method is briefly described as follows: weigh an appropriate amount of resin, remove the Fmoc protecting group with 20% piperidine/DMF in a solid-phase synthesis tube (15 mL/g resin, 30 minutes×2), and wash the resin with DMF. Weigh Fmoc amino acid, HATU, and HOAT equivalent to 5 times the moles of the amino group on the resin, and NMM equivalent to 10 times the moles of the amino group on the resin, add DMF to dissolve and mix the reagents, and transfer to solid phase synthesis tube. After overnight reaction, the resin is washed with DMF. Add 1:1 acetic anhydride/pyridine (v/v) to the solid phase synthesis tube, evacuate after 30 minutes, and wash the resin with DMF. The first amino acid is loaded.

When Fmoc solid phase peptide synthesis method is employed, the commonly used amino acids and protecting groups are as follows:

Fmoc-Cys(Trt)-OH, Fmoc-Asp(OtBu)-OH, Fmoc-Glu (OtBu)-OH, Fmoc-His(Trt)-OH, Fmoc-Lys(Boc)-OH, Fmoc-Asn(Trt)-OH, Fmoc-Gln(Trt)-OH, Fmoc-Arg (Pmc)-OH, Fmoc-Ser(tBu)-OH, Fmoc-Thr(tBu)-OH, Fmoc-Trp(Boc)-OH, Fmoc-Tyr(tBu)-OH Appropriately protected structural units are used in the synthesis process, such as the above-mentioned standard amino acids, Fmoc-8-amino-3,6-dioxaoctanoic acid (CAS No. 166108-71-0), and Fmoc-Glu-OtBu (CAS No. 84793-07-7). The introduction of fatty acid moieties can be achieved using structural units such as, but not limited to, eicosanedioic acid mono-t-butyl ester. After each coupling step, the unreacted peptide intermediate can be capped with acetic anhydride (10 equivalents) and excess collidine (20 equivalents).

After solid phase Fmoc chemical synthesis of peptides, the commonly used cleavage reagent is TFA. Place the dry resin in a flask, add an appropriate amount of cleavage solution (10-25 mL/g resin) containing 90:4:2:2:2 (v/v) trifluoroacetic acid:triisopropylsilane:1,2-ethanedithiol:water:thioanisole, cover with lid, and perform intermittent rotary shaking at room temperature. After 2 hours, the resin is filtered with suction, and washed with new TFA 2-3 times. The filtrate is combined, and ice-cooled ether is added dropwise. Finally, the precipitated crude peptide is collected by centrifugation.

When Boc solid-phase peptide synthesis method is employed, commonly used amino acids and protecting groups are as follows:

Boc-Cys(4-MeBzl)-OH, Boc-Asp(OcHx)-OH, Boc-Glu (OcHx)-OH, Boc-His(Bom)-OH, Boc-Lys(2-Cl—Z)—OH, Boc-Asn(Xan)-OH, Boc-Arg(Tos)-OH, Boc-Ser (Bzl)-OH, Boc-Thr(Bzl)-OH, Boc-Trp(CHO)—OH R Boc-Tyr(2-Br—Z)—OH

If the side chain amino group of lysine is used for lactam synthesis or acylation, the side chain amino group of lysine can be protected with allyloxycarbonyl (aloc) or Fmoc. If the side chain carboxyl group of aspartic acid or glutamic acid is used for lactam synthesis or acylation reaction, the carboxyl group should be converted to allyl ester or 9-fluorenylmethyl protection, such as Boc-Glu(OAll)-OH and Boc-Glu(Ofm)-OH.

After solid-phase Boc chemical synthesis of peptides, PAM and MBHA resins are usually cleaved with HF, 5 ml of HF per 0.1 mmol of resin, and the reagents such as p-cresol, p-mercaptophenol or anisole are added. The mixture is stirred for 1 hour under ice bath conditions. After HF is vacuum-dried, the peptide is precipitated with ether on ice, the precipitate is collected by centrifugation, separated and purified by HPLC, and then lyophilized to obtain the final product.

Purification

A crude peptide is dissolved in a suitable mixture of water and acetonitrile (e.g. water/acetonitrile 3:1) and purified by reversed-phase preparative HPLC (e.g. AKTA purifier, Shimadzu LC-20AR). Columns with different packings and sizes are selected according to the quantity and polarity of peptides, such as C8 or C18 semi-preparative or preparative columns. Buffer A is a 0.1% TFA aqueous solution, and buffer B is 0.1% TFA in acetonitrile. The gradient of buffer B is increased to elute peptides, and the relevant fractions are checked by analytical HPLC. A ZORBAX 300 SB-C18 (4.6×250 mm, 5 μM) column was used, buffer A was 0.1% TFA aqueous solution, and buffer B was 0.1% TFA in acetonitrile. The flow rate was 1 ml/min with UV detection at 210 nm. Fractions containing pure target peptides were combined and lyophilized to obtain the peptides as white solids. The products were stored separately in glass vials.

Preparation

The compounds of the present invention are linear peptides. Each amino acid can be coupled step by step from the C-terminus to the N-terminus of the peptide sequence to obtain the peptide backbone. The process is as follows: First, an amino acid whose amino group is protected by a blocking group is covalently attached to the solid phase carrier, and the amino protecting group of the first amino acid is removed, so far the first amino acid is connected to the solid phase carrier. Then the carboxyl group of the second amino acid whose amino group is protected is activated and reacts with the amino group of the first amino acid that has been attached to the solid phase carrier to form a peptide bond, in this way, a dipeptide with a protective group is generated on the solid phase carrier. Repeat the above peptide bond formation reaction to extend the peptide chain from the C-terminus to the N-terminus until the desired peptide chain is generated. Finally, the protective groups are removed, and the covalent bond between the peptide chain and the solid phase carrier is hydrolyzed to obtain a synthesized peptide.

Some compounds of the present invention are conjugated with long-acting groups or modifying groups through the side chain amino groups or thiol groups of amino acids whose side chains contain amino groups or thiol groups. Take compound 27 as an example to illustrate the synthetic route and method.

The synthesis of compound 27 includes the following steps:

Step A: Coupling Lys(PG) and resin to obtain Lys(PG)-resin. PG is a protecting group for the side chain amino group of lysine;

Step B: Lys(PG)-resin is coupled with amino acids or amino acid derivatives, through the first progressive coupling, to obtain the first peptide resin with the amino acid sequence shown in the main peptide chain of compound 27;

Step C: Remove the side chain protecting group PG of Lys in the first peptide resin whose amino acid sequence is shown in the main peptide chain of compound 27, and couple, through the second progressive coupling, 2-(2-(2-aminoethoxy) ethoxy) acetic acid, 2-(2-(2-amino-ethoxy) ethoxy) acetic acid, γ-Glu, and octadecanedioic acid to obtain the second peptide resin;

Step D: The second peptide resin is cleaved and the peptide is purified to obtain compound 27.

Preferably, the resin in step A is Rink Amide resin, or similar types of resins such as Rink Amide-AM resin, Rink Amide-MBHA resin, etc. Preferably, the coupling reagents used in in step A are selected from DIC and HOBt, or HATU and HOAT, or BOP, PyBOP, PyAOP, HBTU, TBTU, DEPBT, etc. Preferably, the side chain protecting group of Lys is aloc, Dde or ivDde.

In the first progressive coupling in Step B, according to the sequence of compound 27, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Ala-OH, Fmoc-Leu-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg(Pbf)-OH, Fmoc-Val-OH, Fmoc-Ala-OH, Fmoc-Glu(OtBu)-OH, Fmoc-Lys(Boc)-OH, Fmoc-Glu(OtBu)-OH, Fmoc-Leu-OH, Fmoc-Ala-OH, Fmoc-Ile-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Aib-OH and Boc-Tyr(tBu)-OH were coupled stepwise.

The coupling reagents used in the first progressive coupling in step B and in the second progressive coupling in step C include condensation reagents and reaction solvents. The reagents may be a mixed solution of DIC and HOBt, or a mixed solution of PyBOP, HOBt and DIEA, or a mixed solution of HATU, HOAt and DIEA, or a mixed solution of DEPBT and DIEA, or the mixed solution of HBTU and DIEA, and the reaction solvent is one or a mixture of two or more of DMF, DCM, NMP, or DMSO.

When PG is aloc, the deprotection reagents used in step C are 1-20 equivalents of morpholine (or 1-20 equivalents of phenylsilane instead of morphine) and 0.05-3 equivalents of $Pd(PPh_3)_4$. Preferably, aloc protective group is removed with 5-10 equivalents of morpholine (or 5-10 equivalents of phenylsilane instead of morphine) and 0.1-0.3 equivalents of $Pd(PPh_3)_4$. The protective group removal reaction can be performed twice, 10-30 minutes each time, and $CH_2C12$ is preferably used as the solvent.

Another method for removing Aloc protecting group is to use a catalytic amount of tetrakis(triphenylphosphine)palladium (0) and 37:2:1 ratio of DCM, glacial acetic acid and NMM (15 mL/g resin) in an argon atmosphere. The reaction is stirred at room temperature for 2 hours. After the reaction, each gram of resin is washed with 0.5% DIPEA/DMF (10 mL), 0.5% sodium diethyldithiocarbamate/DMF (3×10 mL), 1:1 DCM: DMF (5×10 mL).

When PG is Dde or ivDde, the reagent used to remove the protective group in step C is a hydrazine hydrate/DMF mixed solution. Prepare 2% (w/v) hydrazine hydrate in DMF solution (25 mL/g resin), add the resin, drain it after 5 minutes, and wash the resin with DMF. The process of deprotection with 2% hydrazine hydrate/DMF and DMF washing is repeated 3 times.

In the second progressive coupling in step C, according to the sequence of compound 27, Fmoc-8-amino-3,6-dioxaoctanoic acid (CAS No. 166108-71-0) and Fmoc-Glu-OtBu (CAS No. 84793-07-7) and octadecanedioic acid mono-tert-butyl ester HOOC—$(CH_2)_{16}$-COOtBu are coupled stepwise.

The reagents used for the cleavage in step D include TFA and one, two or more compounds of PhSMe, PhOMe, EDT, $H_2O$, TIS and PhOH. For example, the reagents used for cleavage are a mixture of TFA, thiolanisole, dimethyl sulfide and EDT, and the volume ratio of TFA, anisole, dimethyl sulfide, and EDT is 90:5:3:2. Preferably, the reagents used for cleavage are a mixture of TFA, $H_2O$ and TIS, and the volume ratio is 90:2.5:2.5.

The present invention also includes new intermediates and methods that can be used to synthesize the compounds of the present invention or pharmaceutically acceptable salts thereof. The intermediates and compounds of the present invention can be prepared by various methods known in the art. In particular, the chemical synthesis methods are exemplified in the following examples. The specific synthetic steps of each route described can be combined in different ways to prepare the compound of the invention or its salt thereof. Reagents and raw materials are readily available to those of ordinary skill in the art.

EXAMPLES

The invention is further explained with reference to the examples. These examples are by no means intended to limit the scope of the claims in this invention. Those skilled in the art can learn from the content of the present invention, appropriately improve the process parameters, make changes, or appropriately modify and combine the methods and applications of the present invention for implementation and application of the technology of the present invention. All similar substitutions and modifications are obvious to those skilled in the art, and they are all considered to be included in the present invention.

Amino acids and condensation reagents were purchased from GL Biochem (Shanghai) Co., Ltd. Rink Amide resin was purchased from Shangyu Puer Company and Tianjin Nankai Hecheng Science & Technology Co., Ltd.

Example 1 Synthesis of Compound 2

A pre-loaded low or medium loading Fmoc-Ser(tBu)-Rink Amide resin (e.g. 0.4 mmole/g) was used. The Fmoc protecting group was removed with 30% piperidine/DMF (2×10 minutes), and the resin was washed 3 times with DMF. Fmoc solid phase peptide synthesis method was used. The amino acid (10 times the molar amount of the preloaded amino acid on the resin) was dissolved in DMF to make a 0.3M solution. HOBT and DIC (10 times the molar amount of the amino acid on the resin respectively) were added to the solution. The mixed solution was shaken and mixed before added to the resin. The coupling was performed at room temperature for 60 minutes. The solution in the solid phase reaction tube was evacuated, and the resin was washed 3 times with DMF. The coupling of a synthetic unit was complete. The same coupling method was used for each synthetic unit from the C-terminus to the N-terminus of the peptide. Amino acid residues were protected by protective groups commonly used in Fmoc solid phase synthesis and listed in the "Peptide Chemical Synthesis Methods" section or other protective groups suitable for this sequence.

After synthesis of the peptide, the resin was washed with DCM and the cleavage solution containing trifluoroacetic acid:triisopropylsilane:1,2-ethanedithiol:water:anisole 90:4:2:2:2 (v/v) was added (10-25 mL/g resin). The reaction was agitated at room temperature for 2 hours and precipitated with ice-cooled ether. The crude peptide was dissolved in 0.1% TFA, 30% acetonitrile aqueous solution and purified with a preparative RP-HPLC, C8, 5 μM reverse phase column. Buffer A is a 0.1% TFA aqueous solution, and buffer B is 0.1% TFA in acetonitrile. The gradient of buffer B was gradually increased for elution of the peptide, and the correct fractions were combined and lyophilized at low temperature to obtain a white solid. The structure of the peptide was determined by mass spectrometry and amino acid sequencing. In the present invention, all compounds with a serine at the C-terminus can be synthesized according to the method of Example 1.

Example 2 Synthesis of Compound 7

A pre-loaded Fmoc-Gly-Rink Amide resin was used. The synthesis methods and steps were similar to those described in Example 1. In the present invention, all compounds with a C-terminal glycine can be synthesized according to the methods of Example 2.

Example 3 Synthesis of Compound 23

A preloaded low loading Fmoc-Lys(Aloc)-Rink Amide resin (e.g. 0.29 mmole/g) was selected. The coupling method described in Example 1 was used for each synthesis unit from the C-terminus to the N-terminus of the peptide. Amino acid residues other than C-terminal lysine were protected by protective groups commonly used in Fmoc solid phase synthesis and listed in the "Peptide Chemical Synthesis Methods" section. After the main peptide chain was synthesized the allyloxycarbonyl group of the C-terminal lysine side chain was removed by using tetrakis(triphenylphosphine)palladium(0) and 37:2:1 ratio of DCM, glacial acetic acid and NMM (15 mL/g resin). The reaction was stirred for 2 hours under argon atmosphere at room temperature. Tetrakis(triphenylphosphine)palladium(0) could be used in a catalytic amount to 1 equivalent. After the reaction, each gram of resin was washed with 0.5% DIPEA/DMF (10 mL), 0.5% sodium diethyldithiocarbamate/DMF (3×10 mL), 1:1 DCM:DMF (5×10 mL). The Aloc protecting group could also be removed with 5-10 equivalents of morpholine (or 5-10 equivalents of phenylsilane) and 0.1-0.3 equivalents of $Pd(PPh_3)_4$. The protective group removal reaction could be carried out twice, 30 minutes each time, using $CH_2Cl_2$ as the solvent. After removing the side chain Aloc protecting group, the structural units Fmoc-8-amino-3,6-dioxoctanoic acid (CAS No. 166108-71-0), Fmoc-Glu-OtBu (CAS No. 84793-07-7) and octadecanedioic acid mono-tert-butyl ester HOOC—$(CH_2)_{16}$-COOtBu were used for synthesis of this lysine side chain substituent. The amount of each structural unit of the side chain substituent used in the synthesis was equivalent to 10 times the molar amount of the amino group on the resin, and the coupling time was 4 hours for each step. The synthesis methods and steps were similar to those of Example 1.

Another method was to use a pre-loaded low loading Fmoc-Lys (ivDde)-Rink Amide resin. The method for synthesizing the main peptide chain was the same as the method using Fmoc-Lys(Aloc)-Rink Amide resin in the previous paragraph. After synthesis of the main peptide chain, the ivDde protecting group of the C-terminal lysine side chain was removed with 2% hydrazine hydrate/DMF. A 2% (w/v) hydrazine hydrate solution in DMF (25 mL/g resin) was prepared, added to the resin, and drained after 5 minutes. The resin was washed with DMF. The process of deprotection with 2% hydrazine hydrate/DMF and DMF washing was repeated 3 times. The synthesis method of this lysine side chain substituent was the same as the side chain coupling method of Fmoc-Lys(Aloc)-Rink Amide resin in the previous paragraph.

In the present invention, the compounds with a C-terminal lysine whose side chain amino group is connected to a long-acting group, such as compounds 4, 6, 11, 13, 14, 17, 21-23, 27-30, can also be synthesized according to the methods described in Example 3.

Example 4 Synthesis of Peptide 33

A pre-loaded Fmoc-Cys(Trt)-Rink Amide resin was used. The synthesis methods and steps were similar to those of Example 1. In the present invention, all compounds with a C-terminal cysteine can be synthesized according to the methods described in Example 4.

Example 5 Synthesis of Peptide 95

A pre-loaded Fmoc-Pro-Rink Amide resin was used. The synthesis methods and steps were similar to those of Example 1. In the present invention, all compounds with a proline at the C-terminus can be synthesized according to the methods described in Example 5.

Example 6 Synthesis of Peptide 110

A pre-loaded Fmoc-Ala-Rink Amide resin was used. The synthesis methods and steps were similar to those of Example 1. In the present invention, all compounds with an alanine at the C-terminus can be synthesized according to the methods described in Example 6.

TABLE 1

| Compound | Calculated molecular weight | Observed molecular weight |
|---|---|---|
| Compound 1 | 4191.6 | 4191.2 |
| Compound 2 | 4163.6 | 4163.1 |
| Compound 3 | 4177.6 | 4177.0 |
| Compound 4 | 5035.6 | 5035.4 |
| Compound 5 | 4294.7 | 4293.9 |
| Compound 6 | 4948.5 | 4947.6 |
| Compound 7 | 3328.7 | 3327.7 |
| Compound 8 | 4204.7 | 4203.1 |
| Compound 9 | 4176.6 | 4176.2 |
| Compound 10 | 4148.6 | 4148.0 |
| Compound 11 | 5048.7 | 5047.5 |

TABLE 1-continued

| Compound | Calculated molecular weight | Observed molecular weight |
|---|---|---|
| Compound 12 | 4217.7 | 4217.1 |
| Compound 13 | 4933.6 | 4933.5 |
| Compound 14 | 4961.6 | 4960.4 |
| Compound 15 | 3369.8 | 3368.7 |
| Compound 16 | 4233.7 | 4232.8 |
| Compound 17 | 5077.7 | 5076.3 |
| Compound 18 | 4120.6 | 4119.5 |
| Compound 19 | 4148.6 | 4147.1 |
| Compound 20 | 5010.7 | 5009.3 |
| Compound 21 | 4992.7 | 4992.5 |
| Compound 22 | 4905.6 | 4904.4 |
| Compound 23 | 4964.7 | 4963.9 |
| Compound 24 | 4120.6 | 4120.1 |
| Compound 25 | 3313.8 | 3312.6 |
| Compound 26 | 4923.6 | 4922.5 |
| Compound 27 | 4848.5 | 4847.8 |
| Compound 28 | 4935.6 | 4935.5 |
| Compound 29 | 4862.6 | 4862.4 |
| Compound 30 | 4949.6 | 4948.7 |
| Compound 31 | 4091.6 | 4090.3 |
| Compound 32 | 4194.7 | 4193.1 |
| Compound 33 | 4107.6 | 4107.2 |
| Compound 34 | 4219.8 | 4219.3 |
| Compound 35 | 4132.7 | 4131.9 |
| Compound 36 | 4105.6 | 4105.1 |
| Compound 37 | 4208.7 | 4208.3 |
| Compound 38 | 4121.7 | 4121.0 |
| Compound 39 | 4233.8 | 4232.6 |
| Compound 40 | 4146.7 | 4145.2 |
| Compound 41 | 3256.7 | 3256.1 |
| Compound 42 | 3270.7 | 3269.8 |
| Compound 43 | 4063.6 | 4063.1 |
| Compound 44 | 4104.7 | 4104.2 |
| Compound 45 | 4191.7 | 4190.4 |
| Compound 46 | 4166.7 | 4166.2 |
| Compound 47 | 4079.6 | 4078.0 |
| Compound 48 | 4077.6 | 4076.8 |
| Compound 49 | 4118.7 | 4118.1 |
| Compound 50 | 4205.8 | 4205.2 |
| Compound 51 | 4093.7 | 4093.0 |
| Compound 52 | 4180.7 | 4179.3 |
| Compound 53 | 4119.6 | 4119.7 |
| Compound 54 | 4103.6 | 4103.1 |
| Compound 55 | 4092.6 | 4092.0 |
| Compound 115 | 3727.3 | 3726.8 |
| Compound 178 | 3512.0 | 3511.6 |

The molecular weights from mass spectrometry and amino acid sequencing results prove that the peptide structures are correct.

A peptide was dissolved in PBS (pH7.4) to make a stock solution. The peptide concentration in the stock solution was quantified by conventional methods such as Bradford method and ultraviolet spectrophotometry. Before the drug efficacy experiments in animals, the required doses were taken from the peptide stock solution, diluted with PBS (pH7.4) to prepare an injection solution. An appropriate injection volume for each animal was 5 ml/kg body weight, which was used to calculate the injection volume that need to be configured.

All data of animal experiments was entered into Excel spreadsheets, and all values were expressed as mean±SEM. The significances of the differences among multiple groups were evaluated by one-way analysis of variance (ANOVA) followed by Dunnett's test using graphpad Prism 6 software. The means of two groups was compared by the unpaired T-Test, and a P value of less than 0.05 was considered as statistically significant.

Example 7

In vivo efficacy of the peptides of the present invention can be determined in any suitable animal models known in the art and in clinical trials. For example, db/db mouse is a suitable animal model of diabetes.

db/db mice were housed in animal feeding rooms with strictly controlled environmental conditions. The temperature in the feeding room was maintained at 20-24° C. and the humidity was maintained at 40-70%. The temperature and humidity of the feeding room were monitored in real time by a temperature and humidity meter, and the temperature and humidity were recorded twice a day (once in the morning and once in the afternoon). The lighting in the animal feeding room was controlled by an electronic timing light-on system. The lights were turned on for 12 hours and turned off for 12 hours every day (on at 7:00 in the morning and off at 19:00 in the afternoon). During the experiment, the mice were individually housed in each cage, and toys were provided to the mice in each cage. During the experiment mice had free access to water. The db/db male mice (6 weeks old) were given one week to acclimate to the environmental conditions of the test facility. Baseline blood glucose and body weight were recorded for three days before the test (−3 day to −1 day). The mice were randomly grouped based on three-day blood glucose and body weight, with 6 mice in each group. The mice were injected subcutaneously with PBS (5 ml/kg, control group) or the peptide compounds 1, 2, 8, 16, 18, 19, 24, and 36 (30 nmol/kg) respectively at 10:00 am. Blood was collected at 0 hour before drug administration, and 1, 2, 4, 6, 8 and 10 hours after administration, and blood glucose was measured using a OneTouch glucose meter (Johnson & Johnson) and test strips. Blood glucose curves were plotted with time as the abscissa and the blood glucose value at different time point as the ordinate, the areas under the curve (AUC) were calculated, and the hypoglycemic effects and duration of time of the peptide compounds were compared.

The results in FIG. 1 indicate that compounds 1, 2, 8, 16, 18, 19, 24, and 36 could significantly reduce blood glucose of type 2 diabetic mice, and the differences between the control group and the treatment groups were statistically significant. These compounds have potential as medicaments for diabetes.

Example 8

The feeding conditions of db/db mice were the same as described in Example 7. The db/db male mice (8 weeks old) were given one week to acclimate to the environmental conditions of the test facility. Baseline blood glucose and body weight were recorded for three days before the experiment (−3 day to −1 day). The mice were randomly grouped based on their three-day blood glucose and body weight, with 6 mice in each group. Mice were injected subcutaneously with PBS (5 ml/kg, control group) or the peptide compounds 31, 35, 38, 44 and 49 (30 nmol/kg) respectively at 10:00 in the morning. Blood was collected at 0 hour before drug administration, and 1, 2, 4, 6, 8, and 10 hours after administration, and blood glucose was measured using a OneTouch glucose meter (Johnson & Johnson) and test strips. Blood glucose curves were plotted with time as the abscissa and the blood glucose value at different time point as the ordinate, and the areas under the curve (AUC) were calculated.

Figure 2:
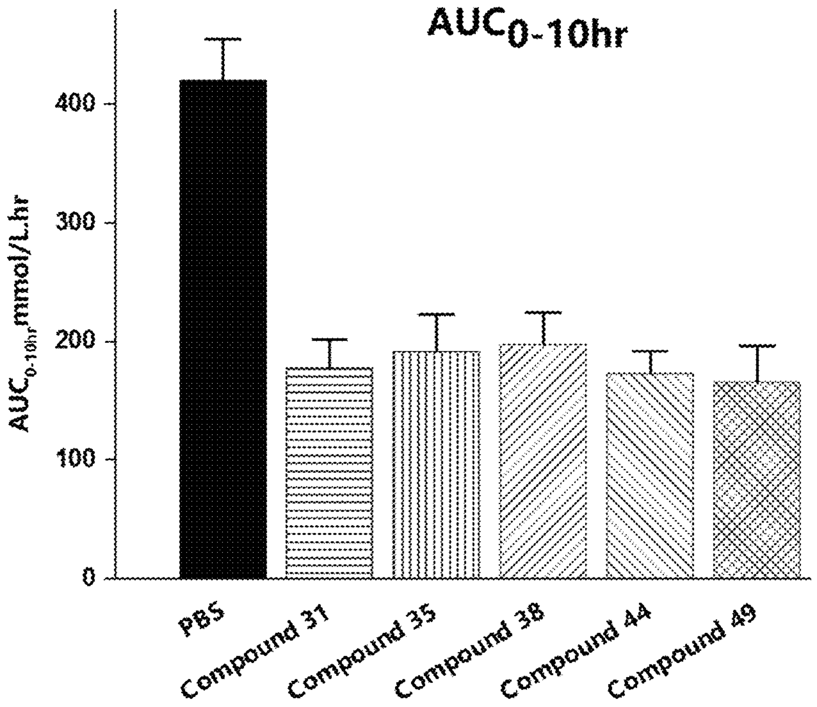
FIG. 2: Testing of compounds 31, 35, 38, 44 and 49 of the present invention to lower blood glucose in db/db mice.

The results in FIG. 2 show that compounds 31, 35, 38, 44 and 49 significantly reduced the blood glucose of type 2 diabetic mice, and the differences between the control group and the treatment groups were statistically significant. These compounds have potential as medicaments for diabetes.

Example 9

The feeding conditions of db/db mice were the same as described in Example 7. Baseline blood glucose and body weight of db/db male mice (6 weeks old) were recorded for three days before the experiment (−3 day to −1 day). The mice were randomly grouped based on their three-day blood glucose and body weight, with 6 mice in each group. The animals were injected subcutaneously with PBS (5 ml/kg, control group) or compounds 6, 13, 14 and 26 (3 nmol/kg) respectively at 18:00 the day before the experiment (−1 day). On the day of the experiment, the animals were fasted for 6 hours (8:00-14:00) and subjected to intraperitoneal glucose tolerance test (IPGTT). The animals were given a single intraperitoneal injection of glucose (1.5 g/kg) aqueous solution at 14:00, and the time for giving glucose was recorded as time 0. The blood glucose of the animals at 0 minute before glucose administration and 15, 30, 60, 120 and 180 minutes after glucose administration were measured. Blood glucose curves were plotted with time as the abscissa and the blood glucose value at different time point as the ordinate.

Figure 3:
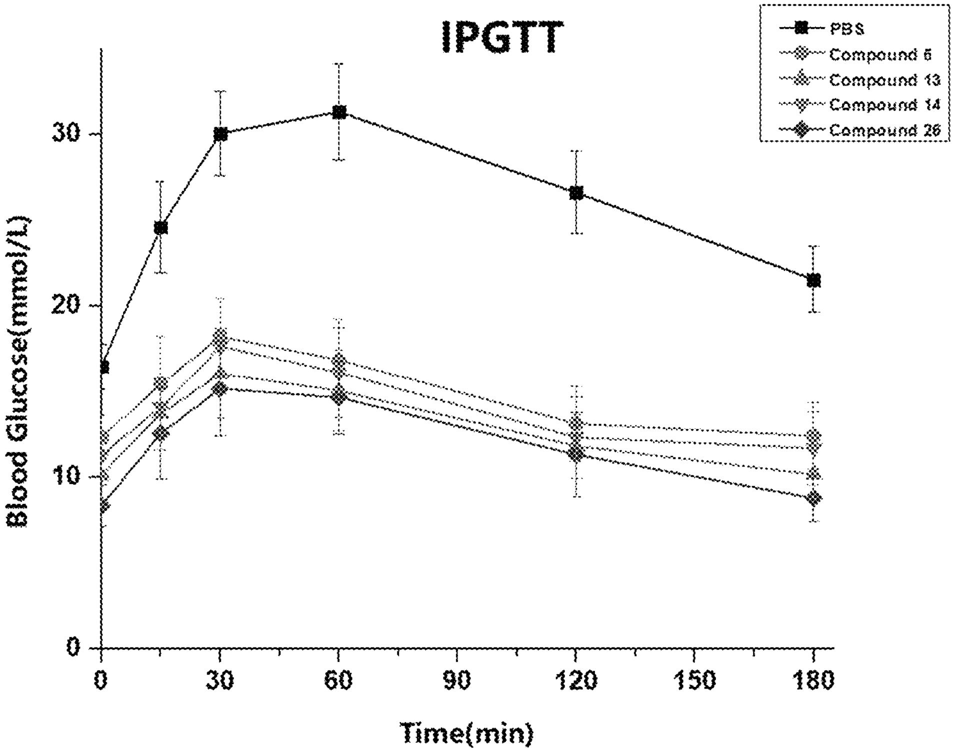
FIG. 3: Intraperitoneal glucose tolerance test (IPGTT) of compounds 6, 13, 14 and 26 of the present invention.

The results in FIG. 3 indicate that compounds 6, 13, 14 and 26 significantly reduced the blood glucose of type 2 diabetic mice, and displayed extended duration of in vivo activity. These compounds have the potential as long-acting diabetes treatment drugs.

Example 10

The in vivo efficacy of the peptides of the present invention can be determined in any suitable animal models known in the art and in clinical trials. Diet-induced obesity (DIO) mouse is an animal model of obesity, insulin resistance and hyperlipidemia.

Five-week-old male C57BL/6 mice were housed in the animal feeding room with strictly controlled environmental conditions. The temperature in the feeding room was maintained at 20-24° C., and the humidity was maintained at 30-70%. The temperature and humidity of the feeding room were monitored in real time by a temperature and humidity meter, and the temperature and humidity were recorded twice a day (once in the morning and once in the afternoon). The lighting in the animal feeding room was controlled by an electronic timing light-on system. The lights were turned on for 12 hours and turned off for 12 hours every day (on at 6:00 in the morning and off at 18:00 in the afternoon). During the experiment, the mice were individually housed in each cage, and toys were provided to the mice in each cage. Animals were fed on high-fat feed (the weight ratio of each nutrient was 26.2% protein, 26.3% carbohydrate, 36.9% fat, and the percentage of calories provided was 20%, 20%, and 60%, respectively) starting at 6 weeks of age. During the feeding process, the animals drank freely. 25-week-old male DIO mice with an average body weight of about 49 grams were selected for the experiment. The animals were adapted to grasping and subcutaneous injection for 1 week. The body weight and food intake were measured for 3 consecutive days before the experiment. The blood glucose of the animals was measured 1 day before the experiment, and the animals were grouped based on their blood glucose and body weight, 6 animals in each group.

During the experiment, animals in the control group and liraglutide group were injected subcutaneously with PBS or liraglutide (100 nmol/kg) once a day. The other 5 groups of animals were injected subcutaneously with peptides 4, 11, 17, 20 and 23 (25 nmol/kg) once on days 1, 3, 5, 7, 9, 11, and 13. During the 14-day experiment, the animal's body weight and food intake were measured every day. The percentage change in body weight is [(final body weight-starting body weight)/starting body weight]*100.

The animals' fasting blood glucose was measured with a blood glucose meter one day before the experiment and on the 15th day. When fasting blood glucose was measured the animals' fasting time was from 9:00 am to 15:00 pm, and the blood glucose was measured at 15:00 pm.

On the 16th day, the animals were fasted for 6 hours (8:00-14:00). Euthanasia was performed, and animals were dissected. Blood was collected from the heart and centrifuged into plasma for biochemistry tests. The main metabolic panel included triglycerides (TG) and cholesterol (TC). Hitachi series automatic biochemical analyzer (HITACHI 7180) was used for the analysis of biochemical substances. In addition, animal livers were collected to measure liver triglycerides and cholesterol.

Figure 4:
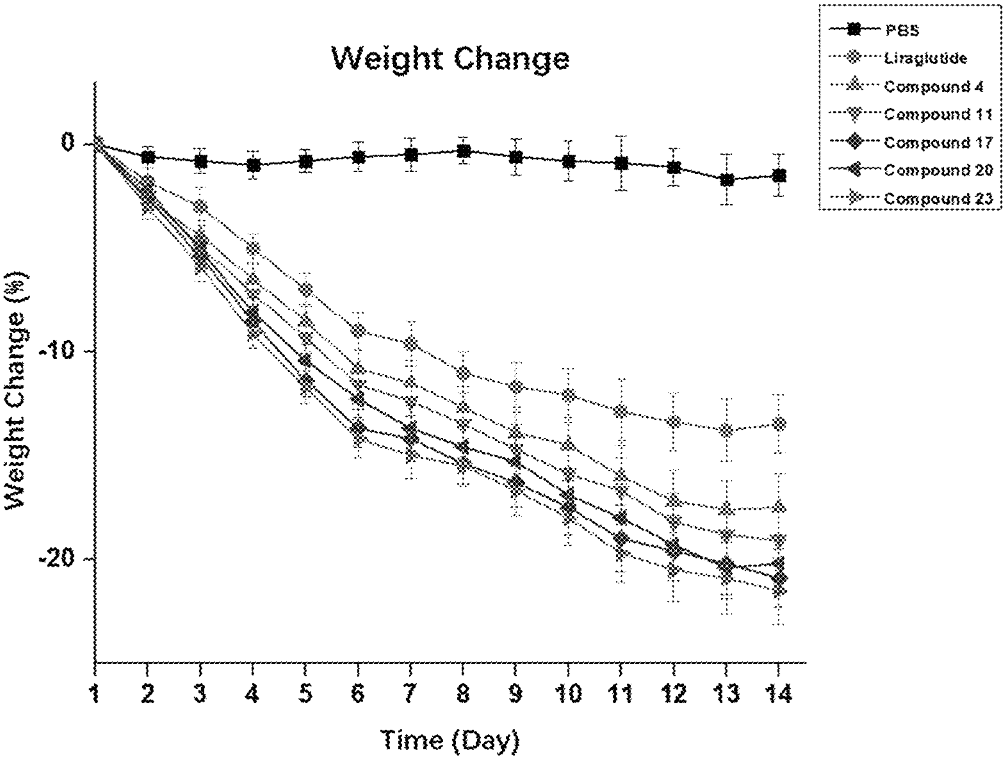
FIG. 4: Tests of compounds 4, 11, 17, 20 and 23 of the present invention to reduce body weight.

The results of the animals' body weight change in 14 days are shown in FIG. 4. Compared with the control group, the body weights of the treatment groups decreased significantly, and the body weight of the treatment groups on the 14th day were statistically significantly different from that of the control group, and the ability of peptides 4, 11, 17, 20, and 23 to reduce body weight was significantly better than the weight loss drug Liraglutide.

Figure 5:
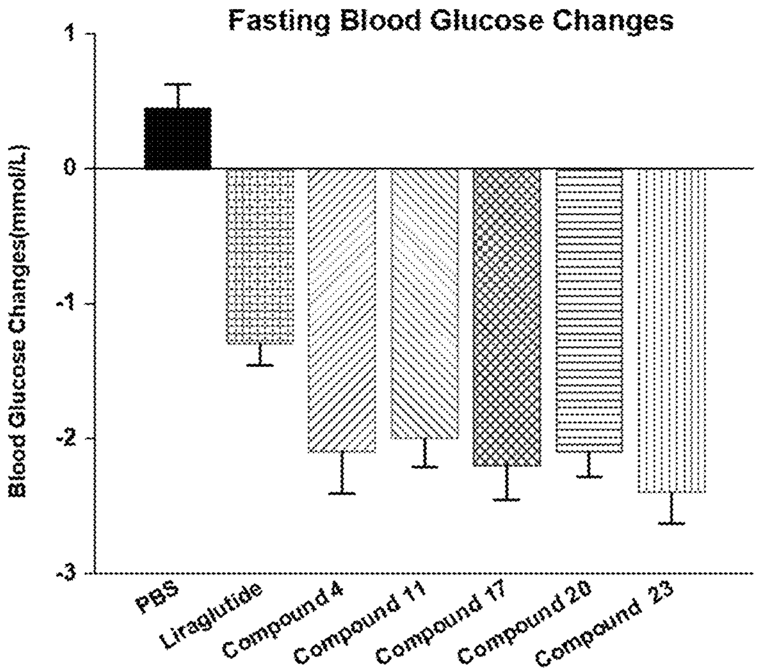
FIG. 5: Change of fasting blood glucose for compounds 4, 11, 17, 20 and 23 of the present invention.

The changes in fasting blood glucose (comparison of fasting blood glucose before the start of the experiment and after the completion of the experiment) are shown in FIG. 5, indicating that the fasting blood glucose of the treatment groups decreased substantially compared with that of the control group, and the peptide 4, 11, 17, 20 and 23 groups were better than Liraglutide group. The decrease in fasting blood glucose showed that the animals in the treatment groups had improved their ability to regulate blood glucose.

Figure 6:
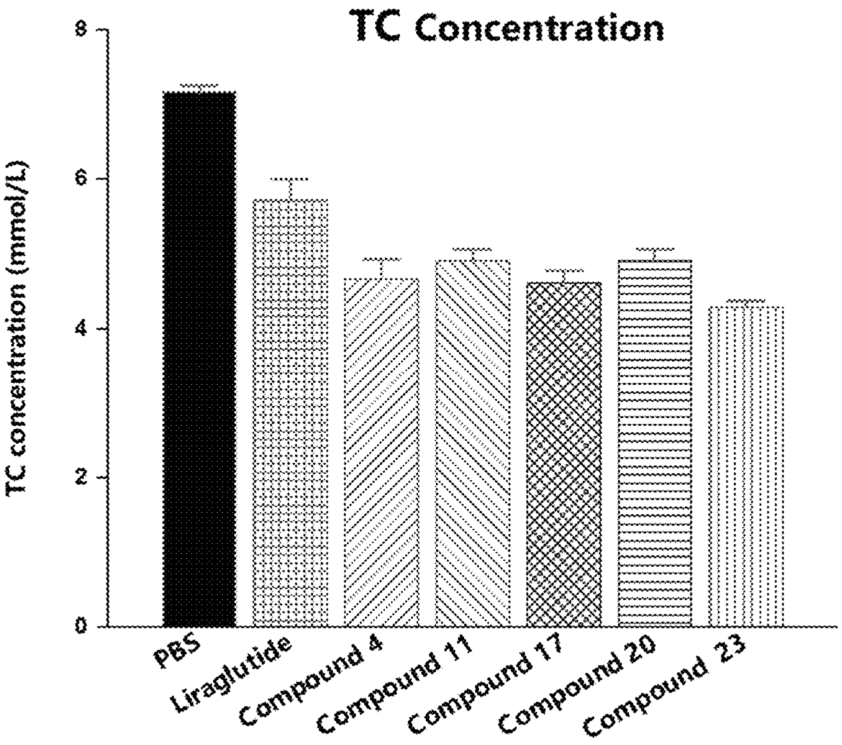
FIG. 6: Compounds 4, 11, 17, 20 and 23 of the present invention effectively reduced TC concentration.
Figure 7:
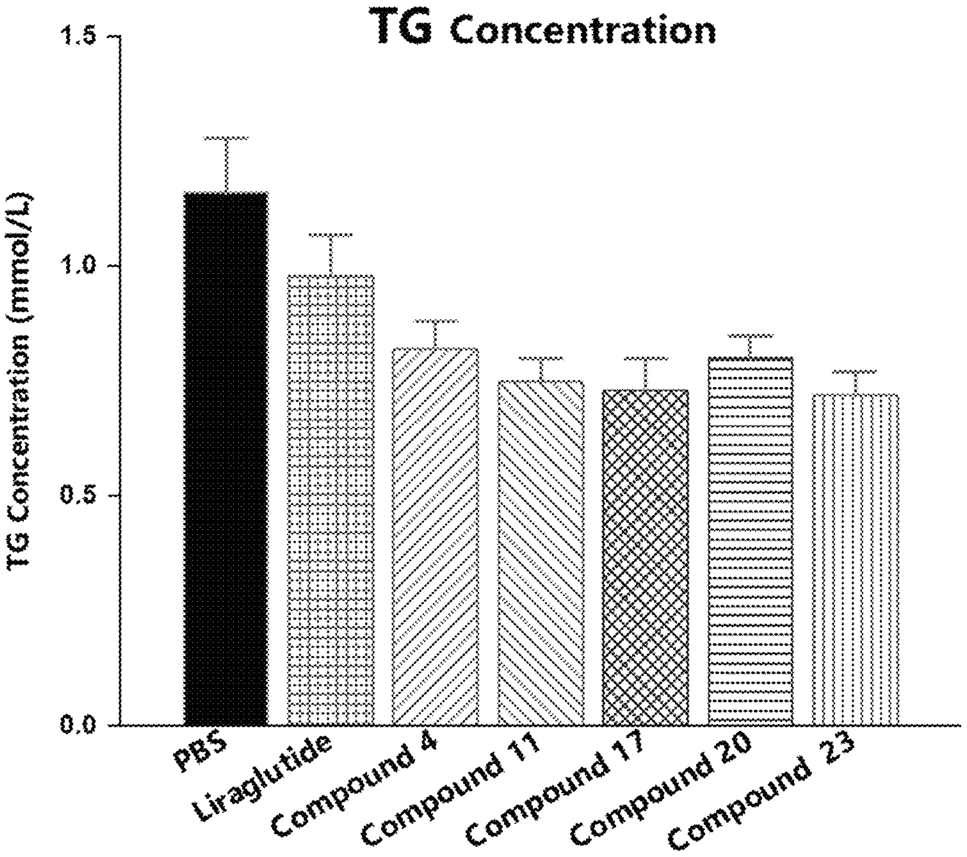
FIG. 7: Compounds 4, 11, 17, 20 and 23 of the present invention effectively reduced TG concentration.

As shown in FIGS. 6 and 7, in comparison to the control group, cholesterol and triglycerides of the animals in the treatment groups were significantly reduced, and the decline in the peptide 4, 11, 17, 20, and 23 groups was significantly greater than that in liraglutide group.

Example 11

After arriving at the facility db/db male mice (GemPharmatech, 6 weeks old) were kept in the animal feeding room with strictly controlled environmental conditions. The temperature of the feeding room was maintained at 20-24° C. and the humidity was maintained at 40-70%. The temperature and humidity of the feeding room were monitored in real time by a temperature and humidity meter, and the temperature and humidity were recorded twice a day (once in the morning and once in the afternoon). The lighting in the animal feeding room was controlled by an electronic timing light-on system. The lights were turned on for 12 hours and turned off for 12 hours every day (on at 7:00 in the morning and off at 19:00 in the afternoon). During the experiment, animals were individually housed in each cage, and toys were provided to the mice in each cage. During the experiment animals had free access to water. The animals were given two weeks to acclimate to the environmental conditions of the test facility. Three days before the experiment (−3 day to −1 day), the animals were fasted for 6 hours at 9:00 AM, and fasting blood glucose was measured at 15:00. The mice were randomly grouped based on three-day fasting blood glucose and body weight, with 6 mice in each group. The objective of the experiment was to measure the ability of the compounds to reduce fasting blood glucose in mice. The fasting time for animals during the experiment was from 9:00 am to 21:00 pm. On the first day of the experiment the mice were fasted for 6 hours in advance (9:00-15:00), and then subcutaneously injected with PBS (5 ml/kg) or compounds 21, 22, 27, 28, 29, and 30 (5 nmol/kg) respectively. Blood was collected at 0 hours before drug administration and 1, 3, 6, 24, 30 and 48 hours after administration, and the blood glucose was measured using a OneTouch glucose meter (Johnson & Johnson) and test strips. Blood glucose curves were plotted with time as the abscissa and the blood glucose value at different time point as the ordinate.

Figure 8:
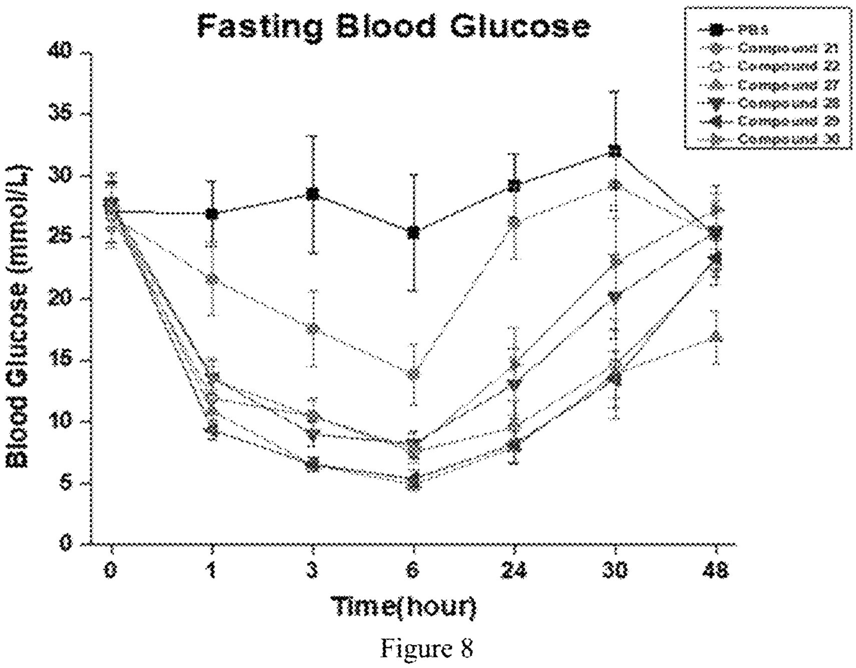
FIG. 8: Fasting blood glucose tests for compounds 21, 22, 27, 28, 29 and 30 of the present invention.

The results are shown in FIG. 8. Compounds 21, 22, 27, 28, 29, and 30 drastically reduced fasting blood glucose of db/db mice, and the difference between the control group and the treatment groups were statistically significant. These compounds have potential as long-acting diabetes treatment drugs. In addition, three pairs of compounds 21 and 22, 27 and 28, 29 and 30 show that, when the side chain of the compounds' C-terminal lysine is conjugated to the long-acting group, deletion of the adjacent serine residue significantly improves the efficacy of the resulting compounds and renders unexpected effect.

Example 12

The feeding conditions of db/db mice were the same as described in Example 7. The db/db male mice (GemPharmatech, 7 weeks old) had one-week to acclimate to the environmental conditions of the test facility. Three days before the test (−3 day~−1 day) baseline blood glucose and body weight were recorded. The mice were randomly grouped based on three-day blood glucose and body weight, with 6 mice in each group. Mice were injected subcutaneously with PBS (5 ml/kg, control group) or peptide compounds 42, 115, 178 (35 nmol/kg) at 10:00 in the morning. Blood was collected at 0 hour before drug administration, and 1.5, 4, 7, and 10 hours after administration, and blood glucose was measured using a OneTouch glucose meter (Johnson & Johnson) and test strips. By using time as the abscissa and the blood glucose value at different time points as the ordinate blood glucose curves were drawn, and the areas under the curve (AUC) were calculated to compare the hypoglycemic effects and duration of action of the peptide compounds.

Figure 9:
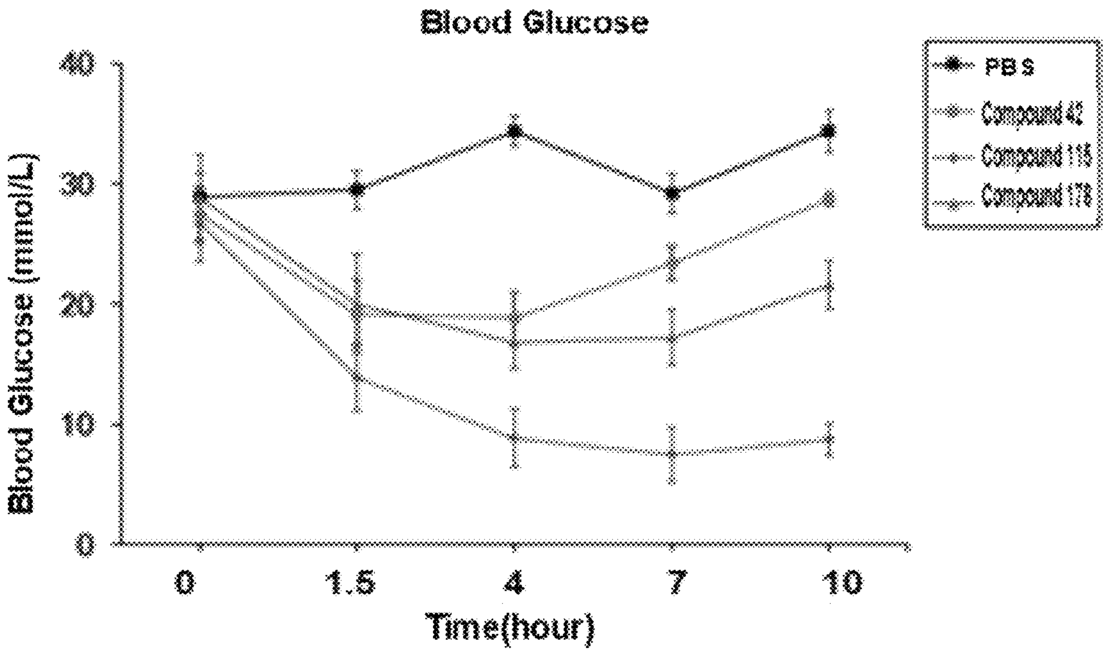
FIG. 9: Tests of compounds 42, 115 and 178 of the present invention to lower blood glucose in db/db mice.

The results are shown in FIG. 9. Compounds 42, 115, and 178 significantly reduced blood glucose in type 2 diabetic mice. These compounds have potential as medicaments for diabetes.

Example 13

The DIO obese mice experiment was conducted by Shanghai WuXi AppTec New Drug Development Co., Ltd. Male C57BL/6 mice were fed with high-fat feed (Catalog Number: D12492i, Research Diets, Inc) for 25 weeks from 5 weeks of age. The animals were adapted to grasping and subcutaneous injection for 1 week at 30 weeks of age. The body weight and food intake were measured for 3 consecutive days before the experiment, and the fasting blood glucose of the animals was measured 1 day before the experiment. The animals with abnormal blood glucose were removed, and the remaining animals were grouped based on their random blood glucose and body weight (using body weight as the main reference indicator), with 5 animals per group. During the experiment animals were injected subcutaneously with PBS, compound 27 and compound 29 (3 nmol/kg) once a day according to the group, and the dosing period was 10 days. During the experiment, the body weight and food intake of the animals were measured every day. After the experiment, the animals were fasted for 6 hours, euthanasia was performed, and the animals were dissected. Blood was collected from the heart and centrifuged into plasma and packed for biochemical analysis.

Figure 10:
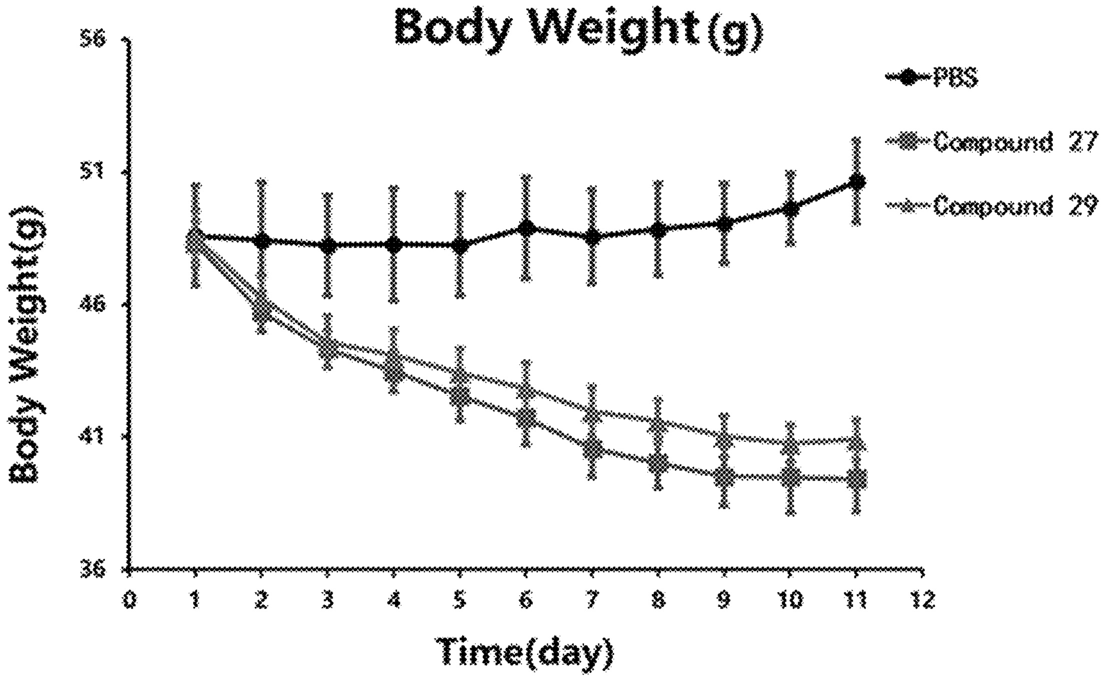
FIG. 10: Compound 27 and compound 29 of the present invention were effective in reducing body weight.

As shown in FIG. 10, the body weight of the animals in the treatment groups decreased significantly compared with that in the control group. On the 11th day, the body weight of the animals in each treatment group was statistically significantly different from the starting body weight of the animals in the same group and was also statistically significantly different from that in the control group ($P<0.0001$).

Figure 11:
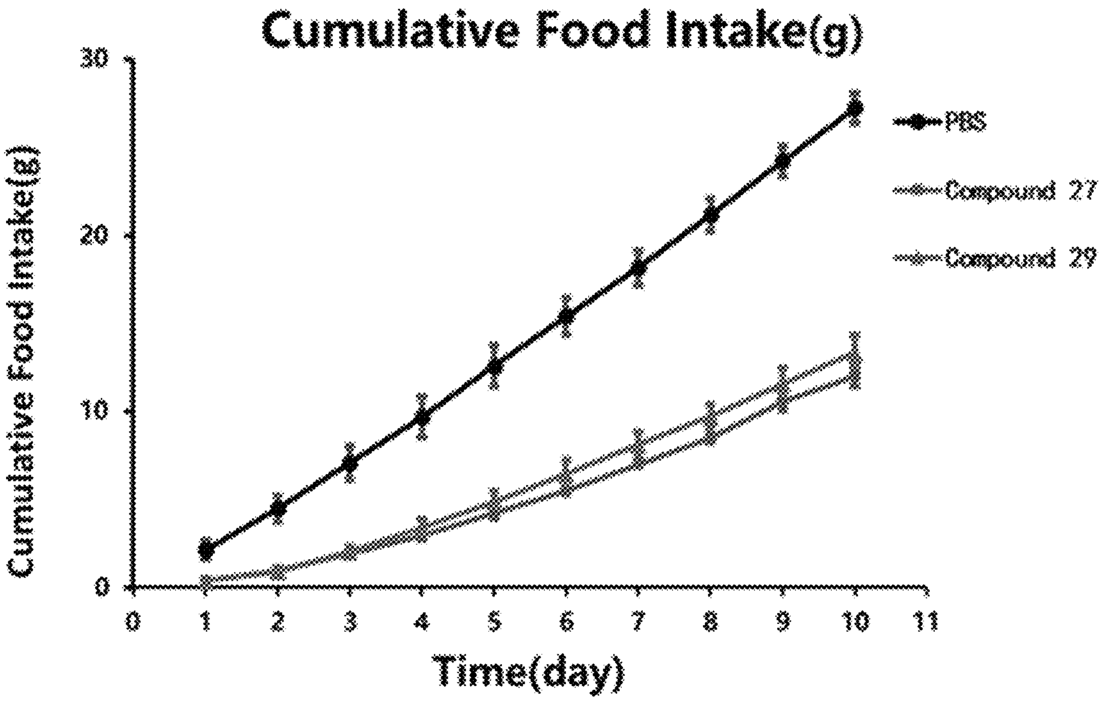
FIG. 11: Compound 27 and compound 29 of the present invention were effective in reducing food intake.

As shown in FIG. 11, the food intake of the animals in the treatment groups decreased significantly compared with that in the control group. The 10-day cumulative food intake of the animals in each treatment group was statistically significantly different from that in the control group ($P<0.0001$), indicating that compound 27 and compound 29 had an appetite suppressing effect.

Figure 12:
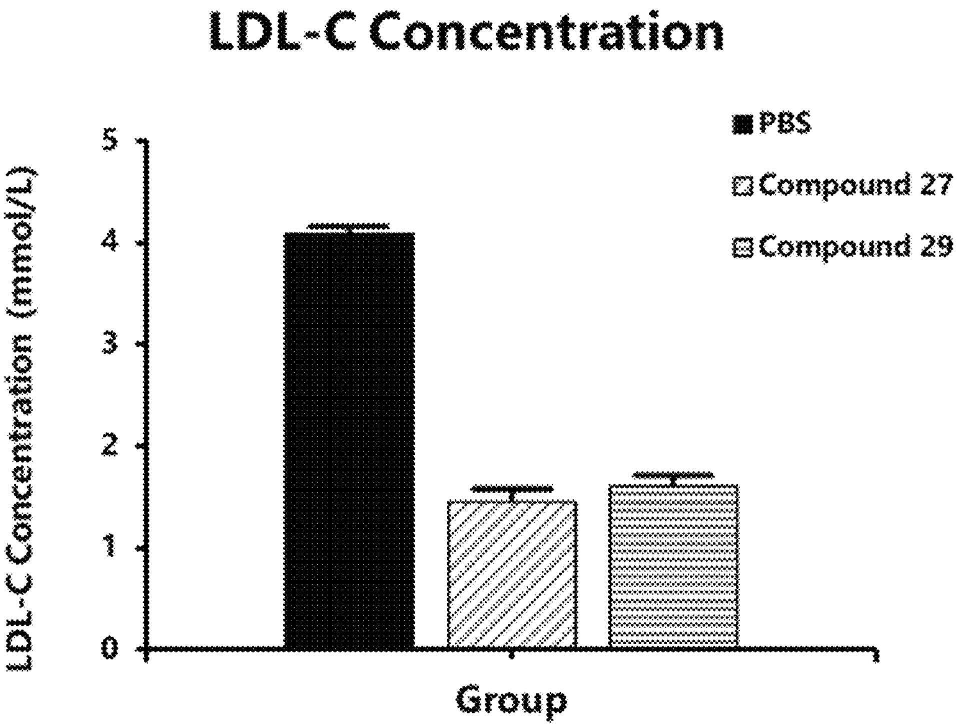
FIG. 12: Compound 27 and compound 29 of the present invention were effective in reducing low density lipoprotein cholesterol (LDL-C).

As shown in FIG. 12, compound 27 and compound 29 greatly reduced the low-density lipoprotein cholesterol (LDL-C) of experimental animals. LDL-C of each treatment group was statistically significantly different from that of the control group ($P<0.0001$). As LDL-C is closely related to cardiovascular disease, compound 27 and compound 29 have the potential to be used in the treatment of hyperlipidemia and reduce the risk of cardiovascular disease.

Example 14

The DIO obese mice experiment was conducted by Shanghai WuXi AppTec New Drug Development Co., Ltd. The animal feeding was the same as described in Example 13. The animals were adapted to grasping and subcutaneous injection for 1 week at 40 weeks of age. The body weight and food intake were measured for 3 consecutive days before the experiment, and the fasting blood glucose of the animals was measured 1 day before the experiment. The animals with abnormal blood glucose were removed, and the remaining animals were grouped according to the random blood glucose and body weight of the animals (using body weight as the main reference indicator), with 6 animals per group and an average weight of 47 grams. During the experiment, each group of the animals was injected subcutaneously with PBS, or 1.5 nmole of compound 35 or compound 40 per animal once a day, and the dosing period was 14 days. An EchoMRI body composition analyzer was used to measure the body fat content of the animals before and after the experiment.

Figure 13:
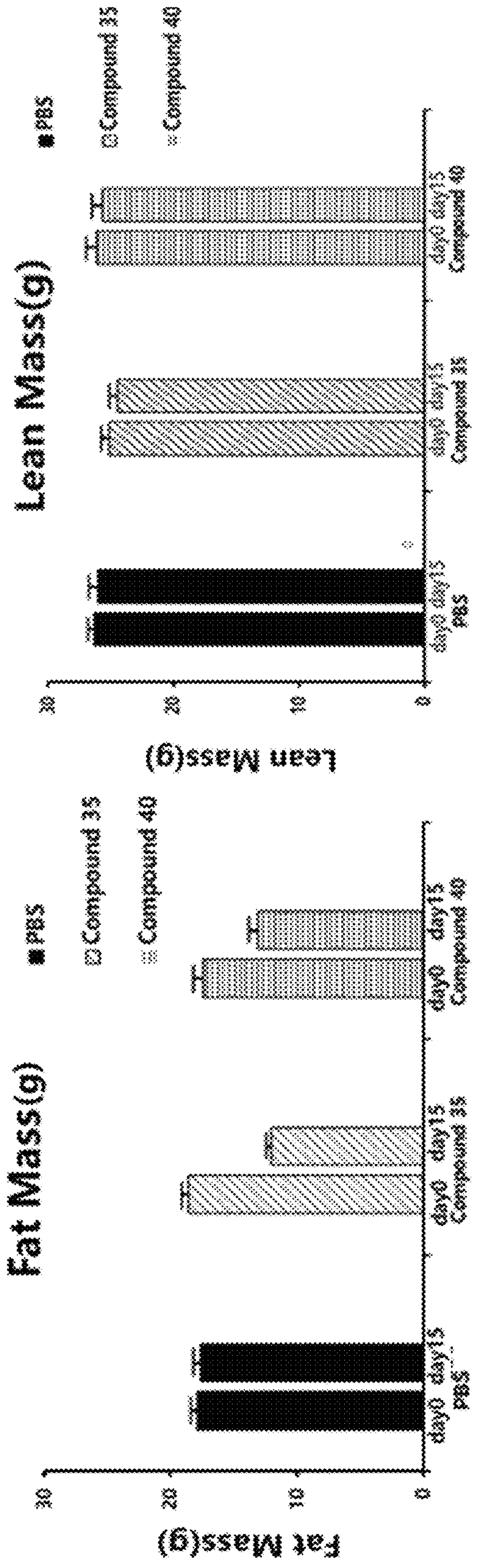
FIG. 13: Compound 35 and compound 40 of the present invention effectively reduced fat mass.

FIG. 13 showed the changes of fat mass and lean mass in DIO obese mice before the start of the experiment (day 0) and after the end of the experiment (day 15). Compared with the control group, the fat mass of the animals in the treatment groups decreased markedly and was statistically significant different from that in the control group, but the lean mass was basically unchanged, indicating that compound 35 and compound 40 could reduce body weight in an ideal way.

What is claimed is:

1. A peptide compound of formula (VII) or a pharmaceutically acceptable salt or solvate thereof, Y-aib-E-G-T-F-X11-S-D-X1-S-X12-X2-L-X3-X4-E-A-X5-X6-X13-F-X7-X8-W-L-X9-A-G-X10 (VII) (SEQ ID NO: 220), wherein X1 is an amino acid selected from L or Y;

X2 is an amino acid selected from Q, A, aib or Y;

X3 is an amino acid selected from D or E;

X4 is an amino acid selected from E or K;

X5 is an amino acid selected from V or A;

X6 is an amino acid selected from K or R;

X7 is an amino acid selected from I or V;

X8 is an amino acid selected from E or N;

X9 is an amino acid selected from I or L;

X10 is GPSSGAPPP (SEQ ID NO: 227), GPSSGA (SEQ ID NO: 232), or GPS (SEQ ID NO: 236); wherein one or two amino acids selected from serine, lysine or cysteine are added to the C-terminus of X10, and the carboxyl group of the C-terminal amino acid is optionally amidated to a C-terminal amide, optionally, the lysine or cysteine at the C-terminus of X10 contains a side chain which is modified with a long-acting group, wherein the long-acting group has the structure of formula (IV):

O1-O2-O3-O4-O5-O6-O7-O8- (IV), wherein O1 has the structure of formula (V) or (VI):

(II)

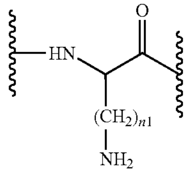

or

-continued (III)

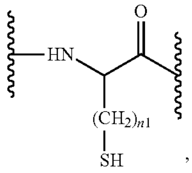

, wherein n2 is an integer of 10-24;

wherein the wavy line indicates the attachment point to the adjacent group, and O2-O3-O4-O5-O6-O7-O8- represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, and O2 to O8 contain at least one negatively charged moiety;

or X10 is absent;

X11 is T;

X12 is I;

X13 is L.

2. The peptide compound or the pharmaceutically acceptable salt or solvate of claim 1, wherein the peptide compound has the structure of formula (I), Y-aib-E-G-T-F-T-S-D-X1-S-I-X2-L-X3-X4-E-A-X5-X6-L-F-X7-X8-W-L-X9-A-G-X10 (I) (SEQ ID NO: 221), wherein X1 is an amino acid selected from L or Y, X2 is an amino acid selected from Q or Y, X3 is an amino acid selected from D or E, X4 is an amino acid selected from E or K, X5 is V, X6 is an amino acid selected from K or R, X7 is an amino acid selected from I or V, X8 is an amino acid selected from E or N, X9 is an amino acid selected from I or L, X10 is GPSSGAPPP (SEQ ID NO: 227), wherein the serine and lysine are sequentially added to the C-terminus of X10, wherein the lysine is added to the C-terminus of X10;

wherein the lysine contains a side chain amino group which is modified with a long-acting group; the long-acting group has the structure of formula (IV):

O1-O2-O3-O4-O5-O6-O7-O8- (IV), wherein O1 has the structure of formula (V) or (VI):

(V)

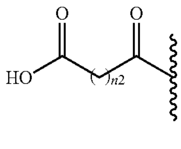

or

-continued (VI)

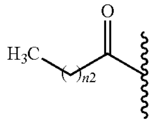

wherein n2 is an integer of 6-24;

wherein the wavy line indicates the attachment point to the amino group of the adjacent group, and O2-O3-O4-O5-O6-O7-O8- represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, and O2 to O8 contain at least one negatively charged moiety.

3. The peptide compound or the pharmaceutically acceptable salt or solvate of claim 1, wherein O2-O3-O4-O5-O6-O7-O8- represents a linker selected from the group consisting of γGlu-PEG2-γGlu-, γGlu-PEG2-γGlu-γGlu-, γGlu-PEG2-, γGlu-PEG2-PEG2-, γGlu-PEG2-PEG2-PEG2-, γGlu-PEG2-γGlu-PEG2, γGlu-PEG2-PEG2-γGlu-, γGlu-PEG2-PEG2-γGlu-γGlu-, γGlu-γGlu-, γGlu-γGlu-PEG2-, γGlu-γGlu-PEG2-γGlu-, γGlu-γGlu-PEG2-γGlu-PEG2-, γGlu-γGlu-PEG2-PEG2-, γGlu-γGlu-PEG2-PEG2-γGlu, γGlu-γGlu-PEG2-PEG2-γGlu-γGlu-.

4. The peptide compound or the pharmaceutically acceptable salt or solvate of claim 1, wherein the cysteine at the C-terminus of X10 contains a side chain thiol group which is modified with a long-acting group of formula (IV), the side chain thiol of said amino acid is connected to one end of the linking group L through a Michael reaction acceptor or a thiol reactive group, optionally, the other end of said linking group L forms a covalent bond with the long-acting group of formula (IV) through an amino group or a carboxyl group; optionally, the linking group L is selected from: $-NH-(CH_2)_{n5}-(CH_2CH_2O)_{n6}-(CH_2)_{n7}-$, $-NH-(CH_2)_{n5}-(CH_2CH_2O)_{n6}-(CH_2)_{n7}-NH-$, $-NH-(CH_2)_{n5}-(CH_2CH_2O)_{n6}-(CH_2)_{n7}-CO-$, $-NH-(CH_2)_{n5}-(CH_2CH_2O)_{n6}-(CH_2)_{n7}-NHCO-(CH_2)_{n8}-$, $-NH-(CH_2)_{n5}-(CH_2CH_2O)_{n6}-(CH_2)_{n7}-NHCO-(CH_2)_{n8}-NH-$ or any combination thereof, wherein n5, n6, n7, n8 are each an integer from 0 to 10, optionally, L is $-NH-CH_2-(CH_2CH_2O)_3-(CH_2)_3-NH-$ or $-NH-(CH_2)_{n5}-(CH_2CH_2O)_{n6}-(CH_2)_{n7}-NHCO-(CH_2)_{n8}-$.

5. The peptide compound or the pharmaceutically acceptable salt or solvate of claim 1, wherein the peptide compound is selected from:

Compound 1: Y(aib)EGTFTSDYSIYLDEEAVRLFVNWLIAGGPSSGAPPPS-$NH_2$(SEQ ID NO: 1);

Compound 2: Y(aib)EGTFTSDYSIYLDEEAVKLFVNWLIAGGPSSGAPPPS-$NH_2$(SEQ ID NO: 2);

Compound 4:

(SEQ ID NO: 4)
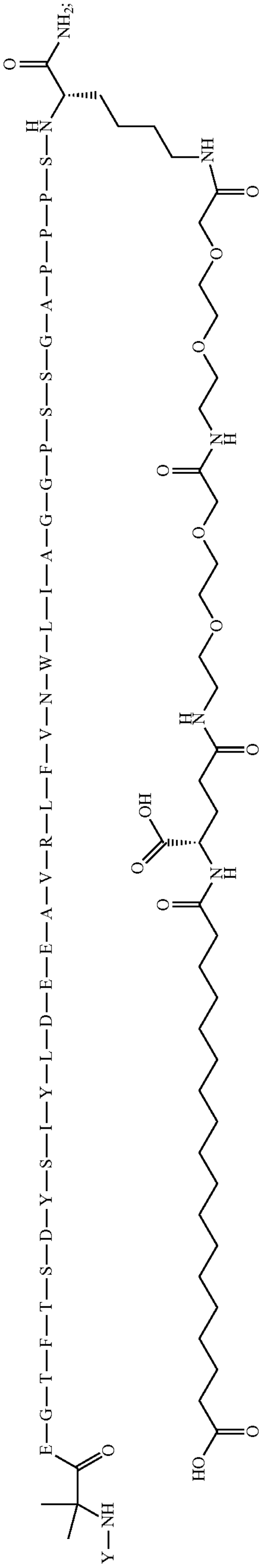

Compound 6:

(SEQ ID NO: 6)
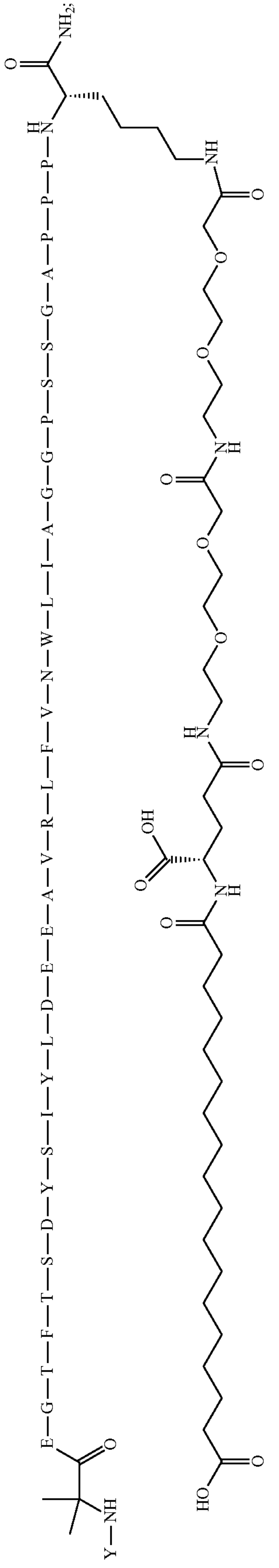

Compound 8: Y(aib)EGTFTSDYSIYLEKEAVRLFVNWLIAGGPSSGAPPPS-$NH_2$ (SEQ ID NO: 8);

Compound 11:

(SEQ ID NO: 11)
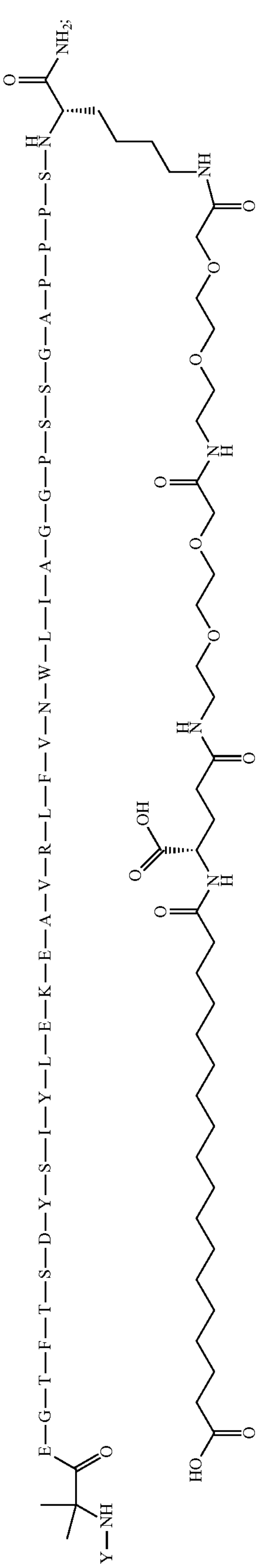

Compound 13:

(SEQ ID NO: 13)
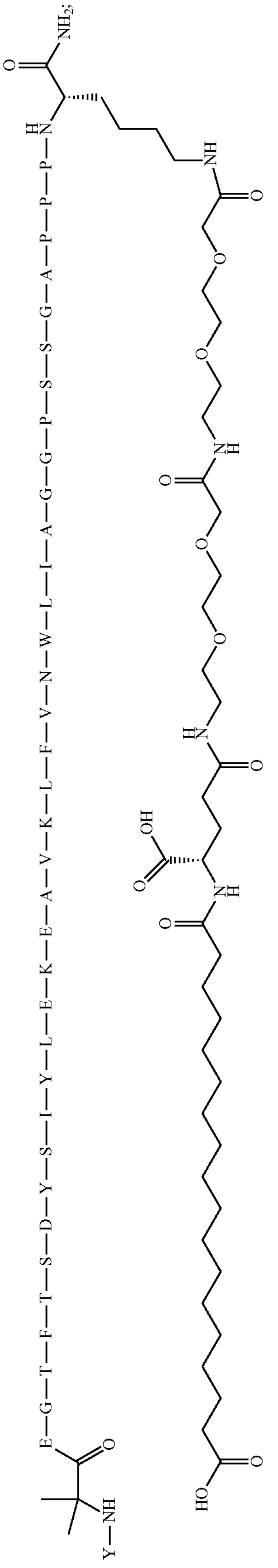

Compound 14:

(SEQ ID NO: 14)
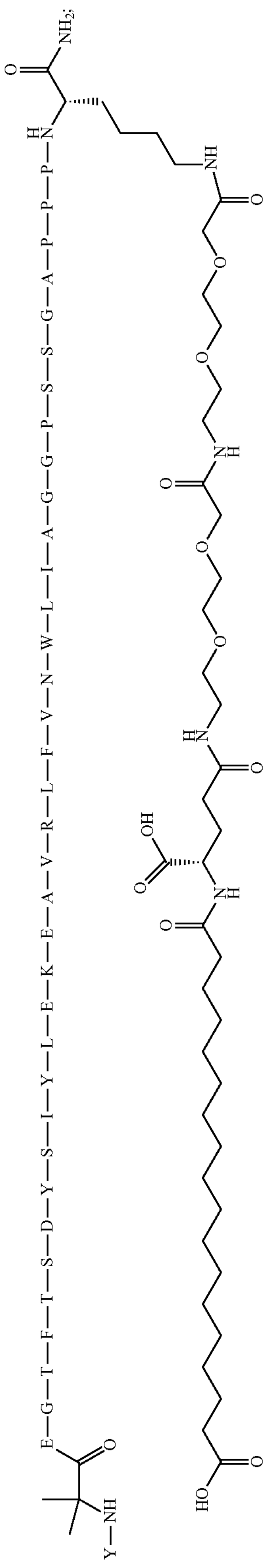

Compound 16: Y(aib) EGTFTSDYSIYLEKEAVRLFIEW-LIAGGPSSGAPPPS-$NH_2$(SEQ ID NO: 16);

Compound 17:

(SEQ ID NO: 17)
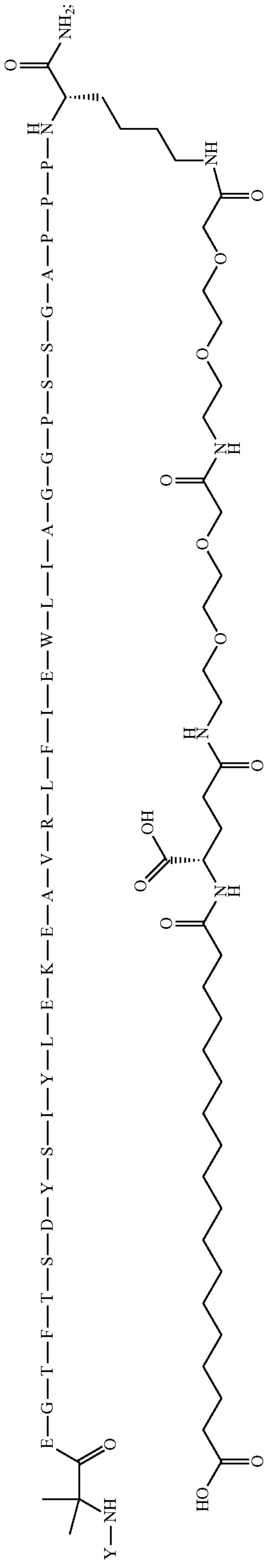

Compound 18: Y(aib)EGTFTSDL-SIQLEKEAARLFIEWLLAGGPSSGAPPPS-$NH_2$ (SEQ ID NO: 18);

Compound 19: Y(aib)EGTFTSDL-SIQLEKEAVRLFIEWLLAGGPSSGAPPPS-$NH_2$ (SEQ ID NO: 19);

Compound 20:

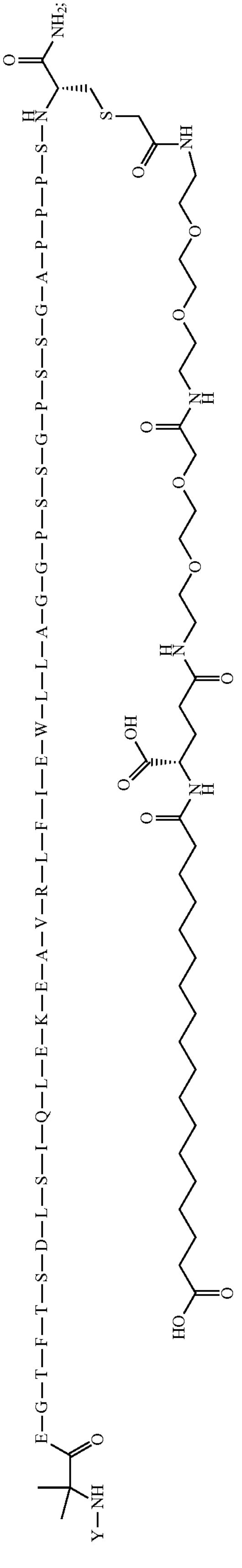
(SEQ ID NO: 20)

Compound 21:

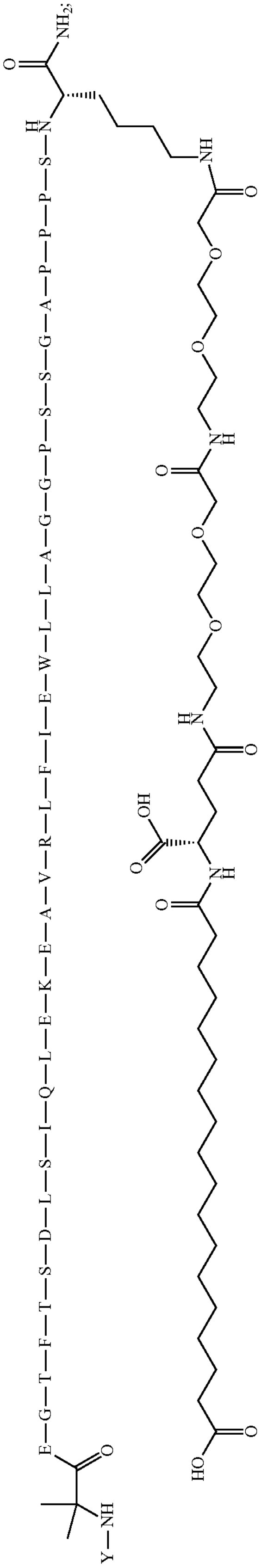
(SEQ ID NO: 21)

Compound 22:

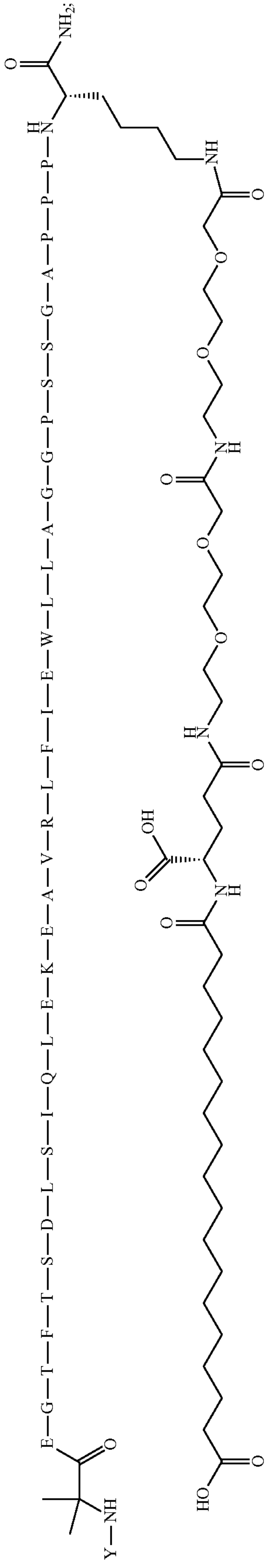
(SEQ ID NO: 22)

Compound 23:

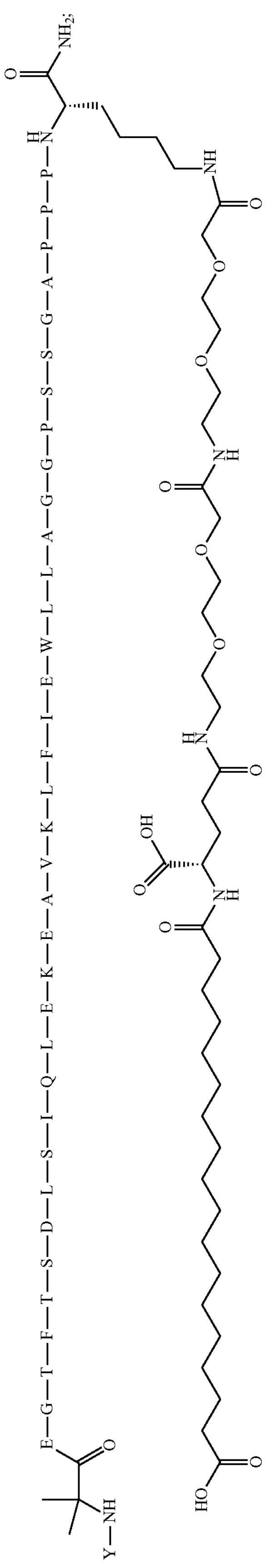
(SEQ ID NO: 23)

Compound 24: Y(aib)EGTFTSDL-SIQLEKEAVKLFIEWLLAGGPSSGAPPPS-$NH_2$ (SEQ ID NO: 24);

Compound 26:

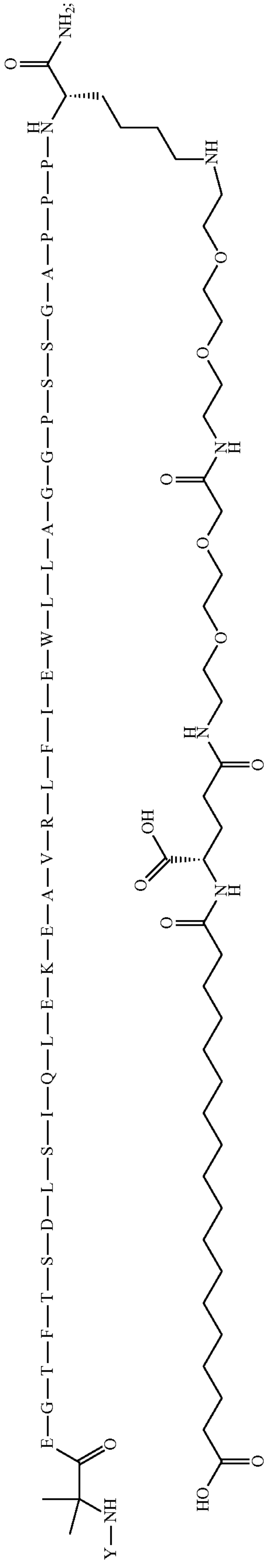
(SEQ ID NO: 26)

Compound 27:

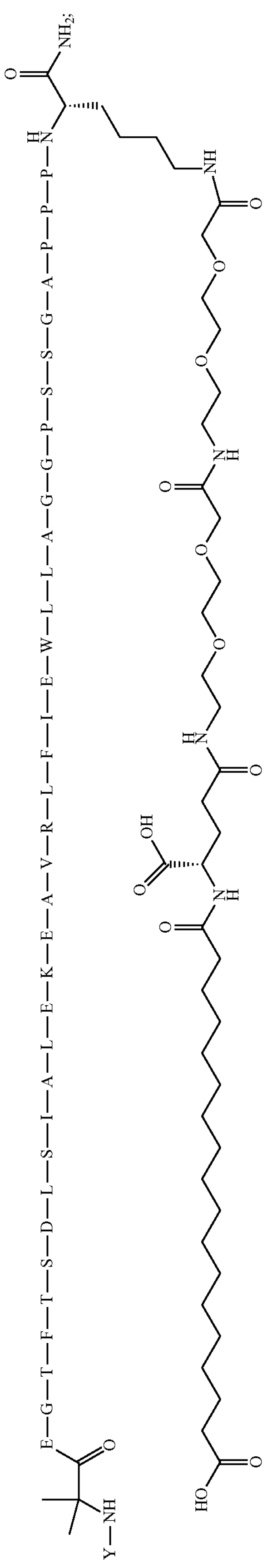
(SEQ ID NO: 27)

Compound 28:

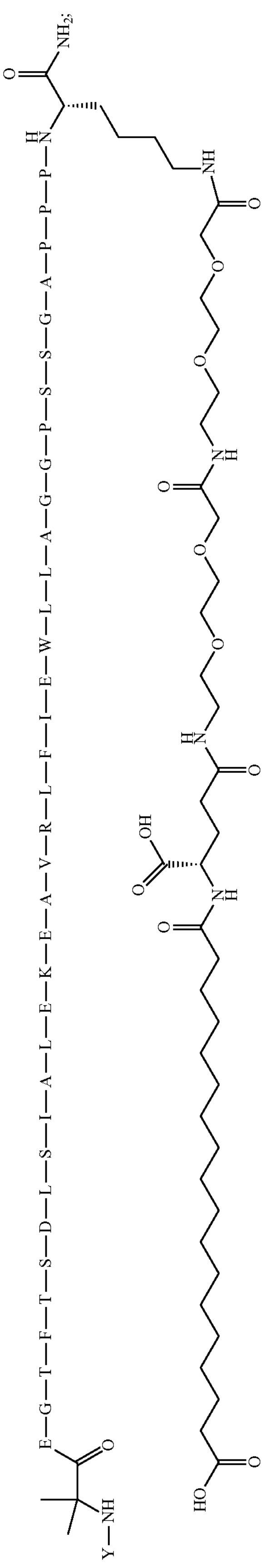
(SEQ ID NO: 28)

Compound 29

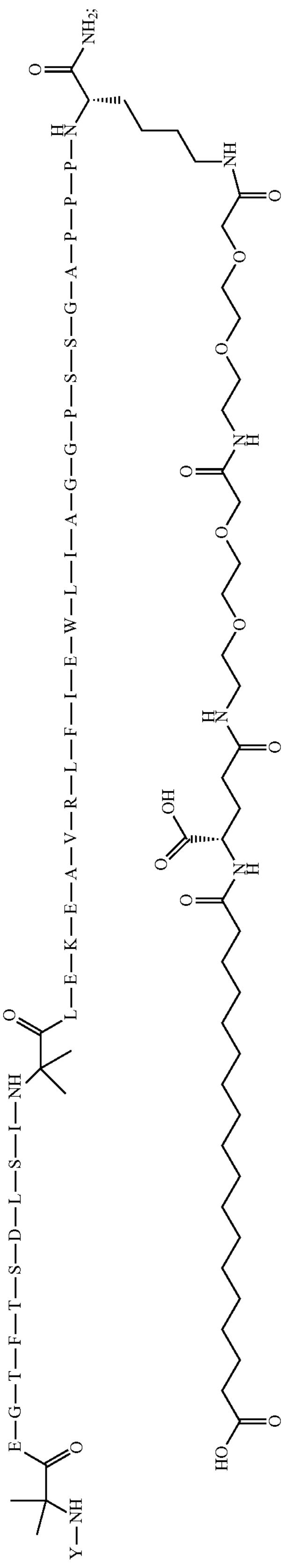
(SEQ ID NO: 29)

Compound 30:

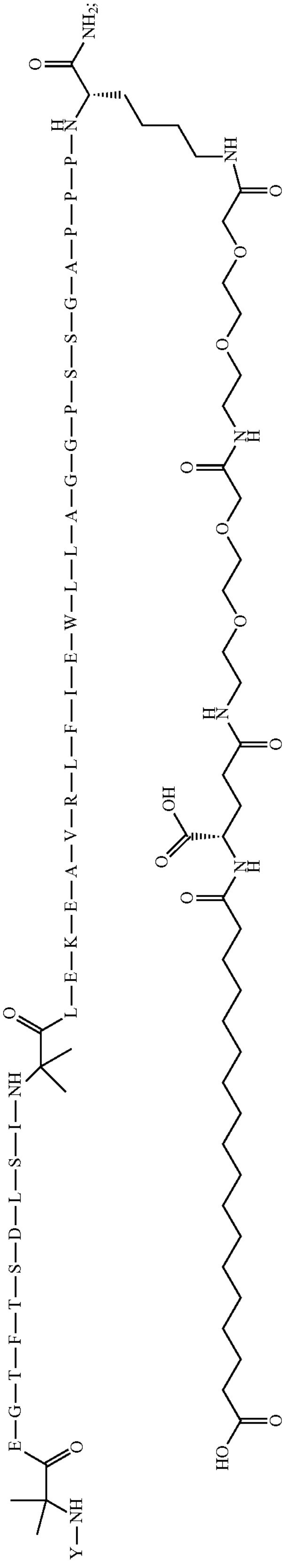
(SEQ ID NO: 30)

Compound 31: Y(aib)EGTFTSDL-SIALEKEAVRLFIEWLLAGGPSSGAPPPS-$NH_2$ (SEQ ID NO: 31);

Compound 35: Y(aib)EGTFTSDL-SIALEKEAVRLFIEWLLAGGPSSGAPPPK-$NH_2$ (SEQ ID NO: 35);

Compound 38: Y(aib)EGTFTSDLSI(aib) LEKEAVRLFIEWLLAGGPSSGAPPPC-$NH_2$(SEQ ID NO: 38);

Compound 40: Y(aib)EGTFTSDLSI(aib) LEKEAVRLFIEWLLAGGPSSGAPPPK-$NH_2$ (SEQ ID NO: 40);

Compound 42: Y(aib)EGTFTSDLSI(aib) LEKEAVRLFIEWLLAG-$NH_2$ (SEQ ID NO:42);

Compound 44: Y(aib)EGTFTSDL-SIALEKEAVKLFIEWLLAGGPSSGAPPPK-$NH_2$ (SEQ ID NO: 44);

Compound 49: Y(aib)EGTFTSDLSI(aib) LEKEAVKLFIEWLLAGGPSSGAPPPK-$NH_2$ (SEQ ID NO: 49);

Compound 115: Y(aib)EGTFTSDLSI(aib) LEKEAVRLFIEWLLAGGPSSGA-$NH_2$ (SEQ ID NO: 115); and Compound 178: Y(aib)EGTFTSDLSI(aib) LEKEAVRLFIEWLLAGGPS-$NH_2$ (SEQ ID NO: 178).

6. A pharmaceutical composition comprising the peptide compound or the pharmaceutically acceptable salt or solvate of claim 1, and a pharmaceutically acceptable carrier or excipient.

7. The peptide compound or the pharmaceutically acceptable salt or solvate of claim 1, wherein the peptide compound has the structure of formula (VII), Y-aib-E-G-T-F-X11-S-D-X1-S-X12-X2-L-X3-X4-E-A-X5-X6-X13-F-X7-X8-W-L-X9-A-G-X10 (VII, SEQ ID NO: 220), wherein X1 is selected from L or Y, X2 is selected from Y or Q, X3 is selected from D or E, X4 is selected from E or K, and X5 is V, X6 is selected from R or K, X7 is selected from I or V, X8 is selected from N or E, X9 is selected from I or L, X10 is GPSSGAPPP (SEQ ID NO: 227), X11 is T; X12 is I; X13 is L;

wherein the serine, cysteine or lysine are added to the C-terminus of X10;

the cysteine or lysine contains a side chain which is modified with a long-acting group;

the long-acting group has the structure of formula (IV):

O1-O2-O3-O4-O5-O6-O7-O8- (IV), wherein O1 has the structure of formula (V) or (VI):

(V)

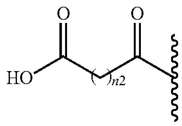

or (VI)

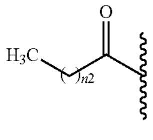

;

wherein n2 is an integer of 10-24;

wherein the wavy line indicates the attachment point to the adjacent group, and O2-O3-O4-O5-O6-O7-O8-represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, and O2 to O8 contain at least one negatively charged moiety.

8. The peptide compound or the pharmaceutically acceptable salt or solvate of claim 1, wherein the peptide compound has the structure of formula (I), Y-aib-E-G-T-F-X11-S-D-X1-S-X12-X2-L-X3-X4-E-A-X5-X6-X13-F-X7-X8-W-L-X9-A-G-X10 (VII, SEQ ID NO: 220), wherein X1 is L, X2 is selected from A or aib, X3 is E, X4 is K, X5 is V, X6 is R, X7 is selected from I or V, X8 is selected from E or N, X9 is selected from I or L, X10 is GPSSGAPPP (SEQ ID NO: 227), X11 is T; X12 is I; X13 is L;

wherein the cysteine or lysine is added to the C-terminus of X10;

optionally, the cysteine or lysine contains a side chain which is modified with a long-acting group;

the long-acting group has the structure of formula (IV):

O1-O2-O3-O4-O5-O6-O7-O8- (IV), wherein O1 has the structure of formula (V) or (VI):

(V)

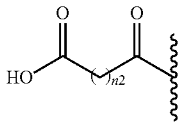

or (VI)

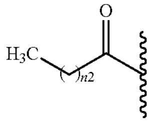

;

wherein n2 is an integer of 10-24;

wherein the wavy line indicates the attachment point to the adjacent group, and O2-O3-O4-O5-O6-O7-O8-represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, and O2 to O8 contain at least one negatively charged moiety.

9. The peptide compound or the pharmaceutically acceptable salt or solvate of claim 1, wherein the peptide compound has the structure of formula (VII), Y-aib-E-G-T-F-X11-S-D-X1-S-X12-X2-L-X3-X4-E-A-X5-X6-X13-F-X7-X8-W-L-X9-A-G-X10 (VII, SEQ ID NO: 220), wherein X1 is L, X2 is selected from A or Aib, X3 is E, X4 is K, X5 is V, X6 is R, X7 is I, X8 is E, X9 is L, X10 is GPSSGAPPP (SEQ ID NO: 227), X11 is T; X12 is I; X13 is L;

wherein the lysine is added to the C-terminus of X10;

the lysine contains a side chain amino group which is modified with a long-acting group;

the long-acting group has the structure of formula (IV):

O1-O2-O3-O4-O5-O6-O7-O8- (IV), wherein O1 has the structure of formula (V) or (VI):

(V)

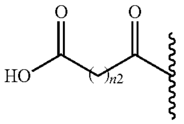

or (VI)

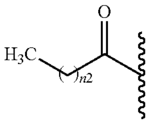

;

wherein n2 is an integer of 10-24;

wherein the wavy line indicates the attachment point to the amino group of the adjacent group, and O2-O3-O4-O5-O6-O7-O8- represents a linker, wherein each of O2 to O8 is independently selected from any one of the following amino acid residues or long chain structures: α-Glu, γ-Glu, α-Asp, β-Asp, α-hGlu, δ-hGlu, Gly, Ala, β-Ala, GABA or PEG2, or one or more residues O2 to O8 are absent, provided that at least two residues O2 to O8 are present, and O2 to O8 contain at least one negatively charged moiety.

* * * * *

SEQUENCE LISTING

<160> NUMBER OF SEQ ID NOS: 238

<210> SEQ ID NO 1
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 1

```
Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro Pro Ser
        35
```

<210> SEQ ID NO 2
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 2

```
Tyr Xaa Glu Gly Thr Phe Thr Ser Asp Tyr Ser Ile Tyr Leu Asp Glu
1               5                   10                  15

Glu Ala Val Lys Leu Phe Val Asn Trp Leu Ile Ala Gly Gly Pro Ser
            20                  25                  30

Ser Gly Ala Pro Pro Pro Ser
        35
```

<210> SEQ ID NO 3
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 3

```
Tyr Xaa Glu Gly Thr Phe Thr Ser Asp Tyr Ser Ile Tyr Leu Asp Glu
1               5                   10                  15

Glu Ala Val Lys Leu Phe Val Gln Trp Leu Ile Ala Gly Gly Pro Ser
            20                  25                  30
```

```
Ser Gly Ala Pro Pro Pro Ser
        35


<210> SEQ ID NO 4
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 4

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro Pro Ser Lys
        35                  40


<210> SEQ ID NO 5
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 5

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro Pro Ser Cys
        35                  40


<210> SEQ ID NO 6
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Lys = modified Lys;
```

-continued

Lys([(2-(2-(2-aminoethoxy)ethoxy)acetoly)2]-[gammaglutamicacid]-
[17-carboxyheptadecanoyl])
<220> FEATURE:
<221> NAME/KEY: MOD_RES
<222> LOCATION: (39)..(39)
<223> OTHER INFORMATION: AMIDATION, C-termianl amidation

<400> SEQUENCE: 6

Tyr Xaa Glu Gly Thr Phe Thr Ser Asp Tyr Ser Ile Tyr Leu Asp Glu
1 5 10 15

Glu Ala Val Arg Leu Phe Val Asn Trp Leu Ile Ala Gly Gly Pro Ser
20 25 30

Ser Gly Ala Pro Pro Pro Lys
35

<210> SEQ ID NO 7
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 7

Tyr Xaa Glu Gly Thr Phe Thr Ser Asp Tyr Ser Ile Tyr Leu Asp Glu
1 5 10 15

Glu Ala Val Lys Leu Phe Val Asn Trp Leu Ile Ala Gly
20 25

<210> SEQ ID NO 8
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 8

Tyr Xaa Glu Gly Thr Phe Thr Ser Asp Tyr Ser Ile Tyr Leu Glu Lys
1 5 10 15

Glu Ala Val Arg Leu Phe Val Asn Trp Leu Ile Ala Gly Gly Pro Ser
20 25 30

Ser Gly Ala Pro Pro Pro Ser
35

<210> SEQ ID NO 9
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)

```
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 9

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro Pro Pro Ser
        35


<210> SEQ ID NO 10
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 10

Tyr Xaa Glu Gly Thr Phe Thr Ser Asp Tyr Ser Ile Tyr Leu Glu Lys
1               5                   10                  15

Glu Ala Ala Lys Leu Phe Val Asn Trp Leu Ile Ala Gly Gly Pro Ser
            20                  25                  30

Ser Gly Ala Pro Pro Pro Ser
        35


<210> SEQ ID NO 11
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 11

Tyr Xaa Glu Gly Thr Phe Thr Ser Asp Tyr Ser Ile Tyr Leu Glu Lys
1               5                   10                  15

Glu Ala Val Arg Leu Phe Val Asn Trp Leu Ile Ala Gly Gly Pro Ser
            20                  25                  30

Ser Gly Ala Pro Pro Pro Ser Lys
        35                  40


<210> SEQ ID NO 12
```

```
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 12

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro Pro Pro Lys
        35


<210> SEQ ID NO 13
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (39)..(39)
<223> OTHER INFORMATION: AMIDATION, C-termianl amidation

<400> SEQUENCE: 13

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro Pro Pro Lys
        35


<210> SEQ ID NO 14
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (39)..(39)
<223> OTHER INFORMATION: AMIDATION, C-termianl amidation
```

<400> SEQUENCE: 14

```
Tyr Xaa Glu Gly Thr Phe Thr Ser Asp Tyr Ser Ile Tyr Leu Glu Lys
1               5                   10                  15

Glu Ala Val Arg Leu Phe Val Asn Trp Leu Ile Ala Gly Gly Pro Ser
            20                  25                  30

Ser Gly Ala Pro Pro Pro Lys
        35
```

<210> SEQ ID NO 15
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 15

```
Tyr Xaa Glu Gly Thr Phe Thr Ser Asp Tyr Ser Ile Tyr Leu Glu Lys
1               5                   10                  15

Glu Ala Val Arg Leu Phe Val Asn Trp Leu Leu Ala Gly
            20                  25
```

<210> SEQ ID NO 16
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 16

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro Ser
        35
```

<210> SEQ ID NO 17
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
Lys([(2-(2-(2-aminoethoxy)ethoxy)acetoly)2]-[gammaglutamicacid]-

[17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 17

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro Ser Lys
        35                  40
```

<210> SEQ ID NO 18
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 18

```
Tyr Xaa Glu Gly Thr Phe Thr Ser Asp Leu Ser Ile Gln Leu Glu Lys
1               5                   10                  15

Glu Ala Ala Arg Leu Phe Ile Glu Trp Leu Leu Ala Gly Gly Pro Ser
            20                  25                  30

Ser Gly Ala Pro Pro Pro Ser
        35
```

<210> SEQ ID NO 19
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 19

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser
        35
```

<210> SEQ ID NO 20
<211> LENGTH: 40
<212> TYPE: PRT
<213> ORGANISM: Artificial Sequence
<220> FEATURE:
<223> OTHER INFORMATION: synthetic peptide
<220> FEATURE:

```
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Cys= modified Cys;
      Cys([2-(2-(2-aminoethoxy)ethoxy)ethylacetamido]-[2-(2-(2-
      aminoethoxy)ethoxy)acetoly]-[gammaglutamicacid]-[17-
      carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 20

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Cys
        35                  40


<210> SEQ ID NO 21
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 21

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Lys
        35                  40


<210> SEQ ID NO 22
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (39)..(39)
```

<223> OTHER INFORMATION: AMIDATION, C-termianl amidation

<400> SEQUENCE: 22

Tyr Xaa Glu Gly Thr Phe Thr Ser Asp Leu Ser Ile Gln Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Lys
35

<210> SEQ ID NO 23
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
Lys([(2-(2-(2-aminoethoxy)ethoxy)acetoly)2]-[gammaglutamicacid]-
[17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 23

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

Ser Gly Ala Pro Pro Pro Ser Lys
35 40

<210> SEQ ID NO 24
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 24

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

Ser Gly Ala Pro Pro Pro Ser
35

<210> SEQ ID NO 25
<211> LENGTH: 29
<212> TYPE: PRT
<213> ORGANISM: Artificial Sequence
<220> FEATURE:

-continued

```
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 25

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly
            20                  25


<210> SEQ ID NO 26
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Cys= modified Cys;
      Cys([2-(2-(2-aminoethoxy)ethoxy)ethylacetamido]-[2-(2-(2-
      aminoethoxy)ethoxy)acetoly]-[gammaglutamicacid]-[17-
      carboxyheptadecanoyl])
<220> FEATURE:
<221> NAME/KEY: MOD_RES
<222> LOCATION: (39)..(39)
<223> OTHER INFORMATION: AMIDATION, C-termianl amidation

<400> SEQUENCE: 26

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Cys
        35


<210> SEQ ID NO 27
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (39)..(39)
<223> OTHER INFORMATION: AMIDATION, C-termianl amidation

<400> SEQUENCE: 27

Tyr Xaa Glu Gly Thr Phe Thr Ser Asp Leu Ser Ile Ala Leu Glu Lys
1               5                   10                  15
```

-continued

```
Glu Ala Val Arg Leu Phe Ile Glu Trp Leu Leu Ala Gly Gly Pro Ser
            20                  25                  30

Ser Gly Ala Pro Pro Pro Lys
        35


<210> SEQ ID NO 28
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 28

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Lys
        35                  40


<210> SEQ ID NO 29
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (39)..(39)
<223> OTHER INFORMATION: AMIDATION, C-termianl amidation

<400> SEQUENCE: 29

Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Lys
        35


<210> SEQ ID NO 30
<211> LENGTH: 40
```

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (40)..(40)
<223> OTHER INFORMATION: C-termianl Lys = modified Lys;
      Lys([(2-(2-(2-aminoethoxy)ethoxy)acetoly)2]-[gammaglutamicacid]-
      [17-carboxyheptadecanoyl])
<220> FEATURE:
<221> NAME/KEY: MOD_RES
<222> LOCATION: (40)..(40)
<223> OTHER INFORMATION: AMIDATION, C-termianl amidation

<400> SEQUENCE: 30

Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Lys
        35                  40


<210> SEQ ID NO 31
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 31

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser
        35


<210> SEQ ID NO 32
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 32
```

```
Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Cys
        35                  40


<210> SEQ ID NO 33
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 33

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Cys
        35


<210> SEQ ID NO 34
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 34

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Lys
        35                  40


<210> SEQ ID NO 35
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation
```

<400> SEQUENCE: 35

Tyr Xaa Glu Gly Thr Phe Thr Ser Asp Leu Ser Ile Ala Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Lys
35

<210> SEQ ID NO 36
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 36

Tyr Xaa Glu Gly Thr Phe Thr Ser Asp Leu Ser Ile Xaa Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Ser
35

<210> SEQ ID NO 37
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 37

Tyr Xaa Glu Gly Thr Phe Thr Ser Asp Leu Ser Ile Xaa Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Ser Cys
35 40

<210> SEQ ID NO 38
<211> LENGTH: 39
<212> TYPE: PRT
<213> ORGANISM: Artificial Sequence
<220> FEATURE:

<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 38

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Cys
        35
```

<210> SEQ ID NO 39
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 39

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Lys
        35                  40
```

<210> SEQ ID NO 40
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 40

```
Tyr Xaa Glu Gly Thr Phe Thr Ser Asp Leu Ser Ile Xaa Leu Glu Lys
```

```
1               5                   10                  15

Glu Ala Val Arg Leu Phe Ile Glu Trp Leu Leu Ala Gly Gly Pro Ser
            20                  25                  30

Ser Gly Ala Pro Pro Pro Lys
        35


<210> SEQ ID NO 41
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 41

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly
            20                  25


<210> SEQ ID NO 42
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 42

Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly
            20                  25


<210> SEQ ID NO 43
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 43

Tyr Xaa Glu Gly Thr Phe Thr Ser Asp Leu Ser Ile Ala Leu Glu Lys
```

```
1               5                   10                  15

Glu Ala Val Lys Leu Phe Ile Glu Trp Leu Leu Ala Gly Gly Pro Ser
            20                  25                  30

Ser Gly Ala Pro Pro Pro Ser
        35


<210> SEQ ID NO 44
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 44

Tyr Xaa Glu Gly Thr Phe Thr Ser Asp Leu Ser Ile Ala Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Lys
        35


<210> SEQ ID NO 45
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 45

Tyr Xaa Glu Gly Thr Phe Thr Ser Asp Leu Ser Ile Ala Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Ser Lys
        35                  40


<210> SEQ ID NO 46
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: METHYLATION
<222> LOCATION: (40)..(40)
<223> OTHER INFORMATION: AMIDATION, C-termianl amidation

<400> SEQUENCE: 46
```

```
Tyr Xaa Glu Gly Thr Phe Thr Ser Asp Leu Ser Ile Ala Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Ser Cys
        35                  40


<210> SEQ ID NO 47
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 47

Tyr Xaa Glu Gly Thr Phe Thr Ser Asp Leu Ser Ile Ala Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Cys
        35


<210> SEQ ID NO 48
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 48

Tyr Xaa Glu Gly Thr Phe Thr Ser Asp Leu Ser Ile Xaa Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Ser
        35


<210> SEQ ID NO 49
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (2)..(2)
<223> OTHER INFORMATION: X=aminoisobutyric aicd
```

<220> FEATURE:
<221> NAME/KEY: METHYLATION
<222> LOCATION: (13)..(13)
<223> OTHER INFORMATION: X=aminoisobutyric aicd
<220> FEATURE:
<221> NAME/KEY: METHYLATION
<222> LOCATION: (39)..(39)
<223> OTHER INFORMATION: AMIDATION, C-termianl amidation

<400> SEQUENCE: 49

Tyr Xaa Glu Gly Thr Phe Thr Ser Asp Leu Ser Ile Xaa Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Lys
        35

<210> SEQ ID NO 50
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 50

Tyr Xaa Glu Gly Thr Phe Thr Ser Asp Leu Ser Ile Xaa Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Ser Lys
        35                  40

<210> SEQ ID NO 51
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 51

Tyr Xaa Glu Gly Thr Phe Thr Ser Asp Leu Ser Ile Xaa Leu Glu Lys
1               5                   10                  15

Glu Ala Val Lys Leu Phe Ile Glu Trp Leu Leu Ala Gly Gly Pro Ser
            20                  25                  30

```
Ser Gly Ala Pro Pro Pro Cys
        35


<210> SEQ ID NO 52
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 52

Tyr Xaa Glu Gly Thr Phe Thr Ser Asp Leu Ser Ile Xaa Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Ser Cys
        35                  40


<210> SEQ ID NO 53
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 53

Tyr Xaa Glu Gly Thr Phe Thr Ser Asp Leu Ser Ile Gln Leu Glu Lys
1               5                   10                  15

Glu Ala Val Arg Leu Phe Val Asn Trp Leu Leu Ala Gly Gly Pro Ser
            20                  25                  30

Ser Gly Ala Pro Pro Pro Ser
        35


<210> SEQ ID NO 54
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 54
```

-continued

```
Tyr Xaa Glu Gly Thr Phe Thr Ser Asp Leu Ser Ile Ala Leu Glu Lys
1               5                   10                  15

Glu Ala Val Arg Leu Phe Val Asn Trp Leu Leu Ala Gly Gly Pro Ser
            20                  25                  30

Ser Gly Ala Pro Pro Pro Lys
        35


<210> SEQ ID NO 55
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 55

Tyr Xaa Glu Gly Thr Phe Thr Ser Asp Leu Ser Ile Xaa Leu Glu Lys
1               5                   10                  15

Glu Ala Val Arg Leu Phe Val Asn Trp Leu Leu Ala Gly Gly Pro Ser
            20                  25                  30

Ser Gly Ala Pro Pro Pro Cys
        35


<210> SEQ ID NO 56
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 56

Tyr Xaa Glu Gly Thr Phe Thr Ser Asp Leu Ser Ile Xaa Leu Glu Lys
1               5                   10                  15

Glu Ala Val Arg Leu Phe Val Asn Trp Leu Leu Ala Gly Gly Pro Ser
            20                  25                  30

Ser Gly Ala Pro Pro Pro Lys
        35


<210> SEQ ID NO 57
<211> LENGTH: 39
<212> TYPE: PRT
<213> ORGANISM: Artificial Sequence
<220> FEATURE:
<223> OTHER INFORMATION: synthetic peptide
<220> FEATURE:
```

<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 57

Tyr Xaa Glu Gly Thr Phe Thr Ser Asp Tyr Ser Ile Tyr Leu Asp Glu
1 5 10 15

Glu Ala Val Arg Leu Phe Ile Glu Trp Leu Ile Ala Gly Gly Pro Ser
20 25 30

Ser Gly Ala Pro Pro Pro Lys
35

<210> SEQ ID NO 58
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 58

Tyr Xaa Glu Gly Thr Phe Thr Ser Asp Leu Ser Ile Gln Leu Glu Lys
1 5 10 15

Glu Ala Val Arg Leu Phe Val Asn Trp Leu Leu Ala Gly Gly Pro Ser
20 25 30

Ser Gly Ala Pro Pro Pro Ser
35

<210> SEQ ID NO 59
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 59

Tyr Xaa Glu Gly Thr Phe Thr Ser Asp Leu Ser Ile Ala Leu Glu Lys
1 5 10 15

Glu Ala Val Arg Leu Phe Val Asn Trp Leu Leu Ala Gly Gly Pro Ser
20 25 30

Ser Gly Ala Pro Pro Pro Ser
35

<210> SEQ ID NO 60
<211> LENGTH: 39
<212> TYPE: PRT
<213> ORGANISM: Artificial Sequence
<220> FEATURE:

<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 60

```
Tyr Xaa Glu Gly Thr Phe Thr Ser Asp Leu Ser Ile Xaa Leu Glu Lys
1               5                   10                  15

Glu Ala Val Arg Leu Phe Val Asn Trp Leu Leu Ala Gly Gly Pro Ser
            20                  25                  30

Ser Gly Ala Pro Pro Pro Ser
        35
```

<210> SEQ ID NO 61
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 61

```
Tyr Xaa Glu Gly Thr Phe Thr Ser Asp Tyr Ser Ile Tyr Leu Asp Glu
1               5                   10                  15

Glu Ala Val Arg Leu Phe Ile Glu Trp Leu Ile Ala Gly Gly Pro Ser
            20                  25                  30

Ser Gly Ala Pro Pro Pro Ser
        35
```

<210> SEQ ID NO 62
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 62

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Cys
        35                  40
```

<210> SEQ ID NO 63
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 63

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Cys
        35
```

<210> SEQ ID NO 64
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 64

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser Lys
        35                  40
```

<210> SEQ ID NO 65
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 65

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Lys
```

35

<210> SEQ ID NO 66
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 66

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

Ser Gly Ala Pro Pro Pro Ser Cys
35 40

<210> SEQ ID NO 67
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 67

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

Ser Gly Ala Pro Pro Pro Cys
35

<210> SEQ ID NO 68
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 68

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

```
Ser Gly Ala Pro Pro Pro Ser Lys
        35                  40


<210> SEQ ID NO 69
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 69

Tyr Xaa Glu Gly Thr Phe Thr Ser Asp Leu Ser Ile Gln Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro Pro Lys
        35


<210> SEQ ID NO 70
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 70

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro Pro Ser Lys
        35                  40


<210> SEQ ID NO 71
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 71

Tyr Xaa Glu Gly Thr Phe Thr Ser Asp Tyr Ser Ile Tyr Leu Asp Glu
1               5                   10                  15
```

-continued

```
Glu Ala Val Lys Leu Phe Val Asn Trp Leu Ile Ala Gly Gly Pro Ser
            20                  25                  30

Ser Gly Ala Pro Pro Pro Ser Lys
        35                  40


<210> SEQ ID NO 72
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 72

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro Pro Lys
        35


<210> SEQ ID NO 73
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 73

Tyr Xaa Glu Gly Thr Phe Thr Ser Asp Tyr Ser Ile Tyr Leu Asp Glu
1               5                   10                  15

Glu Ala Val Lys Leu Phe Val Asn Trp Leu Ile Ala Gly Gly Pro Ser
            20                  25                  30

Ser Gly Ala Pro Pro Pro Lys
        35


<210> SEQ ID NO 74
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 74

Tyr Xaa Glu Gly Thr Phe Thr Ser Asp Tyr Ser Ile Tyr Leu Asp Glu
```

-continued

```
1               5                   10                  15

Glu Ala Val Lys Leu Phe Val Asn Trp Leu Ile Ala Gly Gly Pro Ser
            20                  25                  30

Ser Gly Ala Pro Pro Pro Ser Cys
        35                  40


<210> SEQ ID NO 75
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 75

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro Pro Cys
        35


<210> SEQ ID NO 76
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 76

Tyr Xaa Glu Gly Thr Phe Thr Ser Asp Tyr Ser Ile Tyr Leu Asp Glu
1               5                   10                  15

Glu Ala Val Lys Leu Phe Val Asn Trp Leu Ile Ala Gly Gly Pro Ser
            20                  25                  30

Ser Gly Ala Pro Pro Pro Cys
        35


<210> SEQ ID NO 77
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 77
```

```
Tyr Xaa Glu Gly Thr Phe Thr Ser Asp Tyr Ser Ile Tyr Leu Glu Lys
1               5                   10                  15

Glu Ala Val Arg Leu Phe Val Asn Trp Leu Ile Ala Gly Gly Pro Ser
            20                  25                  30

Ser Gly Ala Pro Pro Pro Ser Lys
        35                  40


<210> SEQ ID NO 78
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 78

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro Pro Pro Ser Lys
        35                  40


<210> SEQ ID NO 79
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 79

Tyr Xaa Glu Gly Thr Phe Thr Ser Asp Tyr Ser Ile Tyr Leu Glu Lys
1               5                   10                  15

Glu Ala Val Arg Leu Phe Val Asn Trp Leu Ile Ala Gly Gly Pro Ser
            20                  25                  30

Ser Gly Ala Pro Pro Pro Lys
        35


<210> SEQ ID NO 80
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation
```

<400> SEQUENCE: 80

Tyr Xaa Glu Gly Thr Phe Thr Ser Asp Tyr Ser Ile Tyr Leu Glu Lys
1 5 10 15

Glu Ala Val Arg Leu Phe Val Asn Trp Leu Ile Ala Gly Gly Pro Ser
20 25 30

Ser Gly Ala Pro Pro Pro Ser Cys
35 40

<210> SEQ ID NO 81
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 81

Tyr Xaa Glu Gly Thr Phe Thr Ser Asp Tyr Ser Ile Tyr Leu Glu Lys
1 5 10 15

Glu Ala Val Lys Leu Phe Val Asn Trp Leu Ile Ala Gly Gly Pro Ser
20 25 30

Ser Gly Ala Pro Pro Pro Ser Cys
35 40

<210> SEQ ID NO 82
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 82

Tyr Xaa Glu Gly Thr Phe Thr Ser Asp Tyr Ser Ile Tyr Leu Glu Lys
1 5 10 15

Glu Ala Val Arg Leu Phe Val Asn Trp Leu Ile Ala Gly Gly Pro Ser
20 25 30

Ser Gly Ala Pro Pro Pro Cys
35

<210> SEQ ID NO 83
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 83

```
Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro Pro Pro Cys
        35
```

<210> SEQ ID NO 84
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (40)..(40)
<223> OTHER INFORMATION: AMIDATION, C-termianl amidation

<400> SEQUENCE: 84

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro Ser Lys
        35                  40
```

<210> SEQ ID NO 85
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 85

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro Lys
        35
```

<210> SEQ ID NO 86
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd -continued

```
<220> FEATURE:
<221> NAME/KEY: MOD_RES
<222> LOCATION: (40)..(40)
<223> OTHER INFORMATION: AMIDATION, C-termianl amidation

<400> SEQUENCE: 86

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro Ser Cys
        35                  40


<210> SEQ ID NO 87
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 87

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro Cys
        35


<210> SEQ ID NO 88
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 88

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly
            20                  25


<210> SEQ ID NO 89
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
```

```
<221> NAME/KEY: MOD_RES
<222> LOCATION: (29)..(29)
<223> OTHER INFORMATION: AMIDATION, C-termianl amidation

<400> SEQUENCE: 89

Tyr Xaa Glu Gly Thr Phe Thr Ser Asp Leu Ser Ile Gln Leu Glu Lys
1               5                   10                  15

Glu Ala Val Arg Leu Phe Val Asn Trp Leu Leu Ala Gly
            20                  25


<210> SEQ ID NO 90
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 90

Tyr Xaa Glu Gly Thr Phe Thr Ser Asp Leu Ser Ile Ala Leu Glu Lys
1               5                   10                  15

Glu Ala Val Arg Leu Phe Val Asn Trp Leu Leu Ala Gly
            20                  25


<210> SEQ ID NO 91
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (29)..(29)
<223> OTHER INFORMATION: AMIDATION, C-termianl amidation

<400> SEQUENCE: 91

Tyr Xaa Glu Gly Thr Phe Thr Ser Asp Leu Ser Ile Xaa Leu Glu Lys
1               5                   10                  15

Glu Ala Val Arg Leu Phe Val Asn Trp Leu Leu Ala Gly
            20                  25


<210> SEQ ID NO 92
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation
```

<400> SEQUENCE: 92

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala
        35
```

<210> SEQ ID NO 93
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 93

```
Tyr Xaa Glu Gly Thr Phe Thr Ser Asp Tyr Ser Ile Tyr Leu Asp Glu
1               5                   10                  15

Glu Ala Val Arg Leu Phe Ile Glu Trp Leu Ile Ala Gly Gly Pro Ser
            20                  25                  30

Ser Gly Ala Pro Pro Pro Ser
        35
```

<210> SEQ ID NO 94
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 94

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro
        35
```

<210> SEQ ID NO 95
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 95

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro
        35

<210> SEQ ID NO 96
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 96

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala Pro Pro
        35

<210> SEQ ID NO 97
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 97

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro
        35

<210> SEQ ID NO 98
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 98

Tyr Xaa Glu Gly Thr Phe Thr Ser Asp Tyr Ser Ile Tyr Leu Glu Lys
1               5                   10                  15

Glu Ala Val Arg Leu Phe Ile Ala Trp Leu Leu Ala Gly Gly Pro Ser
            20                  25                  30

Ser Gly Ala Pro Pro Pro Ser
        35

<210> SEQ ID NO 99
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 99

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly
            20                  25                  30

<210> SEQ ID NO 100
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 100

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala Pro
        35

<210> SEQ ID NO 101
<211> LENGTH: 39
<212> TYPE: PRT
<213> ORGANISM: Artificial Sequence
<220> FEATURE:
<223> OTHER INFORMATION: synthetic peptide
<220> FEATURE:

```
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 101

Tyr Xaa Glu Gly Thr Phe Thr Ser Asp Leu Ser Lys Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser
        35


<210> SEQ ID NO 102
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 102

Tyr Xaa Glu Gly Thr Phe Thr Ser Asp Tyr Ser Ile Tyr Leu Glu Lys
1               5                   10                  15

Glu Ala Val Lys Leu Phe Ile Glu Trp Leu Ile Ala Gly Gly Pro Ser
            20                  25                  30

Ser Gly Ala Pro Pro Pro Ser
        35


<210> SEQ ID NO 103
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 103

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly Ala
        35


<210> SEQ ID NO 104
<211> LENGTH: 39
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 104

Tyr Xaa Glu Gly Thr Phe Thr Ser Asp Leu Ser Ile Gln Leu Glu Lys
1               5                   10                  15

Glu Ala Val Lys Glu Phe Ile Ala Trp Leu Ile Ala Gly Gly Pro Ser
            20                  25                  30

Ser Gly Ala Pro Pro Pro Ser
        35


<210> SEQ ID NO 105
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 105

Tyr Xaa Glu Gly Thr Phe Thr Ser Asp Tyr Ser Ile Tyr Leu Asp Glu
1               5                   10                  15

Glu Ala Val Arg Leu Phe Ile Ala Trp Leu Ile Ala Gly Gly Pro Ser
            20                  25                  30

Ser Gly Ala Pro Pro Pro Ser
        35


<210> SEQ ID NO 106
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 106

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly
            20                  25                  30


<210> SEQ ID NO 107
<211> LENGTH: 39
<212> TYPE: PRT
<213> ORGANISM: Artificial Sequence
<220> FEATURE:
<223> OTHER INFORMATION: synthetic peptide
```

<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 107

Tyr Xaa Glu Gly Thr Phe Thr Ser Asp Leu Ser Ile Ala Leu Glu Lys
1 5 10 15

Glu Ala Val Arg Leu Phe Val Asn Trp Leu Ile Ala Gly Gly Pro Ser
20 25 30

Ser Gly Ala Pro Pro Pro Ser
35

<210> SEQ ID NO 108
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 108

Tyr Xaa Glu Gly Thr Phe Thr Ser Asp Tyr Ser Ile Tyr Leu Asp Glu
1 5 10 15

Glu Ala Val Arg Leu Phe Val Asn Trp Leu Ile Ala Gly Gly Pro Ser
20 25 30

Ser Gly Ala Pro
35

<210> SEQ ID NO 109
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 109

Tyr Xaa Glu Gly Thr Phe Thr Ser Asp Tyr Ser Ile Tyr Leu Glu Lys
1 5 10 15

Glu Ala Val Lys Leu Phe Val Asn Trp Leu Ile Ala Gly Gly Pro Ser
20 25 30

Ser Gly

<210> SEQ ID NO 110
<211> LENGTH: 35
<212> TYPE: PRT
<213> ORGANISM: Artificial Sequence
<220> FEATURE:

<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 110

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser Gly Ala
        35
```

<210> SEQ ID NO 111
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 111

```
Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala
        35
```

<210> SEQ ID NO 112
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 112

```
Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro
            20                  25                  30
```

<210> SEQ ID NO 113
<211> LENGTH: 38
<212> TYPE: PRT
<213> ORGANISM: Artificial Sequence
<220> FEATURE:
<223> OTHER INFORMATION: synthetic peptide

```
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 113

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Leu Ala Gly Gly Pro Ser
            20                  25                  30

Ser Gly Ala Pro Pro Pro
        35


<210> SEQ ID NO 114
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 114

Tyr Xaa Glu Gly Thr Phe Thr Ser Asp Leu Ser Ile Gln Leu Glu Lys
1               5                   10                  15

Glu Ala Val Arg Leu Phe Val Asn Trp Leu Ile Ala Gly Gly Pro Ser
            20                  25                  30

Ser Gly Ala Pro Pro Pro Ser
        35


<210> SEQ ID NO 115
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 115

Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala
        35
```

<210> SEQ ID NO 116
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 116

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30

Ser
```

<210> SEQ ID NO 117
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 117

```
Tyr Xaa Glu Gly Thr Phe Thr Ser Asp Leu Ser Ile Gln Leu Glu Lys
1               5                   10                  15

Glu Ala Val Arg Leu Phe Ile Ala Trp Leu Ile Ala Gly Gly Pro Ser
            20                  25                  30

Ser Gly Ala Pro Pro Pro Ser
        35
```

<210> SEQ ID NO 118
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 118

```
Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Leu Ala Gly Gly Pro Ser
            20                  25                  30

Ser Gly Ala Pro Pro Pro
        35
```

<210> SEQ ID NO 119
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 119

```
Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30
```

<210> SEQ ID NO 120
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 120

```
Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser
```

<210> SEQ ID NO 121
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 121

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Ile Ala Gly Gly Pro Ser
            20                  25                  30

Ser Gly Ala Pro Pro Pro
        35
```

<210> SEQ ID NO 122

-continued

```
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 122

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro
            20                  25                  30


<210> SEQ ID NO 123
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 123

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro
        35


<210> SEQ ID NO 124
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 124

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly
            20                  25                  30


<210> SEQ ID NO 125
<211> LENGTH: 38
<212> TYPE: PRT
<213> ORGANISM: Artificial Sequence
<220> FEATURE:
```

-continued

<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 125

```
Tyr Xaa Glu Gly Thr Phe Thr Ser Asp Leu Ser Ile Gln Leu Glu Lys
1               5                   10                  15

Glu Ala Val Lys Leu Phe Ile Glu Trp Leu Ile Ala Gly Gly Pro Ser
            20                  25                  30

Ser Gly Ala Pro Pro Pro
        35
```

<210> SEQ ID NO 126
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 126

```
Tyr Xaa Glu Gly Thr Phe Thr Ser Asp Tyr Ser Ile Tyr Leu Glu Lys
1               5                   10                  15

Glu Ala Val Lys Leu Phe Ile Ala Trp Leu Ile Ala Gly Gly Pro Ser
            20                  25                  30

Ser Gly Ala Pro Pro Pro Ser
        35
```

<210> SEQ ID NO 127
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 127

```
Tyr Xaa Glu Gly Thr Phe Thr Ser Asp Leu Ser Ile Ala Leu Glu Lys
1               5                   10                  15

Glu Ala Val Arg Leu Phe Ile Ala Trp Leu Ile Ala Gly Gly Pro Ser
            20                  25                  30

Ser Gly Ala Pro Pro Pro Ser
        35
```

<210> SEQ ID NO 128
<211> LENGTH: 37
<212> TYPE: PRT

-continued

<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 128

Tyr Xaa Glu Gly Thr Phe Thr Ser Asp Leu Ser Ile Gln Leu Glu Lys
1               5                   10                  15

Glu Ala Val Lys Leu Phe Ile Glu Trp Leu Leu Ala Gly Gly Pro Ser
            20                  25                  30

Ser Gly Ala Pro Pro
        35

<210> SEQ ID NO 129
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 129

Tyr Xaa Glu Gly Thr Phe Thr Ser Asp Tyr Ser Ile Tyr Leu Glu Lys
1               5                   10                  15

Glu Ala Val Lys Glu Phe Ile Ala Trp Leu Leu Ala Gly Gly Pro Ser
            20                  25                  30

Ser Gly Ala Pro Pro Pro
        35

<210> SEQ ID NO 130
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 130

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro
            20                  25                  30

<210> SEQ ID NO 131
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 131

```
Tyr Xaa Glu Gly Thr Phe Thr Ser Asp Leu Ser Ile Gln Leu Glu Lys
1               5                   10                  15

Glu Ala Val Lys Leu Phe Ile Glu Trp Leu Leu Ala Gly Gly Pro Ser
            20                  25                  30

Ser Gly Ala Pro
        35
```

<210> SEQ ID NO 132
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 132

```
Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala
        35
```

<210> SEQ ID NO 133
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 133

```
Tyr Xaa Glu Gly Thr Phe Ile Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser
        35
```

<210> SEQ ID NO 134
<211> LENGTH: 31

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 134

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro
            20                  25                  30


<210> SEQ ID NO 135
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 135

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser


<210> SEQ ID NO 136
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 136

Tyr Xaa Glu Gly Thr Phe Thr Ser Asp Leu Ser Ile Xaa Leu Glu Lys
1               5                   10                  15

Glu Ala Val Lys Glu Phe Ile Ala Trp Leu Leu Ala Gly Gly Pro Ser
            20                  25                  30

Ser Gly Ala Pro Pro Pro Ser
        35
```

-continued

```
<210> SEQ ID NO 137
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 137

Tyr Xaa Glu Gly Thr Phe Thr Ser Asp Leu Ser Ile Gln Leu Glu Lys
1               5                   10                  15

Glu Ala Val Lys Leu Phe Ile Glu Trp Leu Leu Ala Gly Gly Pro Ser
            20                  25                  30

Ser Gly Ala
        35


<210> SEQ ID NO 138
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 138

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly


<210> SEQ ID NO 139
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 139

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30


<210> SEQ ID NO 140
<211> LENGTH: 33
```

<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 140

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser

<210> SEQ ID NO 141
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 141

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser
            20                  25                  30

Ser Gly Ala Pro Pro
        35

<210> SEQ ID NO 142
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 142

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro
        35

<210> SEQ ID NO 143

<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 143

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

Ser Gly

<210> SEQ ID NO 144
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 144

Tyr Xaa Glu Gly Thr Phe Thr Ser Asp Tyr Ser Ile Ala Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Ser
35

<210> SEQ ID NO 145
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 145

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro Ser
20 25 30

Ser

<210> SEQ ID NO 146

<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 146

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly
```

<210> SEQ ID NO 147
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 147

```
Tyr Xaa Glu Gly Thr Phe Ile Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser
        35
```

<210> SEQ ID NO 148
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 148

```
Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30
```

Ser Gly

<210> SEQ ID NO 149
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 149

```
Tyr Xaa Glu Gly Thr Phe Thr Ser Asp Tyr Ser Ile Tyr Leu Glu Lys
1               5                   10                  15

Glu Ala Val Lys Glu Phe Ile Ala Trp Leu Ile Ala Gly Gly Pro Ser
            20                  25                  30

Ser Gly Ala Pro Pro Pro Ser
        35
```

<210> SEQ ID NO 150
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 150

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro
        35
```

<210> SEQ ID NO 151
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 151

```
Tyr Xaa Glu Gly Thr Phe Thr Ser Asp Leu Ser Ile Tyr Leu Asp Glu
```

```
1               5                   10                  15

Glu Ala Val Arg Leu Phe Val Asn Trp Leu Leu Ala Gly Gly Pro Ser
            20                  25                  30

Ser Gly Ala Pro Pro Pro Ser
        35
```

<210> SEQ ID NO 152
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 152

```
Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro
            20                  25                  30
```

<210> SEQ ID NO 153
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 153

```
Tyr Xaa Glu Gly Thr Phe Thr Ser Asp Leu Ser Ile Gln Leu Glu Lys
1               5                   10                  15

Glu Ala Val Lys Leu Phe Ile Glu Trp Leu Leu Ala Gly Gly Pro Ser
            20                  25                  30
```

<210> SEQ ID NO 154
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 154

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30
```

Ser Gly Ala Pro Pro
35

<210> SEQ ID NO 155
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 155

Tyr Xaa Glu Gly Thr Phe Thr Ser Asp Tyr Ser Ile Tyr Leu Glu Lys
1 5 10 15

Glu Ala Val Arg Leu Phe Ile Glu Trp Leu Ile Ala Gly Gly
20 25 30

<210> SEQ ID NO 156
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 156

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly Pro
20 25 30

<210> SEQ ID NO 157
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 157

Tyr Xaa Glu Gly Thr Phe Thr Ser Asp Leu Ser Ile Ala Leu Glu Lys
1 5 10 15

Glu Ala Val Gln Asp Phe Val Asn Trp Leu Ile Ala Gly Gly Pro Ser
20 25 30

Ser Gly Ala Pro Pro Pro Ser
35

<210> SEQ ID NO 158
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 158

```
Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30
```

<210> SEQ ID NO 159
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 159

```
Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro Ser
            20                  25                  30

Ser Gly Ala Pro
        35
```

<210> SEQ ID NO 160
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 160

```
Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro
        35
```

```
<210> SEQ ID NO 161
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 161

Tyr Xaa Glu Gly Thr Phe Thr Ser Asp Leu Ser Ile Xaa Leu Glu Lys
1               5                   10                  15

Glu Ala Val Arg Leu Phe Ile Ala Trp Leu Leu Ala Gly Gly Pro Ser
            20                  25                  30

Ser Gly Ala Pro Pro Pro Ser
        35


<210> SEQ ID NO 162
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 162

Tyr Xaa Glu Gly Thr Phe Thr Ser Asp Tyr Ser Ile Gln Leu Asp Glu
1               5                   10                  15

Glu Ala Val Arg Leu Phe Val Asn Trp Leu Leu Ala Gly Gly Pro Ser
            20                  25                  30

Ser Gly Ala Pro Pro Pro Ser
        35


<210> SEQ ID NO 163
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 163

Tyr Xaa Glu Gly Thr Phe Thr Ser Asp Leu Ser Ile Ala Leu Glu Lys
1               5                   10                  15

Glu Ala Val Lys Glu Phe Ile Ala Trp Leu Ile Ala Gly Gly Pro Ser
```

-continued

```
            20                  25                  30

Ser Gly Ala Pro Pro Pro Ser
        35


<210> SEQ ID NO 164
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 164

Tyr Xaa Glu Gly Thr Phe Thr Ser Asp Tyr Ser Ile Tyr Leu Glu Lys
1               5                   10                  15

Glu Ala Val Arg Leu Phe Ile Glu Trp Leu Ile Ala Gly Gly Pro Ser
            20                  25                  30


<210> SEQ ID NO 165
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 165

Tyr Xaa Glu Gly Thr Phe Thr Ser Asp Tyr Ser Ile Tyr Leu Asp Glu
1               5                   10                  15

Glu Ala Val Arg Leu Phe Val Asn Trp Leu Ile Ala Gly Gly Pro Ser
            20                  25                  30

Ser Gly


<210> SEQ ID NO 166
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 166

Tyr Xaa Glu Gly Thr Phe Thr Ser Asp Leu Ser Ile Xaa Leu Glu Lys
1               5                   10                  15
```

```
Glu Ala Val Gln Asp Phe Val Asn Trp Leu Leu Ala Gly Gly Pro Ser
            20                  25                  30

Ser Gly Ala Pro Pro Pro Ser
        35


<210> SEQ ID NO 167
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 167

Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro Ser
            20                  25                  30

Ser Gly Ala Pro
        35


<210> SEQ ID NO 168
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 168

Tyr Xaa Glu Gly Thr Phe Thr Ser Asp Leu Ser Lys Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro
        35


<210> SEQ ID NO 169
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
```

<223> OTHER INFORMATION: AMIDATION, C-termianl amidation

<400> SEQUENCE: 169

```
Tyr Xaa Glu Gly Thr Phe Thr Ser Asp Tyr Ser Ile Tyr Leu Asp Glu
1               5                   10                  15

Glu Ala Val Lys Glu Phe Ile Ala Trp Leu Ile Ala Gly Gly Pro Ser
            20                  25                  30

Ser Gly Ala Pro Pro Pro Ser
        35
```

<210> SEQ ID NO 170
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 170

```
Tyr Xaa Glu Gly Thr Phe Thr Ser Asp Leu Ser Ile Tyr Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro
        35
```

<210> SEQ ID NO 171
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 171

```
Tyr Xaa Glu Gly Thr Phe Thr Ser Asp Tyr Ser Ile Ala Leu Asp Glu
1               5                   10                  15

Glu Ala Val Arg Leu Phe Val Asn Trp Leu Leu Ala Gly Gly Pro Ser
            20                  25                  30

Ser Gly Ala Pro Pro Pro Ser
        35
```

<210> SEQ ID NO 172
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:

<221> NAME/KEY: MOD_RES
<222> LOCATION: (39)..(39)
<223> OTHER INFORMATION: AMIDATION, C-termianl amidation

<400> SEQUENCE: 172

Tyr Xaa Glu Gly Thr Phe Thr Ser Asp Leu Ser Ile Ala Leu Glu Lys
1 5 10 15

Glu Ala Val Lys Leu Phe Val Asn Trp Leu Leu Ala Gly Gly Pro Ser
20 25 30

Ser Gly Ala Pro Pro Pro Ser
35

<210> SEQ ID NO 173
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 173

Tyr Xaa Glu Gly Thr Phe Thr Ser Asp Leu Ser Ile Tyr Leu Glu Lys
1 5 10 15

Glu Ala Val Arg Leu Phe Ile Glu Trp Leu Leu Ala Gly Gly Pro Ser
20 25 30

Ser Gly Ala Pro
35

<210> SEQ ID NO 174
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 174

Tyr Xaa Glu Gly Thr Phe Thr Ser Asp Leu Ser Ile Xaa Leu Glu Lys
1 5 10 15

Glu Ala Val Arg Leu Phe Ile Glu Trp Leu Leu Ala Gly Gly
20 25 30

<210> SEQ ID NO 175
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 175

Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro Ser
            20                  25                  30

Ser Gly Ala
        35

<210> SEQ ID NO 176
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 176

Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro Ser
            20                  25                  30

<210> SEQ ID NO 177
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 177

Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro Ser
            20                  25                  30

Ser Gly Ala Pro Pro Pro
        35

<210> SEQ ID NO 178
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)

<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 178

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30
```

<210> SEQ ID NO 179
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 179

```
Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro
        35
```

<210> SEQ ID NO 180
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 180

```
Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro Ser
            20                  25                  30

Ser Gly
```

<210> SEQ ID NO 181
<211> LENGTH: 34
<212> TYPE: PRT
<213> ORGANISM: Artificial Sequence
<220> FEATURE:
<223> OTHER INFORMATION: synthetic peptide
<220> FEATURE:

<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 181

Tyr Xaa Glu Gly Thr Phe Thr Ser Asp Leu Ser Ile Xaa Leu Glu Lys
1 5 10 15

Glu Ala Val Arg Leu Phe Ile Glu Trp Leu Leu Ala Gly Gly Pro Ser
20 25 30

Ser Gly

<210> SEQ ID NO 182
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 182

Tyr Xaa Glu Gly Thr Phe Thr Ser Asp Tyr Ser Ile Gln Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Ser
35

<210> SEQ ID NO 183
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 183

Tyr Xaa Glu Gly Thr Phe Thr Ser Asp Leu Ser Ile Tyr Leu Glu Lys
1 5 10 15

Glu Ala Val Lys Leu Phe Val Asn Trp Leu Leu Ala Gly Gly Pro Ser
20 25 30

Ser Gly Ala Pro Pro Pro
35

<210> SEQ ID NO 184
<211> LENGTH: 33

<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 184

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30

Ser
```

<210> SEQ ID NO 185
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 185

```
Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro Ser
            20                  25                  30

Ser Gly Ala
        35
```

<210> SEQ ID NO 186
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 186

```
Tyr Xaa Glu Gly Thr Phe Thr Ser Asp Tyr Ser Ile Xaa Leu Glu Lys
1               5                   10                  15
```

Glu Ala Val Arg Leu Phe Ile Glu Trp Leu Leu Ala Gly Gly Pro Ser
            20                  25                  30

Ser Gly Ala Pro Pro Pro Ser
        35

<210> SEQ ID NO 187
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 187

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly
            20                  25                  30

<210> SEQ ID NO 188
<211> LENGTH: 36
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (36)..(36)
<223> OTHER INFORMATION: AMIDATION, C-termianl amidation

<400> SEQUENCE: 188

Tyr Xaa Glu Gly Thr Phe Thr Ser Asp Leu Ser Ile Gln Leu Glu Lys
1               5                   10                  15

Glu Ala Val Arg Leu Phe Ile Glu Trp Leu Leu Ala Gly Gly Pro Ser
            20                  25                  30

Ser Gly Ala Pro
        35

<210> SEQ ID NO 189
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 189

Tyr Xaa Glu Gly Thr Phe Thr Ser Asp Tyr Ser Ile Tyr Leu Glu Lys
1               5                   10                  15

Glu Ala Val Lys Leu Phe Val Asn Trp Leu Ile Ala Gly Gly Pro Ser

-continued 20 25 30

<210> SEQ ID NO 190
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 190

Tyr Xaa Glu Gly Thr Phe Thr Ser Asp Leu Ser Ile Tyr Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Ser
35

<210> SEQ ID NO 191
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 191

Tyr Xaa Glu Gly Thr Phe Thr Ser Asp Leu Ser Ile Xaa Leu Glu Lys
1 5 10 15

Glu Ala Val Arg Leu Phe Val Asn Trp Leu Leu Ala Gly Gly Pro Ser
20 25 30

Ser Gly Ala Pro Pro Pro Ser
35

<210> SEQ ID NO 192
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 192

Tyr Xaa Glu Gly Thr Phe Thr Ser Asp Leu Ser Ile Tyr Leu Asp Glu

-continued

```
1               5                   10                  15

Glu Ala Val Arg Leu Phe Val Asn Trp Leu Leu Ala Gly Gly Pro Ser
            20                  25                  30

Ser Gly


<210> SEQ ID NO 193
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 193

Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro Ser
            20                  25                  30


<210> SEQ ID NO 194
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 194

Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro Ser
            20                  25                  30

Ser


<210> SEQ ID NO 195
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 195
```

```
Tyr Xaa Glu Gly Thr Phe Thr Ser Asp Leu Ser Lys Xaa Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro Ser
        35


<210> SEQ ID NO 196
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (34)..(34)
<223> OTHER INFORMATION: AMIDATION, C-termianl amidation

<400> SEQUENCE: 196

Tyr Xaa Glu Gly Thr Phe Thr Ser Asp Leu Ser Ile Tyr Leu Glu Lys
1               5                   10                  15

Glu Ala Val Arg Leu Phe Ile Glu Trp Leu Leu Ala Gly Gly Pro Ser
            20                  25                  30

Ser Gly


<210> SEQ ID NO 197
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 197

Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro Ser
            20                  25                  30

Ser Gly Ala Pro Pro
        35


<210> SEQ ID NO 198
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (32)..(32)
<223> OTHER INFORMATION: AMIDATION, C-termianl amidation

<400> SEQUENCE: 198
```

Tyr Xaa Glu Gly Thr Phe Thr Ser Asp Leu Ser Ile Tyr Leu Glu Lys
1 5 10 15

Glu Ala Val Arg Leu Phe Ile Glu Trp Leu Leu Ala Gly Gly Pro Ser
20 25 30

<210> SEQ ID NO 199
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 199

Tyr Xaa Glu Gly Thr Phe Thr Ser Asp Leu Ser Ile Xaa Leu Glu Lys
1 5 10 15

Glu Ala Val Arg Leu Phe Ile Glu Trp Leu Leu Ala Gly Gly Pro
20 25 30

<210> SEQ ID NO 200
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 200

Tyr Xaa Glu Gly Thr Phe Thr Ser Asp Leu Ser Ile Tyr Leu Glu Lys
1 5 10 15

Glu Ala Val Arg Leu Phe Ile Glu Trp Leu Leu Ala Gly Gly Pro
20 25 30

<210> SEQ ID NO 201
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 201

Tyr Xaa Glu Gly Thr Phe Thr Ser Asp Leu Ser Ile Tyr Leu Asp Glu
1 5 10 15

```
Glu Ala Val Arg Leu Phe Val Asn Trp Leu Leu Ala Gly Gly
            20                  25                  30


<210> SEQ ID NO 202
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 202

Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro Ser
            20                  25                  30

Ser Gly Ala Pro Pro Pro Ser
        35


<210> SEQ ID NO 203
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 203

Tyr Xaa Glu Gly Thr Phe Thr Ser Asp Leu Ser Ile Tyr Leu Glu Lys
1               5                   10                  15

Glu Ala Val Arg Leu Phe Ile Glu Trp Leu Leu Ala Gly Gly Pro Ser
            20                  25                  30

Ser


<210> SEQ ID NO 204
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 204

Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro
```

20 25 30

<210> SEQ ID NO 205
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 205

Tyr Xaa Glu Gly Thr Phe Thr Ser Asp Leu Ser Ile Tyr Leu Glu Lys
1 5 10 15

Glu Ala Val Lys Leu Phe Val Asn Trp Leu Leu Ala Gly Gly Pro Ser
20 25 30

Ser

<210> SEQ ID NO 206
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 206

Tyr Xaa Glu Gly Thr Phe Thr Ser Asp Leu Ser Ile Gln Leu Glu Lys
1 5 10 15

Glu Ala Val Lys Leu Phe Ile Glu Trp Leu Leu Ala Gly Gly
20 25 30

<210> SEQ ID NO 207
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 207

Tyr Xaa Glu Gly Thr Phe Thr Ser Asp Tyr Ser Ile Tyr Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro
35

<210> SEQ ID NO 208
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (31)..(31)
<223> OTHER INFORMATION: AMIDATION, C-termianl amidation

<400> SEQUENCE: 208

```
Tyr Xaa Glu Gly Thr Phe Thr Ser Asp Leu Ser Ile Tyr Leu Glu Lys
1               5                   10                  15

Glu Ala Val Lys Leu Phe Val Asn Trp Leu Leu Ala Gly Gly Pro
            20                  25                  30
```

<210> SEQ ID NO 209
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 209

```
Tyr Xaa Glu Gly Thr Phe Thr Ser Asp Leu Ser Ile Tyr Leu Glu Lys
1               5                   10                  15

Glu Ala Val Arg Leu Phe Ile Glu Trp Leu Leu Ala Gly Gly Pro Ser
            20                  25                  30

Ser Gly Ala Pro Pro Pro
        35
```

<210> SEQ ID NO 210
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (38)..(38)
<223> OTHER INFORMATION: AMIDATION, C-termianl amidation

<400> SEQUENCE: 210

```
Tyr Xaa Glu Gly Thr Phe Thr Ser Asp Leu Ser Ile Xaa Leu Glu Lys
1               5                   10                  15

Glu Ala Val Arg Leu Phe Ile Glu Trp Leu Leu Ala Gly Gly Pro Ser
            20                  25                  30
```

Ser Gly Ala Pro Pro Pro
35

<210> SEQ ID NO 211
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (35)..(35)
<223> OTHER INFORMATION: AMIDATION, C-termianl amidation

<400> SEQUENCE: 211

Tyr Xaa Glu Gly Thr Phe Thr Ser Asp Leu Ser Ile Tyr Leu Glu Lys
1 5 10 15

Glu Ala Val Arg Leu Phe Ile Glu Trp Leu Leu Ala Gly Gly Pro Ser
20 25 30

Ser Gly Ala
35

<210> SEQ ID NO 212
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 212

Tyr Xaa Glu Gly Thr Phe Thr Ser Asp Leu Ser Ile Tyr Leu Glu Lys
1 5 10 15

Glu Ala Val Lys Leu Phe Val Asn Trp Leu Leu Ala Gly Gly
20 25 30

<210> SEQ ID NO 213
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 213

Tyr Xaa Glu Gly Thr Phe Thr Ser Asp Tyr Ser Ile Xaa Leu Asp Glu
1 5 10 15

```
Glu Ala Val Arg Leu Phe Val Asn Trp Leu Leu Ala Gly Gly Pro Ser
            20                  25                  30

Ser Gly Ala Pro Pro Pro Ser
        35


<210> SEQ ID NO 214
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (33)..(33)
<223> OTHER INFORMATION: AMIDATION, C-termianl amidation

<400> SEQUENCE: 214

Tyr Xaa Glu Gly Thr Phe Thr Ser Asp Leu Ser Ile Ala Leu Glu Lys
1               5                   10                  15

Glu Ala Val Arg Leu Phe Ile Glu Trp Leu Leu Ala Gly Gly Pro Ser
            20                  25                  30

Ser


<210> SEQ ID NO 215
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (37)..(37)
<223> OTHER INFORMATION: AMIDATION, C-termianl amidation

<400> SEQUENCE: 215

Tyr Xaa Glu Gly Thr Phe Thr Ser Asp Leu Ser Ile Tyr Leu Asp Glu
1               5                   10                  15

Glu Ala Val Arg Leu Phe Val Asn Trp Leu Leu Ala Gly Gly Pro Ser
            20                  25                  30

Ser Gly Ala Pro Pro
        35


<210> SEQ ID NO 216
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (13)..(13)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation
```

<400> SEQUENCE: 216

Tyr Xaa Glu Gly Thr Phe Thr Ser Asp Leu Ser Ile Xaa Leu Glu Lys
1 5 10 15

Glu Ala Val Lys Leu Phe Val Asn Trp Leu Leu Ala Gly Gly Pro Ser
20 25 30

Ser Gly Ala Pro Pro Pro Ser
35

<210> SEQ ID NO 217
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 217

Tyr Xaa Glu Gly Thr Phe Thr Ser Asp Leu Ser Ser Ala Leu Glu Lys
1 5 10 15

Glu Ala Val Arg Leu Phe Ile Glu Trp Leu Leu Ala Gly Gly Pro Ser
20 25 30

Ser Gly Ala Pro Pro Pro Lys
35

<210> SEQ ID NO 218
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (30)..(30)
<223> OTHER INFORMATION: AMIDATION, C-termianl amidation

<400> SEQUENCE: 218

Tyr Xaa Glu Gly Thr Phe Thr Ser Asp Leu Ser Ile Tyr Leu Glu Lys
1 5 10 15

Glu Ala Val Arg Leu Phe Ile Glu Trp Leu Leu Ala Gly Gly
20 25 30

<210> SEQ ID NO 219
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X=aminoisobutyric aicd
<220> FEATURE:
<221> NAME/KEY: MOD_RES
<222> LOCATION: (39)..(39)
<223> OTHER INFORMATION: AMIDATION, C-termianl amidation

<400> SEQUENCE: 219

```
Tyr Xaa Glu Gly Thr Phe Thr Ser Asp Leu Ser Ile Gln Leu Glu Lys
1               5                   10                  15

Glu Ala Val Lys Leu Phe Val Asn Trp Leu Leu Ala Gly Gly Pro Ser
            20                  25                  30

Ser Gly Ala Pro Pro Pro Ser
        35
```

```
<210> SEQ ID NO 220
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Xaa=aminoisobutyric aicd
<220> FEATURE:
<221> NAME/KEY: MOD_RES
<222> LOCATION: (7)..(7)
<223> OTHER INFORMATION: Xaa=Thr or Ile.
<220> FEATURE:
<221> NAME/KEY: MOD_RES
<222> LOCATION: (10)..(10)
<223> OTHER INFORMATION: Xaa=Leu or Tyr.
<220> FEATURE:
<221> NAME/KEY: MOD_RES
<222> LOCATION: (12)..(12)
<223> OTHER INFORMATION: Xaa=Ile, Ser or Lys.
<220> FEATURE:
<221> NAME/KEY: MOD_RES
<222> LOCATION: (13)..(13)
<223> OTHER INFORMATION: Xaa=Gln, Ala, aib or Tyr.
<220> FEATURE:
<221> NAME/KEY: MOD_RES
<222> LOCATION: (15)..(15)
<223> OTHER INFORMATION: Xaa=Asp or GLu.
<220> FEATURE:
<221> NAME/KEY: MOD_RES
<222> LOCATION: (16)..(16)
<223> OTHER INFORMATION: Xaa=Glu or Lys.
<220> FEATURE:
<221> NAME/KEY: MOD_RES
<222> LOCATION: (19)..(19)
<223> OTHER INFORMATION: Xaa=Val or Ala.
<220> FEATURE:
<221> NAME/KEY: MOD_RES
<222> LOCATION: (20)..(20)
<223> OTHER INFORMATION: Xaa=Lys, Arg or Gln.
<220> FEATURE:
<221> NAME/KEY: MOD_RES
<222> LOCATION: (21)..(21)
<223> OTHER INFORMATION: Xaa=Leu, Glu, or Asp.
<220> FEATURE:
<221> NAME/KEY: MOD_RES
<222> LOCATION: (23)..(23)
<223> OTHER INFORMATION: Xaa=Ile or Val
<220> FEATURE:
<221> NAME/KEY: MOD_RES
<222> LOCATION: (24)..(24)
<223> OTHER INFORMATION: Xaa=Glu, Gln, Asn, or Ala.
<220> FEATURE:
<221> NAME/KEY: MOD_RES
<222> LOCATION: (27)..(27)
<223> OTHER INFORMATION: Xaa=Ile or Leu.
<220> FEATURE:
<221> NAME/KEY: MOD_RES
<222> LOCATION: (30)..(30)
<223> OTHER INFORMATION: Xaa does not exsist or is GPSSGAPPP, GPPSGAPPP,
      GPSSGKPPP, GPSSGEPPP, GPSSaibAPPP, GPSSGAPP, GPSSGAP, GPSSGA,
      GPSSG, GPSS, GPS, GP or G.

<400> SEQUENCE: 220

Tyr Xaa Glu Gly Thr Phe Xaa Ser Asp Xaa Ser Xaa Xaa Leu Xaa Xaa
```

-continued

```
1               5                   10                  15

Glu Ala Xaa Xaa Xaa Phe Xaa Xaa Trp Leu Xaa Ala Gly Xaa
            20                  25                  30


<210> SEQ ID NO 221
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Xaa=aminoisobutyric aicd
<220> FEATURE:
<221> NAME/KEY: MOD_RES
<222> LOCATION: (10)..(10)
<223> OTHER INFORMATION: Xaa=Leu or Tyr
<220> FEATURE:
<221> NAME/KEY: MOD_RES
<222> LOCATION: (13)..(13)
<223> OTHER INFORMATION: Xaa=Gln, Ala, aminoisobutyric aicd or Tyr
<220> FEATURE:
<221> NAME/KEY: MOD_RES
<222> LOCATION: (15)..(15)
<223> OTHER INFORMATION: Xaa=Asp or Glu
<220> FEATURE:
<221> NAME/KEY: MOD_RES
<222> LOCATION: (16)..(16)
<223> OTHER INFORMATION: Xaa=Glu or Lys
<220> FEATURE:
<221> NAME/KEY: MOD_RES
<222> LOCATION: (19)..(19)
<223> OTHER INFORMATION: Xaa=Val or Ala
<220> FEATURE:
<221> NAME/KEY: MOD_RES
<222> LOCATION: (20)..(20)
<223> OTHER INFORMATION: Xaa=Lys or Arg
<220> FEATURE:
<221> NAME/KEY: MOD_RES
<222> LOCATION: (23)..(23)
<223> OTHER INFORMATION: Xaa=Ile or Val
<220> FEATURE:
<221> NAME/KEY: MOD_RES
<222> LOCATION: (24)..(24)
<223> OTHER INFORMATION: Xaa=Glu, Ala, Gln or Asn
<220> FEATURE:
<221> NAME/KEY: MOD_RES
<222> LOCATION: (27)..(27)
<223> OTHER INFORMATION: Xaa=Ile or Leu
<220> FEATURE:
<221> NAME/KEY: MOD_RES
<222> LOCATION: (30)..(30)
<223> OTHER INFORMATION: Xaa does not exsist or is GPSSGAPPP, GPPSGAPPP,
      GPSSGKPPP, GPSSGEPPP, GPSSaibAPPP, GPSSGAPP, GPSSGAP, GPSSGA,
      GPSSG, GPSS, GPS, GP or G.

<400> SEQUENCE: 221

Tyr Xaa Glu Gly Thr Phe Thr Ser Asp Xaa Ser Ile Xaa Leu Xaa Xaa
1               5                   10                  15

Glu Ala Xaa Xaa Leu Phe Xaa Xaa Trp Leu Xaa Ala Gly Xaa
            20                  25                  30


<210> SEQ ID NO 222
<211> LENGTH: 11
<212> TYPE: PRT
<213> ORGANISM: Artificial Sequence
<220> FEATURE:
<223> OTHER INFORMATION: synthetic peptide

<400> SEQUENCE: 222

Gly Pro Ser Ser Gly Ala Pro Pro Pro Ser Lys
1               5                   10
```

<210> SEQ ID NO 223
<211> LENGTH: 11
<212> TYPE: PRT
<213> ORGANISM: Artificial Sequence
<220> FEATURE:
<223> OTHER INFORMATION: synthetic peptide

<400> SEQUENCE: 223

Gly Pro Ser Ser Gly Ala Pro Pro Pro Ser Cys
1               5                   10

<210> SEQ ID NO 224
<211> LENGTH: 10
<212> TYPE: PRT
<213> ORGANISM: Artificial Sequence
<220> FEATURE:
<223> OTHER INFORMATION: synthetic peptide

<400> SEQUENCE: 224

Gly Pro Ser Ser Gly Ala Pro Pro Pro Ser
1               5                   10

<210> SEQ ID NO 225
<211> LENGTH: 10
<212> TYPE: PRT
<213> ORGANISM: Artificial Sequence
<220> FEATURE:
<223> OTHER INFORMATION: synthetic peptide

<400> SEQUENCE: 225

Gly Pro Ser Ser Gly Ala Pro Pro Pro Lys
1               5                   10

<210> SEQ ID NO 226
<211> LENGTH: 10
<212> TYPE: PRT
<213> ORGANISM: Artificial Sequence
<220> FEATURE:
<223> OTHER INFORMATION: synthetic peptide

<400> SEQUENCE: 226

Gly Pro Ser Ser Gly Ala Pro Pro Pro Cys
1               5                   10

<210> SEQ ID NO 227
<211> LENGTH: 9
<212> TYPE: PRT
<213> ORGANISM: Artificial Sequence
<220> FEATURE:
<223> OTHER INFORMATION: synthetic peptide

<400> SEQUENCE: 227

Gly Pro Ser Ser Gly Ala Pro Pro Pro
1               5

<210> SEQ ID NO 228
<211> LENGTH: 9
<212> TYPE: PRT
<213> ORGANISM: Artificial Sequence
<220> FEATURE:
<223> OTHER INFORMATION: synthetic peptide

<400> SEQUENCE: 228

Gly Pro Ser Ser Gly Lys Pro Pro Pro
1               5

<210> SEQ ID NO 229
<211> LENGTH: 9
<212> TYPE: PRT
<213> ORGANISM: Artificial Sequence
<220> FEATURE:
<223> OTHER INFORMATION: synthetic peptide

<400> SEQUENCE: 229

Gly Pro Ser Ser Gly Glu Pro Pro Pro
1 5

<210> SEQ ID NO 230
<211> LENGTH: 8
<212> TYPE: PRT
<213> ORGANISM: Artificial Sequence
<220> FEATURE:
<223> OTHER INFORMATION: synthetic peptide

<400> SEQUENCE: 230

Gly Pro Ser Ser Gly Ala Pro Pro
1 5

<210> SEQ ID NO 231
<211> LENGTH: 7
<212> TYPE: PRT
<213> ORGANISM: Artificial Sequence
<220> FEATURE:
<223> OTHER INFORMATION: synthetic peptide

<400> SEQUENCE: 231

Gly Pro Ser Ser Gly Ala Pro
1 5

<210> SEQ ID NO 232
<211> LENGTH: 6
<212> TYPE: PRT
<213> ORGANISM: Artificial Sequence
<220> FEATURE:
<223> OTHER INFORMATION: synthetic peptide

<400> SEQUENCE: 232

Gly Pro Ser Ser Gly Ala
1 5

<210> SEQ ID NO 233
<211> LENGTH: 5
<212> TYPE: PRT
<213> ORGANISM: Artificial Sequence
<220> FEATURE:
<223> OTHER INFORMATION: synthetic peptide

<400> SEQUENCE: 233

Gly Pro Ser Ser Gly
1 5

<210> SEQ ID NO 234
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (5)..(5)
<223> OTHER INFORMATION: Xaa=aminoisobutyric aicd

<400> SEQUENCE: 234

-continued

```
Gly Pro Ser Ser Xaa Ala Pro Pro Pro
1               5


<210> SEQ ID NO 235
<211> LENGTH: 4
<212> TYPE: PRT
<213> ORGANISM: Artificial Sequence
<220> FEATURE:
<223> OTHER INFORMATION: synthetic peptide

<400> SEQUENCE: 235

Gly Pro Ser Ser
1


<210> SEQ ID NO 236
<211> LENGTH: 3
<212> TYPE: PRT
<213> ORGANISM: Artificial Sequence
<220> FEATURE:
<223> OTHER INFORMATION: synthetic peptide

<400> SEQUENCE: 236

Gly Pro Ser
1


<210> SEQ ID NO 237
<211> LENGTH: 9
<212> TYPE: PRT
<213> ORGANISM: Artificial Sequence
<220> FEATURE:
<223> OTHER INFORMATION: synthetic peptide

<400> SEQUENCE: 237

Gly Pro Pro Ser Gly Ala Pro Pro Pro
1               5


<210> SEQ ID NO 238
<211> LENGTH: 2
<212> TYPE: PRT
<213> ORGANISM: Artificial Sequence
<220> FEATURE:
<223> OTHER INFORMATION: synthetic peptide

<400> SEQUENCE: 238

Gly Pro
1
```